US011584793B2

(12) United States Patent
Dengl et al.

(10) Patent No.: US 11,584,793 B2
(45) Date of Patent: Feb. 21, 2023

(54) ANTI-TRANSFERRIN RECEPTOR ANTIBODIES WITH TAILORED AFFINITY

(71) Applicant: Hoffmann-La Roche Inc., Little Falls, NJ (US)

(72) Inventors: Stefan Dengl, Munich (DE); Guy Georges, Habach (DE); Ulrich Goepfert, Penzberg (DE); Jens Niewoehner, Munich (DE); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/397,227

(22) Filed: Apr. 29, 2019

(65) Prior Publication Data

US 2020/0055931 A1    Feb. 20, 2020

Related U.S. Application Data

(63) Continuation of application No. 15/847,448, filed on Dec. 19, 2017, now Pat. No. 10,323,089, which is a continuation of application No. PCT/EP2016/064460, filed on Jun. 22, 2016.

(30) Foreign Application Priority Data

Jun. 24, 2015 (EP) ..................... 15173508
Jul. 9, 2015 (EP) ..................... 15176084

(51) Int. Cl.
*A61K 39/395* (2006.01)
*A61P 25/00* (2006.01)
*C07K 16/28* (2006.01)
*C07K 14/79* (2006.01)

(52) U.S. Cl.
CPC .......... *C07K 16/28* (2013.01); *A61K 39/3955* (2013.01); *C07K 14/79* (2013.01); *C07K 16/2881* (2013.01); *A61P 25/00* (2018.01); *C07K 2317/24* (2013.01); *C07K 2317/31* (2013.01); *C07K 2317/33* (2013.01); *C07K 2317/56* (2013.01); *C07K 2317/626* (2013.01); *C07K 2317/75* (2013.01); *C07K 2317/76* (2013.01)

(58) Field of Classification Search
CPC ............. C07K 16/28; C07K 16/2881; C07K 2317/75; C07K 14/79; C07K 2317/56; C07K 2317/76; C07K 16/2863; A61K 39/3955
See application file for complete search history.

(56) References Cited

U.S. PATENT DOCUMENTS 3,773,919 A   11/1973  Boswell et al.
4,120,649 A   10/1978  Schechter
4,665,077 A   5/1987   Stringfellow et al.
4,737,456 A   4/1988   Weng et al.
4,816,567 A   3/1989   Cabilly et al.
4,861,579 A   8/1989   Meyer et al.
4,892,538 A   1/1990   Aebischer et al.
5,114,721 A   5/1992   Cohen et al.
5,154,924 A   10/1992  Friden
5,195,317 A   3/1993   Nobue et al.
5,208,020 A   5/1993   Chari et al.
5,231,000 A   7/1993   Majocha et al.
5,283,187 A   2/1994   Aebischer et al.
5,416,064 A   5/1995   Chari et al.
5,427,927 A   6/1995   Meyer et al.
5,500,362 A   3/1996   Robinson et al.
5,595,721 A   1/1997   Kaminski et al.
5,635,483 A   3/1997   Pettit et al.
5,624,821 A   4/1997   Winter et al.
5,648,237 A   7/1997   Carter et al.
5,648,260 A   7/1997   Winter et al.
5,677,180 A   10/1997  Robinson et al.
5,688,651 A   11/1997  Solomon et al.
5,712,374 A   1/1998   Kunstmann et al.

(Continued)

FOREIGN PATENT DOCUMENTS

CL   201403161   11/2014
CL   201503406   11/2015

(Continued)

OTHER PUBLICATIONS

Boado et al., "Drug targeting of erythropoietin across the primate blood-brain barrier with an IgG molecular Trojan horse" J Pharm Exp Ther, Am Soc Pharm Exp Ther 333(3):961-969 (Jun. 1, 2010).
Boado et al., "Engineering and expression of a chimeric transferrin receptor monoclonal antibody for blood-brain barrier delivery in the mouse" Biotechnol Bioeng 102(4):1251-1258 (Mar. 1, 2009).
Boado, R.J. et al., "Selective targeting of a TNFR decoy receptor pharmaceutical to the primate brain as a receptor-specific IgG fusion protein" Journal of Biotechnology 146:84-91 ( 2010).
Hust et al., "Single chain Fab (scFab) fragment" BMC Biotechnology 7:1-15 ( 2007).
ISR and Written Opinion of PCT/EP2016/064460 (Dated as of the actual completion of the international search Sep. 13, 2016).

(Continued)

*Primary Examiner* — Olga N Chernyshev
(74) *Attorney, Agent, or Firm* — Yan Qi

(57) ABSTRACT

Herein is reported an anti-transferrin receptor antibody that specifically binds to human transferrin receptor and cynomolgus transferrin receptor, which comprises i) a humanized heavy chain variable domain derived from the heavy chain variable domain of SEQ ID NO: 01, and ii) a humanized light chain variable domain derived from the light chain variable domain of SEQ ID NO: 26, wherein the antibody has an off-rate for the human transferrin receptor that is equal to or less than (i.e. at most) the off-rate of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 64 and a light chain variable domain of SEQ ID NO: 65.

20 Claims, 4 Drawing Sheets

Specification includes a Sequence Listing.

(56) References Cited

U.S. PATENT DOCUMENTS

| | | |
|---|---|---|
| 5,721,108 A | 2/1998 | Robinson et al. |
| 5,714,586 A | 3/1998 | Kunstmann et al. |
| 5,736,137 A | 4/1998 | Anderson et al. |
| 5,739,116 A | 4/1998 | Hamann et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,776,456 A | 7/1998 | Anderson et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,843,398 A | 12/1998 | Kaminski et al. |
| 5,843,439 A | 12/1998 | Anderson et al. |
| 5,849,898 A | 12/1998 | Seed et al. |
| 5,877,296 A | 3/1999 | Hamann et al. |
| 5,955,317 A | 9/1999 | Suzuki et al. |
| 5,959,177 A | 9/1999 | Hein et al. |
| 6,015,542 A | 1/2000 | Kaminski et al. |
| 6,015,555 A | 1/2000 | Friden |
| 6,040,498 A | 3/2000 | Stomp et al. |
| 6,066,652 A | 5/2000 | Zenner et al. |
| 6,075,181 A | 6/2000 | Kucherlapati et al. |
| 6,083,747 A | 7/2000 | Wong et al. |
| 6,090,365 A | 7/2000 | Kaminski et al. |
| 6,120,767 A | 9/2000 | Robinson et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,267,958 B1 | 7/2001 | Andya et al. |
| 6,287,537 B1 | 9/2001 | Kaminski et al. |
| 6,306,393 B1 | 10/2001 | Goldenberg |
| 6,368,596 B1 | 4/2002 | Ghetie et al. |
| 6,399,061 B1 | 4/2002 | Anderson et al. |
| 6,410,391 B1 | 6/2002 | Zelsacher |
| 6,420,548 B1 | 7/2002 | Vezina et al. |
| 6,417,429 B1 | 9/2002 | Hein et al. |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,565,827 B1 | 5/2003 | Kaminski et al. |
| 6,602,684 B1 | 8/2003 | Umana et al. |
| 6,630,579 B2 | 10/2003 | Chari et al. |
| 6,652,852 B1 | 11/2003 | Robinson et al. |
| 6,682,734 B1 | 1/2004 | Anderson et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,332,581 B2 | 2/2008 | Presta et al. |
| 7,371,826 B2 | 5/2008 | Presta et al. |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,794,719 B2 | 9/2010 | Bardroff |
| 8,883,980 B2 | 11/2014 | Umana et al. |
| 8,945,867 B2 | 2/2015 | Ogawa et al. |
| 9,598,496 B2 | 3/2017 | Kurosawa et al. |
| 9,714,292 B2 | 7/2017 | Auer et al. |
| 10,323,089 B2 | 6/2019 | Dengl et al. |
| 10,323,099 B2 | 6/2019 | Bruenker et al. |
| 10,364,292 B2 | 7/2019 | Rueger et al. |
| 10,370,692 B2 | 8/2019 | Kopetzki et al. |
| 10,941,205 B2 | 3/2021 | Duerr et al. |
| 11,098,338 B2 | 8/2021 | Kopetzki et al. |
| 2001/0018041 A1 | 8/2001 | Hanna et al. |
| 2001/0056066 A1 | 12/2001 | Bugelski et al. |
| 2002/0006404 A1 | 1/2002 | Hanna et al. |
| 2002/0009427 A1 | 1/2002 | Wolin et al. |
| 2002/0009444 A1 | 1/2002 | Grillo-Lopez |
| 2002/0012665 A1 | 1/2002 | Hanna |
| 2002/0025313 A1 | 2/2002 | Micklus et al. |
| 2002/0058029 A1 | 5/2002 | Hanna |
| 2002/0164328 A1 | 7/2002 | Shinkawa et al. |
| 2002/0127652 A1 | 9/2002 | Schambye et al. |
| 2002/0136719 A1 | 9/2002 | Shenoy et al. |
| 2002/0004587 A1 | 10/2002 | Miller et al. |
| 2002/0041847 A1 | 11/2002 | Goldenberg |
| 2002/0128488 A1 | 12/2002 | Yamakawa et al. |
| 2002/0197255 A1 | 12/2002 | Anderson et al. |
| 2003/0003097 A1 | 1/2003 | Reff et al. |
| 2003/0021781 A1 | 1/2003 | Anderson et al. |
| 2003/0185796 A1 | 2/2003 | Wolin et al. |
| 2003/0068664 A1 | 4/2003 | Albitar et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0115614 A1 | 6/2003 | Kanda et al. |
| 2003/0133930 A1 | 7/2003 | Goldenberg et al. |
| 2003/0147885 A1 | 8/2003 | Anderson et al. |
| 2003/0148404 A1 | 8/2003 | MIchaelson |
| 2003/0157108 A1 | 8/2003 | Presta |
| 2003/0180292 A1 | 9/2003 | Hanna et al. |
| 2003/0202972 A1 | 10/2003 | Andya et al. |
| 2003/0219433 A1 | 11/2003 | Hansen et al. |
| 2003/0219818 A1 | 11/2003 | Bohen et al. |
| 2004/0082762 A1 | 4/2004 | Basi et al. |
| 2004/0093621 A1 | 5/2004 | Shitara et al. |
| 2004/0110704 A1 | 6/2004 | Yamane et al. |
| 2004/0131692 A1 | 7/2004 | Kreuter et al. |
| 2004/0132140 A1 | 7/2004 | Satoh et al. |
| 2004/0180417 A1 | 9/2004 | Seidah |
| 2004/0192898 A1 | 9/2004 | Jia et al. |
| 2004/0109865 A1 | 10/2004 | Niwa et al. |
| 2004/0110282 A1 | 10/2004 | Kanda et al. |
| 2004/0197324 A1 | 10/2004 | Liu et al. |
| 2004/0204354 A1 | 10/2004 | Nelson et al. |
| 2004/0248197 A1 | 12/2004 | Holtzman et al. |
| 2005/0014934 A1 | 1/2005 | Hinton et al. |
| 2005/0058644 A1 | 3/2005 | Engleman |
| 2005/0169925 A1 | 4/2005 | Bardroff et al. |
| 2005/0123546 A1 | 6/2005 | Umana et al. |
| 2005/0142133 A1 | 6/2005 | Lazar et al. |
| 2005/0147613 A1 | 7/2005 | Raso |
| 2005/0180972 A1 | 8/2005 | Wahl et al. |
| 2005/0260186 A1 | 11/2005 | Bookbinder et al. |
| 2006/0008883 A1 | 1/2006 | Lazar et al. |
| 2006/0104968 A1 | 5/2006 | Bookbinder et al. |
| 2006/0210557 A1 | 9/2006 | Luisi et al. |
| 2006/0251652 A1 | 11/2006 | Watkins et al. |
| 2007/0061900 A1 | 3/2007 | Murphy et al. |
| 2007/0098721 A1 | 5/2007 | Heinz et al. |
| 2008/0167449 A1 | 7/2008 | Lazar et al. |
| 2008/0275220 A1 | 11/2008 | Friess et al. |
| 2009/0162359 A1 | 6/2009 | Klein et al. |
| 2009/0252724 A1 | 10/2009 | Loetscher et al. |
| 2009/0263491 A1 | 10/2009 | Kreuter et al. |
| 2009/0297436 A1 | 12/2009 | Garcia-Martinez et al. |
| 2010/0016786 A1 | 1/2010 | Drews et al. |
| 2010/0077498 A1 | 3/2010 | Pardridge et al. |
| 2010/0081796 A1 | 4/2010 | Brinkmann et al. |
| 2010/0121036 A1 | 5/2010 | Fischer et al. |
| 2010/0129357 A1 | 5/2010 | Garcia-Martinez et al. |
| 2010/0190247 A1 | 7/2010 | Lazar et al. |
| 2010/0256338 A1 | 7/2010 | Brinkmann. et al. |
| 2010/0172907 A1 | 8/2010 | Bardroff et al. |
| 2011/0070225 A1 | 3/2011 | Goldbach et al. |
| 2012/0034160 A1 | 2/2012 | Ghayur et al. |
| 2012/0171120 A1 | 5/2012 | Dennis et al. |
| 2012/0141484 A1 | 7/2012 | Garcia-Martinez et al. |
| 2012/0244577 A1 | 9/2012 | Dixit et al. |
| 2013/0034554 A1 | 2/2013 | Garcia-Martinez et al. |
| 2013/0039925 A1 | 2/2013 | Bansal et al. |
| 2013/0045206 A1 | 2/2013 | Poul et al. |
| 2013/0078249 A1 | 3/2013 | Ast et al. |
| 2013/0090457 A1 | 4/2013 | Cunningham et al. |
| 2013/0136747 A1 | 5/2013 | Bardroff et al. |
| 2013/0315901 A1 | 11/2013 | Derosier et al. |

(56) References Cited

U.S. PATENT DOCUMENTS

| | | |
|---|---|---|
| 2014/0154254 A1 | 6/2014 | Kannan et al. |
| 2014/0212423 A1 | 7/2014 | Karaoglu-Hanzatian |
| 2014/0271459 A1 | 9/2014 | Dutzar |
| 2014/0271464 A1 | 9/2014 | Garcia-Martinez et al. |
| 2014/0271661 A1 | 9/2014 | Ye et al. |
| 2015/0030589 A1 | 1/2015 | Goldbach et al. |
| 2015/0125446 A1 | 5/2015 | Klein et al. |
| 2015/0132217 A1 | 5/2015 | Chang et al. |
| 2015/0140003 A1 | 5/2015 | Klauza et al. |
| 2015/0196663 A1 | 7/2015 | Shusta et al. |
| 2015/0266947 A1 | 9/2015 | Sierks |
| 2015/0315296 A1 | 11/2015 | Schaefer et al. |
| 2015/0322149 A1 | 11/2015 | Bohrmann et al. |
| 2015/0353639 A1 | 12/2015 | Watts et al. |
| 2016/0145348 A1 | 5/2016 | Stephan |
| 2018/0171012 A1 | 6/2018 | Sonoda et al. |
| 2018/0222992 A1 | 8/2018 | Duerr et al. |
| 2018/0222993 A1 | 8/2018 | Duerr et al. |
| 2018/0282408 A1 | 10/2018 | Dengl et al. |
| 2018/0291110 A1 | 10/2018 | Klein et al. |
| 2019/0276530 A1 | 9/2019 | Bohrmann et al. |
| 2020/0071413 A1 | 3/2020 | Rueger et al. |
| 2020/0216554 A1 | 7/2020 | Duerr et al. |
| 2022/0144963 A9 | 5/2022 | Duerr et al. |

FOREIGN PATENT DOCUMENTS

| | | |
|---|---|---|
| CL | 2016/207240 A1 | 12/2016 |
| CL | 201703351 | 12/2017 |
| CL | 201800819 | 3/2018 |
| CL | 2017003207 A1 | 6/2018 |
| CN | 102740888 A | 10/2012 |
| CN | 102741282 A | 10/2012 |
| CO | 2017012416 A2 | 2/2018 |
| CO | 2018000235 A2 | 3/2018 |
| CO | 2018003452 A2 | 6/2018 |
| EP | 0332865 A2 | 9/1989 |
| EP | 0683234 | 1/1994 |
| EP | 0 425 235 B1 | 9/1996 |
| EP | 0330191 B1 | 10/1996 |
| EP | 1125905 | 8/2001 |
| EP | 2343086 A1 | 7/2011 |
| EP | 2 668 901 A1 | 12/2013 |
| EP | 2 708 560 A1 | 3/2014 |
| EP | 2708560 A1 | 3/2014 |
| EP | 2787078 A1 | 8/2014 |
| FR | 2953841 | 12/2009 |
| FR | 2 953 841 A1 | 6/2011 |
| JP | 2014-506258 A | 3/2014 |
| JP | 2017187722 | 10/2017 |
| JP | 2018516811 A | 6/2018 |
| RU | 2 439 160 C1 | 1/2012 |
| UA | 201002186 | 5/2010 |
| WO | 90/08187 A1 | 7/1990 |
| WO | 90/11294 A1 | 10/1990 |
| WO | 91/01133 A1 | 2/1991 |
| WO | WO91/11520 | 8/1991 |
| WO | 93/10819 A1 | 6/1993 |
| WO | 0307434 B1 | 9/1993 |
| WO | 93/21232 A1 | 10/1993 |
| WO | 93/25673 A1 | 12/1993 |
| WO | 94/11026 A2 | 5/1994 |
| WO | 94/29351 A2 | 12/1994 |
| WO | 95/03770 A1 | 2/1995 |
| WO | 95/15769 | 6/1995 |
| WO | 96/07321 A1 | 3/1996 |
| WO | 96/20218 | 7/1996 |
| WO | 96/25088 | 8/1996 |
| WO | 96/39628 | 12/1996 |
| WO | 97/04801 A1 | 2/1997 |
| WO | 97/08320 | 3/1997 |
| WO | 0340109 B1 | 5/1997 |
| WO | 97/30087 A1 | 8/1997 |
| WO | 98/56418 A1 | 12/1998 |
| WO | 98/58964 A1 | 12/1998 |
| WO | 99/22764 A1 | 5/1999 |
| WO | 99/27944 | 6/1999 |
| WO | 99/51642 A1 | 10/1999 |
| WO | 00/09160 A1 | 2/2000 |
| WO | 00/20864 A1 | 4/2000 |
| WO | 2000/23472 A2 | 4/2000 |
| WO | 00/27428 A1 | 5/2000 |
| WO | 00/27433 A1 | 5/2000 |
| WO | 00/42072 A2 | 7/2000 |
| WO | 00/44788 A1 | 8/2000 |
| WO | 00/61739 A1 | 10/2000 |
| WO | 00/61768 | 10/2000 |
| WO | 00/64482 A1 | 11/2000 |
| WO | 00/67795 A1 | 11/2000 |
| WO | 00/67796 A1 | 11/2000 |
| WO | 00/72880 | 12/2000 |
| WO | 00/74718 A1 | 12/2000 |
| WO | 00/76542 A1 | 12/2000 |
| WO | 00/77178 | 12/2000 |
| WO | 01/03734 A1 | 1/2001 |
| WO | 01/10460 A1 | 2/2001 |
| WO | 01/10461 A1 | 2/2001 |
| WO | 01/10462 A1 | 2/2001 |
| WO | 01/13945 A1 | 3/2001 |
| WO | 01/29246 | 4/2001 |
| WO | 01/34194 A1 | 5/2001 |
| WO | 01/39796 | 6/2001 |
| WO | 01/72333 A1 | 10/2001 |
| WO | 01/77342 A1 | 10/2001 |
| WO | 01/74388 A1 | 11/2001 |
| WO | 01/80884 A1 | 11/2001 |
| WO | 01/97858 A2 | 12/2001 |
| WO | 02/02597 A2 | 1/2002 |
| WO | 02/04021 A1 | 1/2002 |
| WO | 02/031140 A1 | 4/2002 |
| WO | 02/34790 A1 | 5/2002 |
| WO | 02/46237 | 6/2002 |
| WO | 02/060955 A2 | 8/2002 |
| WO | 02/064734 | 8/2002 |
| WO | 02/079255 A1 | 10/2002 |
| WO | 02/088306 | 11/2002 |
| WO | 02/088307 | 11/2002 |
| WO | 02/096937 | 12/2002 |
| WO | 02/096948 A2 | 12/2002 |
| WO | 02/102312 A2 | 12/2002 |
| WO | 03/002607 A1 | 1/2003 |
| WO | 03/009817 A2 | 2/2003 |
| WO | 03/011878 A2 | 2/2003 |
| WO | 03/016466 A2 | 2/2003 |
| WO | 03/049694 A2 | 6/2003 |
| WO | 03/061694 A1 | 7/2003 |
| WO | 03/068821 A2 | 8/2003 |
| WO | 03/070760 A2 | 8/2003 |
| WO | 03/084570 A1 | 10/2003 |
| WO | 03/085107 A1 | 10/2003 |
| WO | 03/085119 | 10/2003 |
| WO | 2004/149553 A3 | 2/2004 |
| WO | 2004/032828 A2 | 4/2004 |
| WO | 2004/032868 | 4/2004 |
| WO | 2004/035607 A2 | 4/2004 |
| WO | 2004/056312 A2 | 7/2004 |
| WO | 2004/1034044 A1 | 12/2004 |
| WO | 2005/035578 A1 | 4/2005 |
| WO | 2005/035586 A1 | 4/2005 |
| WO | 2005/053742 A1 | 6/2005 |
| WO | 2005092925 A3 | 6/2005 |
| WO | 2005/100402 A1 | 10/2005 |
| WO | 2005/116220 A1 | 12/2005 |
| WO | 2006/029879 A2 | 3/2006 |
| WO | 2006/044908 | 4/2006 |
| WO | 2006/081587 A2 | 8/2006 |
| WO | 2006/083689 A2 | 8/2006 |
| WO | 2006/131013 A2 | 12/2006 |
| WO | 2007/044323 A2 | 4/2007 |
| WO | 2007/044323 A3 | 4/2007 |
| WO | 2007/068429 A1 | 6/2007 |
| WO | 2007/0684429 A1 | 6/2007 |
| WO | 07/110152 | 10/2007 |
| WO | 2007/110339 A1 | 10/2007 |

(56) References Cited

FOREIGN PATENT DOCUMENTS

| | | |
|---|---|---|
| WO | 2008/005847 A2 | 1/2008 |
| WO | 2008/022349 A2 | 2/2008 |
| WO | 2008/022349 A3 | 2/2008 |
| WO | 2008/025527 | 3/2008 |
| WO | 2008/039944 A2 | 4/2008 |
| WO | 2008/063771 | 5/2008 |
| WO | 2008/071394 A1 | 6/2008 |
| WO | 2008/077546 A1 | 7/2008 |
| WO | 2009/018411 | 2/2009 |
| WO | 2009/126616 A2 | 10/2009 |
| WO | 2010033587 A2 | 3/2010 |
| WO | 2010/102251 A2 | 9/2010 |
| WO | 2010/115551 A1 | 10/2010 |
| WO | 2010/115553 A1 | 10/2010 |
| WO | 2011/066369 A2 | 6/2011 |
| WO | 2011/066371 A2 | 6/2011 |
| WO | 2011/073943 A1 | 6/2011 |
| WO | 2011/116387 A1 | 9/2011 |
| WO | 2012/075037 A1 | 6/2012 |
| WO | 2012/087835 A3 | 6/2012 |
| WO | 2012/093125 A1 | 7/2012 |
| WO | 2012/096924 A1 | 7/2012 |
| WO | 2012/130831 A1 | 10/2012 |
| WO | 2012/143379 A1 | 10/2012 |
| WO | 2012/153707 A1 | 11/2012 |
| WO | 2013012733 A1 | 1/2013 |
| WO | 2013/025853 A1 | 2/2013 |
| WO | 2013/026831 A1 | 2/2013 |
| WO | 2013/038156 1 | 3/2013 |
| WO | 2013/039471 A1 | 3/2013 |
| WO | 2013/079174 A1 | 6/2013 |
| WO | 2013/113615 A1 | 8/2013 |
| WO | 2013/127816 | 9/2013 |
| WO | 2013/131866 A1 | 9/2013 |
| WO | 2013/177062 A2 | 11/2013 |
| WO | 2014/033074 A1 | 3/2014 |
| WO | 2014/039855 | 3/2014 |
| WO | 2014/047231 A1 | 3/2014 |
| WO | 2014/052188 A1 | 4/2014 |
| WO | 2014/081955 A1 | 5/2014 |
| WO | WO2014081955 A1 | 5/2014 |
| WO | 2014/082179 A1 | 6/2014 |
| WO | 2014/089209 A3 | 6/2014 |
| WO | 2014/131694 A1 | 9/2014 |
| WO | 2014/131711 A1 | 9/2014 |
| WO | 2014/153114 A1 | 9/2014 |
| WO | 2014/183973 | 11/2014 |
| WO | 2014/189973 A2 | 11/2014 |
| WO | 2015/014884 A1 | 5/2015 |
| WO | 2015-063339 | 5/2015 |
| WO | 2015/095392 A1 | 6/2015 |
| WO | 2015/101588 A1 | 7/2015 |
| WO | 2015-528452 A | 9/2015 |
| WO | 2016/020309 A1 | 2/2016 |
| WO | 2016/086189 | 6/2016 |
| WO | 2016/160032 A1 | 10/2016 |
| WO | 2016/207091 A1 | 12/2016 |
| WO | 2016/207240 A1 | 12/2016 |
| WO | 2016/208695 A1 | 12/2016 |
| WO | 2017/055540 A1 | 4/2017 |
| WO | 2017/055542 A1 | 4/2017 |

OTHER PUBLICATIONS

Pardridge, W.M. et al., "Drug transport across the blood-brain barrier" J Cerebral Blood Flow Metab 32:1959-1972 ( 2012).

Ridgway et al., "Knobs-into-holes' engineering of antibody CH3 domains for heavy chain heterodimerization" Protein Engineering 9(7):617-621 ( 1996).

Yu et al., "Boosting brain uptake of a therapeutic antibody by reducing its affinity for a transcytosis target" Science Translational Med 3(84):84ra44 (May 25, 2011).

Yu, J.Y. et al., "Developing Therapeutic Antibodies for Neurodegenerative Disease" Neurotherapeutics 10(3):459-472 (Apr. 3, 2013).

(International Search Report on patentability for International Patent Application No. PCT/EP2014/079353), dated Sep. 20, 2015, 6 pages.

(Written Opinion of the International Searching Authority for International Patent Application No. PCT/EP2014/079353), dated Sep. 20, 2015, 8 pages.

Comoglio, P. et al., "Drug development of MET inhibitors: targeting oncogene addiction and expedience" Nature 73:504-516 (Jun. 2008).

Di Zenzo, G. et al., "The Intracellular and Extracellular Domains of BP180 Antigen Comprise Novel Epitopes Targeted by Pemphigoid Gestationis Autoantibodies" J. of Investigative Dermatology 127:864-873 (Mar. 19, 2006).

Lu, D. et al., "Acquired antagonistic activity of a bispecific diabody directed against two different epitopes on vascular endothelial growth factor receptor 2" J. of Immunological Methods 230:159-171 ( 1999).

Pakula, A. et al., "Genetic Analysis of Protein Stability and Function" Annu. Rev. Genet. 23:189-310 ( 1989).

Weisser, N., et al., "Applications of single-chain variable fragment antibodies in therapeutics" Biotechnol Adv 27(4):502-520 (Jul. 31, 2009).

Bien-Ly et al., "Transferrin receptor (TfR) trafficking determines brain uptake of TfR antibody affinity variants" J. Exp. Med. 211(2):233-244 (2014).

Klein C. et al., "Progress in overcoming the chain association issue in bispecific heterodimeric IgG antibodies" MAbs 4(6):653-663 (Jan. 11, 2012).

Lode, H.N., et al., "Targeted therapy with a novel enediyne antibiotic calicheamicin V11 effectively suppressess growth and dissemination of liver metastasis in aa syngeneic model of murine neuroblastoma" Cancer Res 58(14):2925-2928 (Jul. 15, 1998).

Looney, R. J., "Treating human autoimmune disease by depleting B cell" Ann Rheum Dis 61(10):863-866 (Oct. 1, 2002).

Martin and Chan et al., "Pathogenic roles of B cells in human autoimmunity; insights from the clinic" Immunity 20(5):517-527 (May 2004).

Niewoehner, J., et al., "Increased Brain Penetration and Potency of a Therapeutic Antibody Using a Monovalent Molecular Shuttle" Neuron 81(1):49-60 (Jan. 8, 2014).

Offner, H. et al., "T cell receptor peptide therapy triggers autoregulation of experimental encephalomyelitis" Science 251(4992):430-432 (Jan. 25, 1991).

Okazaki et al., "Fucose depletion from human IgG1 oligosaccharide enhances binding enthalpy and association rate between IgG1 and FegammaRIIIa" J Mol Biol 336(5):1239-1249 (Mar. 5, 2004).

O'Nuallain, B. et al., "Conformational Abs recognizing a generic amyloid fibril epitope" PNAS 99(3):1485-1490 (2002).

Paul, William E., "Fundamental Immunology" Raven Press( SUPPL Chpt. 8):292-295 (1993).

Perotta, A., et al., "Response of Chronic Relapsing ITP of 10 years duration to Rituximab" Blood (Abstract #3360; Part 1-2), 92(10 SUPPL 1):88b (Nov. 15, 1998).

Perotta, A., et al., "Rituxan in the Treatment of Chronic Idiopathic Thrombocytopenic" Blood (Abstract #49), 94 (14):4a ( 1999).

Pestronk, A., et al., "Treatment of IgM antibody associated polyneuropathies using rituximab" J Neurol Neurosurg Psychiatry 74(4):485-489 (Apr. 1, 2003).

Pranzatelli, M., et al., "CSF B-Cell Over-Expansion in Paraneoplastic Opsoclonus-Myoclonus: Effect of Rituximab, an Anti-B-Cell Monoclonal Antibody" Neurology (Abstract #P05.128), 60 (5 SUPPL suppl 1):A395 (Mar. 2003).

Press et al., "Monoclonal antibody 1F5 (Anti-CD20) serotherapy of human B cell lymphomas" Blood 69(2):584-591 ( 1987).

Raju, T., "Glycosylation variations with expression systems and their impact on biological activity of therapeutic immunoglobulins" Bioprocess INTL 1:44-53 (Apr. 1, 2003).

Ratanatharathorn, V., et al., "Anti-CD20 chimeric monoclonal antibody treatment of refractory immune-mediated thrombocytopenia in a patient with chronic graft-verus-host disease" Ann Intern Med 133(4):275-279 (Aug. 15, 2000).

Reff, M., et al., "Depletion of B cells in vivo by a chimeric mouse human monoclonal antibody to CD20" Blood 83(2):435-445 (Jan. 15, 1994).

(56) References Cited

OTHER PUBLICATIONS

Routier, F., et al., "The glycosylation pattern of a humanized IgGI antibody (D1.3) expressed in CHO cells" Glycoconjugate J 14(2):201-207 (Feb. 1, 1997).
Rudikoff et al., "Single amino acid substitiution altering antigen-binding specificity" P NATL ACAD SCI USA 79:1979-1983 (Mar. 1982).
Saleh, M., et al., "A pilot study of the anti-CD20 monoclonal antibody rituximab in patients with refractory immune thrombocytopenia" Semin Oncol 27(6 SUPPL Supp 12):99-103 (Dec. 1, 2000).
Schaefer, W., et al., "Immunoglobulin domain crossover as a generic approach for the production of bispecific IgG antibodies" PNAS USA 108(27):11187-11192 (Jul. 5, 2011).
Schier et al., "Isolation of picomolar affinity anti-c-erbB-2 single-chain Fv by molecular evolution of the complementarity determining regions in the center of the antibody binding site" Journal of Molecular Biology 263(4):551-567 (Nov. 8, 1996).
Sheeley et al., "Characterization of Monoclonal Antibody Glycosylation: Comparison of Expression Systems and Identification of Terminal α-Linked Galactose" Analytical Biochemistry 247:102-110 (1997).
Silverman and Weisman et al., "Rituximab therapy and autoimmune disorders: prospects for anti-B cell therapy" Arthritis Rheum 48(6):1484-1492 (Jun. 2003).
Lim, Y. et al., "Engineering mammalian cells in bioprocessing—current achievements and future perspectives" Biotechnol. Appl. Biochem. 55:175-189 ( 2010).
Lloyd, C., et al., "Modelling the human immune response: performance of a 1011 human antibody repertoire against a broad panel of therapeutically relevant antigens" Protein Eng Des Sel 22(3):159-168 (Mar. 1, 2009).
Lo et al. et al., "High level expression and secretion of Fc-X fusion proteins in mammalian cells" Protein Eng 11(6):495-500 ( 1998).
Lonberg N., "Human antibodies form transgenic animals" Nat Biotechnol 23(9): 1117-11125 ( 2005).
Longberg, N.,, "Fully human antibodies from transgenic mouse and phage display platforms" Curr Opin Immunol 20(4):450-459 (Aug. 1, 2008).
Lukas, T. J., et al., "Inhibition of C1-mediated immune hemolysis by monomeric and dimeric peptides from the second constant domain of human immunoglobulin G" J Immunol 127(6):2555-2560 (Dec. 1, 1981).
Lund, J., et al., "Oligosaccharide-protein interactions in IgG can modulate recognition by Fc gamma receptors" FASEB J. 9(1):115-119 (Jan. 1, 1995).
MacCallum, R., et al., "Antibody-antigen Interactions: Contact Analysis and Binding Site Topograpgy" J Mol Biol 262(5):732-745 (Oct. 11, 1996).
Mather, J., "Establishment and Characterization of Two Distinct Mouse Testicular Epithelial Cell Lines" Biol Reprod 23:243-252 ( 1980).
Mather, J., et al., "Culture of Testicular Cells in Hormone-Supplemented Serum-Free Medium" Ann Ny Acad Sci 383:44-68 ( 1982).
Meder et al., Journal of Cell Biology 168(2):303-313 ( 2005).
Merchant et al., "An efficient route to human bispecific IgG" Nat Biotechnol 16(7):677-681 (Jul. 1, 1998).
Morgan, A, et al., "The N-terminal end of the CH2 domain of chimeric human IgG1 anti-HLA DR is necessary for C1q, Fc gamma RI and Fc gamma RIII binding" Immunology 86(2):319-324 (Oct. 1, 1995).
Morrison, S., et al., "Chimeric human antibody molecules: Mouse antigen-binding domains with human constant region domains" PNAS 81(21):6851-6855 (Nov. 1, 1984).
Nagy, A., et al., "Stability of cytotoxic luteinizing hormone-releasing hormone conjugate (AN-152) containing doxorubicin 14-O hemiglutarate in mouse and human serum in vitro: implications for the design of preclinical studies" PNAS USA 97(2):829-834 (Jan. 18, 2000).
Nestler et al., Molecular Neuropharmacology (Chapter 8),:199, 211-219 ( 2009).
Ni et al., "Research progress and future perspectivies in antibodomics and antibodomic drugs" Xiandai Mianyixue ((Abstract only)), 26(4):265-268 ( 2006).
Office Action issued by Canadian Patent Office, dated Oct. 31, 2011, in related Canadian Patent Appl. No. 2632828.
Office Action issued by the Chilean Patent Office, dated Dec. 11, 2006, in related Chilean Appl. No. 3436-2006.
Office Action issued by the Colobian Patent Office in Application No. 2008 049920-A, dated Sep. 6, 2012.
Office Action issued by the Malaysian Patent Office in Application No. PI 20081349, dated Nov. 14, 2012.
Office Action issued by the Zealand Patent Office, dated Apr. 13, 2010, in related New Zealand Patent Appl. No. 068241.
Osbourn, J. et al., "From rodent reagents to human therapeutics using antibody guided selection" Methods 36(1):61-68 (May 1, 2005).
Osol, A. Remington's Pharmaceutical Sciences 16 edition, ( 1980).
Pace, C., et al., "How to measure and predict the molar absorption coefficient of a protein" Protein SCI 4(11):2411-2423 (Nov. 1, 1995).
Padlan, E., "A possible procedure for reducing the immunogenicity of antibody variable domains while preserving their ligand-binding properties" Mol Immunol 28(4-5):489-498 (Apr. 30, 1991).
Pardridge, W., et al., "Blood--brain barrier drug delivery of IgG fusion proteins with a transferrin receptor monoclonal antibody" Expert Opin Drug Del 12(2):207-222 (Feb. 1, 2015).
Paul et al., Fundamental Immunology, 3rd ed. Raven Press, NY, Chap. 9, p. 292-295.
Penichet and Morrison et al. Wiley Encyclopedia of Molecular Medicine (Section: Chimeric, Humanized and Human Antibodies), John Wiley & Sons Inc., New York:John Wiley,:214-216 ( 2002).
Perlman et al., The Journal of Clinical Endocrinology & Stimulating Hormone 88(7):3227-3235 ( 2003).
Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).
Portolano, S., et al., "Lack of promiscuity in autoantigen-specific H and L chain combinations as revealed by human H and L chain 'roulette'" J Immunol 150(3):880-887 (Feb. 1, 1993).
Press, O., et al., "Monoclonal Antibody 1F5 (Anti-CD20) Serotherapy of Human B Cell Lymphomas" Blood 69(2):584-591 (Feb. 1, 1987).
Presta, L., et al., "Humanization of an Antibody Directed Against IgE" J Immunol 151(5):2623-2632 (Sep. 1, 1993).
Price et al., "Genetic Neurodegenerative Diseases: The Human Illness and Transgenic Models" Science 282(5391):1079-1083 ( 1988).
Queen, C., et al., "A humanized antibody that binds to the interleukin 2 receptor" PNAS USA 86(24):10029-10033 (Dec. 1, 1989).
Ravetch and Kinet et al., "Fc receptors" Ann. Rev. Immunol. 9:457-492 ( 1991).
Ravetch, J. et al., "IgG Fc Receptors" Ann Rev Immunol 19:275-290 ( 2001).
Richards et al., "PS2APP Transgenic Mice, Coexpressing hPS2mut and hAPPswe, Show Age-Related Cognitive Deficits Associated with Discrete Brain Amyloid Deposition and Inflammation" Journal of Neuroscience 23(26):8989-9003 ( 2003).
Riechmann, L.,, "Reshaping human antibodies for therapy" Natue 332(6162):323-327 (Mar. 24, 1988).
Ripka, J., et al., "Two chinese hamster ovary glycosylation mutants affected int he conversion of GDP-Mannose to GDP-fucose" Arch Biochem Biophys 249(2):533-545 (Sep. 1, 1986).
Rosok, M., et al., "A combinatorial library strategy for the rapid humanization of anticarcinoma BR96 Fab" J Biol Chem 271(37):22611-22618 (Sep. 13, 1996).
Rudikoff, S., et al., "Single amino acid substitution altering antigen-binding specificity" PNAS USA 79(6)1979-1983 (Mar. 1, 1982).
Sambrook et al. Molecular Cloning: A Laboratory Manual Second edition, New York:Cold Spring Harbor Laboratory Press, ( 1989).

(56) References Cited

OTHER PUBLICATIONS

Schneider, C., et al., "Primary structure of human transferring receptor deduced from the mRNA sequence" Nature 311(5987):675-678 (Oct. 18, 1984).
Seidah et al., Biochem. J, 314:951-960 ( 1996).
Selkoe, "Cell Biology Of The Amyloid-Protein Precursor and The Mechanism Of Alzheimer's Disease" Annual Rev. Cell Biol. 10:373-403 ( 1994).
Shen-Xin et al., "Study on in vitro anti-tumor effect of anti-human transferrin receptor monoclonal antibody" Chin. J. Cell Mol Immunol (EN-Abstract), 24(2):144-146 ( 2008).
Shields et al., "High Resolution Mapaping of the Binding Site on Human IgG1 for FcγRI, FcγRII, FcγRIII, and FcRN and Design of IgG1 Variants with Improved Binding to the FcγR" J Biol Chem 276(9):6591-6604 ( 2001).
Sims, M., et al., "A Humanized CD18 Antibody Can Block Function Without Cell Destruction" J Immunol 151(4):2296-2308 (Aug. 15, 1993).
Singapore Examination Report issued by the Danish Patent Office, dated Jan. 13, 2011, in Appl. No. 200803302-9.
Singapore Written Opinion and Search Report issued by the Danish Patent Office, dated Feb. 10, 2010, in Appl. No. 200803302-9.
Sinha et al., "Cellular mechanism of b-amyloid production and secretion" PNAS 96:11049-11053 ( 1999).
Sisodia, "B-Amyloid precursor protein cleavage by a membrane-bound protease" PNAS 89:6075-6079 ( 1992).
Solomon et al., "Activity of monoclonal antibodies in prevention of in vitro aggregation of their antigens" Stability and Stabilization of Biocatalysts:183-188 ( 1998).
Solomon et al., "Disaggregation of Alzheimer b-amyloid by site-directed mAb" PNAS 94:4109-4112 ( 1997).
Solomon et al., "Monoclonal antibodies inhibit in vitro fibrillar aggregation of the Alzheimer B-amyloid peptide" PNAS 93:452-455 ( 1996).
Solomon et al., "Vaccination for The Prevention and Treatment of Alzheimer's Disease" Drugs of Today 36(9):655-663 ( 2000).
Somer et al. et al., "Improvement in Sjogren's syndrome following therapy with rituximab for marginal zone lymphoma" Arthritis Rheum 49(3):394-398 (Jun. 15, 2003).
Specks, U., et al., "Response of Wegener's Granulomatosis to anti-CD20 chimeric monoclonal antibody therapy" Arthritis Rheum 44(12):2836-2840 (Dec. 1, 2001).
Spiess, C., et al., "Alternative molecular formats and therapuetic applications for bispecific antibodies" Mol Immunol 67(SUPPL 2 Pt A):95-106 (Jan. 27, 2015).
Stahl, H., et al., "Rituimab in RA: Efficacy and safety from a randomised, controlled trial" Ann Rheum Dis 62(SUPPL Suppl 1) ( 2003).
Stasi, R., et al., "Rituximab chimeric anti-CD20 monoclonal antibody treatment for adults with chronic idiopathic thromboyctopenic purpura" Blood 98(4):952-957 (Aug. 15, 2001).
Stockinger, H., et al. Current Protocols in Immunology "Appendix: Monoclonal Antibodies to Human Cell Surface Antigens" New York, NY -US:John Wiley & Sons, vol. 53(1):A,4A, 1-A,4A.49 (May 15, 2003).
Sumbria, R., et al., "Disaggregation of Amyloid Plaque in Brain of Alzheimer's Disease Transgenic Mice with Daily Subcutaneous Administration of a Tetravelent Bispecific Antibody That Targets the Transferrin Receptor and the Abeta Amyloid Peptide" Mol Pharm 10(9):3507-3513 (Sep. 3, 2013).
Tedder, T., et al., "The B Cell Surface Molecule B1 is functionally Linked with B Cell Activation and Differentiation" J Immunol 135(2):973-979 (Aug. 1, 1985).
Tedder, T., et al., "The CD20 Surface Molecule of B Lymphocytes Functions as a Calcium Channel" J Cell Biochem (Abstract #M 023), 14D:195 ( 1990).
Teeling, J et al., "Characterization of new human CD20 monoclonal antibodies with potent cytolytic activity against non-Hodgkin lymphomas" Blood 104(6):1793-1800 (Sep. 15, 2004).

The Brazilian Preliminary Office Action, dated Nov. 5, 2020, in the related Brazilian Appl. No. BR112018004828-3.
The Brazilian Preliminary Office Action, dated Nov. 5, 2020, in the counter-related Brazilian Appl. No. BR112018004733-3.
The English translation of the Chinese Office Action, dated Nov. 3, 2020, in the related Chinese Patent application No. 201680037169.1.
The English translation of the Russian Office Action, dated Mar. 27, 2020, in the related Russian Patent Appl. No. 2018113507/10(021205).
The English translation of the Ukrainian Office Action, dated Sep. 9, 2020, in the related Ukrainian Patent application No. a 201800597.
The European Office Action, dated Oct. 12, 2020, in the related European Patent Appl. No. 16 774 687.4.
Thommesen, J., et al., "Lysine 322 in the human IgG3 C(H)2 domain is crucial for antibody dependent complement activation" Mol Immunol 37(16):995-1004 (Nov. 1, 2000).
Thiroem Nibickibak Antibodies 84: Biological and Clinical Applications A. Pinchera, G. Doria, F. Dammacco & Bargellesi,Editrice Kurtis s.r.l. (Publisher),;475-506 ( 1985).
Thorpe, P. et al., "The Preparation And Cytotoxic Properties Of Antibody-Toxin Conjugates" Immunol Rev 62(1):119-158 (Feb. 1, 1982).
Tobinai et al., "A Review of Obinutuzumab (GA101), a Novel Type II Anti-CD20 Monoclonal Antibody, for the Treatment of Patients with B-Cell Malignancies" Adv Ther 34:324-356 ( 2017).
Torgov, M., et al., "Generation of an intensely potent anthracycline by a monoclonal antibody--β-gakactosidase conjugate" Bioconjugate Chem 16(3):717-21 (May 1, 2005).
Torres, M., et al., "The immunoglobulin constant region contributes to affinity and specificity" Trends Immunol 29(2):91-97 (Feb. 1, 2008).
Tuscano et al., "Successful treatment of Infliximab-refractory rheumatoid arthritis with rituximab"Poster (Presentation #LB11, Poster #444, from Oasis—Online Abstract Submission and Invitation System) Annual Scientific Meeting of the American College of Rheumatology, New Orleans, LA US, ( Oct. 24-29,2002).
Urlaub, G., et al., "Isolation of Chinese hamster cell mutants deficient in dihydrofolate reductase activity" PNAS USA 77(7):4216-4220 (Jul. 1980).
Valentine et al., "B3.9 Structure and function of the B-cell specific 35-37 kDa CD20 protein" Leukocyte Typing III (B-cell antigens—papers),:440-443 ( 1987).
Valenttine, M., et al., "Phossphorylation of the CD20 Phosoporetein in Resting B Lymphocytes"J Biol Chem 264(19):11282-11287 (Jul. 5, 1989).
Van De Winkel, J.G. et al., "Biology of human immunoglobulin G Fc receptors" J Leukocyte Biol 49(5):511-524 (May 1, 1991).
Van Dijk and Van De Winkel et al., "Human antibdies as next generation therapeutics" Curr Opin Chem Biol 5(4):368-374 (Aug. 2001).
Virgolini, L., et al., "Rituximab in autoimmune diseases" Biomed Pharmacother 58(5):299-309 (Jun. 1, 2004).
Vitetta et al., "Redesigning nature's poissions to create anti-tumor reagents" Science 238:1098-1104 ( 1987).
Vollmers, H., et al., "The 'early birds': Natural IgM antibodies and immune srveillance" Histol Histopathol 20(3):927-937 (Jul. 1, 2005).
Vollmers, H., "Death by stress: natural IgM-induced apoptosis" Methods Find Exp Clin Pharmacol 27(3):185-191 (Apr. 1, 2005).
Von Bundingen, H., et al., "B cells in multiple sclerosis: connecting the dots" Curr Opin Immunol 23(6):713-720 (Dec. 1, 2011).
Wagner et al., "Modulation of amyloid β protein precursor processing as a means of retarding progression of Alzheimer's disease" J. Clin. Invest. 104(10):1329-1332 ( 1999).
Wagner, E., et al., "Transferrin-Polycation Conjugates as Carriers for DNA Uptake Into Cells" PNAS USA 87(9):3410-3414 (Mat 1, 1990).
Weide, R., et al., "Successful long-term treatment of systemic lupus erythematosus with rituximab maintenance therapy" Lupus 12(10):779-782 ( 2003).
Weissmiller et al., Translational Nerodegeneration 1(14):1-9 ( 2012).
Who Drug Information, vol. 26, No. 4, 2012 p. 401.

(56) References Cited

OTHER PUBLICATIONS

Wright, A., et al., "Effect of glycosylation on antibody function: Implication for genetic engineering" Trends Biotechnol 15(1):26-32 (Jan. 1, 1997).
Written Opinion of the International Searching Authority PCT/EP2016/073411 dated Dec. 13, 2016.
Wu, G.Y. and C. H. Wu., "Receptor-Mediated in Vitro Gene Transformation by Soluble DNA Carrier System" J Biol Chem 262(10):4429-4432 (Apr. 5, 1987).
Wylam, M., et al., "Successful treatment of refractory myasthenia gravis using rituximab: a pediatric case report" J Pediatr 143(5)674-677 (Nov. 1, 2003).
Yamane-Ohnuki, N., et al., "Establishment of FUT8 knockout Chinese hamster ovary cells: an ideal host cell line for producing completely defucosylated antibodies with enhanced antibody-dependent cellular cytotoxcity" Biotechnol Bioeng 87(5):614-622 (Sep. 5, 2004).
Yazaki, P. J., et al. Methods in Molecular Biology "Expression of recombinant antibodies in mammalian cell lines" Lo, B.K.C. (ed.), Totowa, NJ:Humana Press, vol. 248:255-268 ( 2004).
Yu, Y.J., et al., "Therapeutic bispecific antibodies cross the blood-brain barrier in nonhuman primates" SCI Transl Med 6(261):1-11 (Nov. 5, 2014).
Zaja, F., et al., "B-cell depletion with rituximab as treatment for immune hemolytic anemia and chronic thrombocyopenia"Haematologica 87(2):189-195 (Feb. 1, 2002).
Zaja, F., et al., "Efficacy and safety of rituximab in type II mixed cryoglobulinemia"Blood 101(10):3827-3834 (May 15, 2003).
Zaja, F., et al., "Rituximab for myasthenia gravis developing after bone marrow transplant" Neurology 55(7):1062-1063 (Oct. 10, 2000).
Zaja, F., et al., "Rituximab in case of cold agglutinin disease" Br J Haematol 115(1):232-233 (Oct. 1, 2001).
Zhang J. et al., "Design and optimization of a linker for fusion proteinc onstruction" Progress in Natural Science 19(10):1197-1200 ( 2009).
(Author Not Identified) Remingont's Pharmaceutical Sciences (Table of Contents, total in 4 pages), OSL et al., 16th edition, Easton, Pennsylvania:Mack Publishing Company, ( 1980).
"ACT™ Non-radioactive cytotoxicity assay for flow cytometry (CellTechnology, Inc. Mountain View, CA)":6.
Acton R & D Systems Glial Cell Line-Derived Neurotrophic Factors : Advances in Research and Application 2011 Edition ( 1996).
Ales Berlec et al., "Current state and recent advances in biopharmaceutical production in *Escherichia coil* , yeasts and mammalian cells" Journal of Industrial Microbiology & Biotechnology 40:257-274 ( 2013).
Almagro, J., et al., "Humanization of antibodies" Front Biosci 13:1619-1633 (Jan. 1, 2008).
Anderson, K. et al., "Expression of Human B Cell-Associated Antigens on Leukemias and Lymphomas: A Model of Human B Cell Differentiation" Blood 63(6):1424-1433 (Jun. 1, 1984).
Anderson, W. et al., "Human Gene Therapy" Science 256(5058):808-813 (May 8, 1992).
Arai, R. et al., "Design of the linkers which effectively separate domains of a bifunctional fusion protein" Protein Engineering 14(8):529-532 ( 2001).
Armour, K., et al., "Recombinant Human IgG Molecules Lacking Feγ Receptor I Binding and Moncyte Triggering Activites" Eur J Immunol 29(8):2613-2624 (May 10, 1999).
Arnon, R. et al. Monoclonal Antibodies and Cancer Therapy "Chapter 3: Immunotherapy-Monoclonal Antibodies for Immunotargeting of Drugs in Cancer Therapy" (Proceedings of the Roche-UCLA Symposium; Park City, Utah-US, 26 Jan.-Feb. 2, 1985), Reisfeld, R., and Sell, S., eds, New York, NY -US:Alan R. Liss, Inc.,:243-256 ( 1985).
Arzoo, K., et al., "Treatment of refractory antibody mediated autoimmune disorders with an anti-CD20 monoclonal antibody (rituximab)" Ann Rheum Dis 61(10):922-924 (Oct. 1, 2002).

Auner, H., et al., "Restoration of eryhropoiesis by rituximab in an adult patient with primary acquired pure red cell aplasia refractory to conventional treatment" BR J Haematol 116(3):727-728 (Mar. 1, 2002).
Baca, M., et al., "Antibody humanization using monovalent phage display" J Biol Chem 272(16):10678-10684 (Apr. 18, 1997).
Bauduer, F., et al., "Rituximab: a very efficient therapy in cold agglutinins and refractory autoimmune haemolytic anaemia associated with CD20-positive, low-grade non-Hodgkin's lymphoma" BR J Haematol 112(4):1085-1086 (Mar. 2001).
Berenstein, S., et al., "Favourable response to therapy with the anti-CD20 monoclonal antibody rtuximab in primary chronic cold agglutinin disease" BR J Haematol 115(1):79-83 (Oct. 1, 2001).
Berentsen, S., et al., "Rituximab for primary chronic cold agglutinin disease: a prospective study of 37 courses of therapy in 27 patients" Blood 103(8):2925-2928 (Apr. 15, 2004).
Biotechnology ((Russian)), 3:3-8 ( 2000).
Boerner, P., et al., "Production of antigen-specific human monoclonal antibodies from in vitro-primed human splenocytes" J Immunol 147(1):86-95 (Jul. 1, 1991).
Bonifacino, J., et al., "Commonly Used Techniques: Molecular Biology Techniques" Curr Protocols in Cell Biol 8(1):1-4 (Oct 1, 2000).
Brodeur et al. Monoclonal Antibody Production Techniques and Applications New York:Marcel Dekker, Inc.,:51-63. ( 1987).
Bruggemann et al., "Comparison of the effector functions of human immunoglobulins using a matched set of chimeric. antibodies" J Exp Med 166(5):1351-61 (Nov. 1987).
Brunhouse, R., et al., "Isotypes of IgG: comparison of the primary structures of three pairs of isotypes which differ in their ability to activate complement" Mol Immunol 16(11):907-917 (Nov. 1, 1979).
Bulbarelli et al., Journal of Cell Science 115:1689-1702 ( 2002).
Burton, D.R. et al., "The C1q receptor site on immunoglobulin G" Nature 288(5789):338-344 (Nov. 27, 1980).
Cambridge, G. et al., "B lymphocyte depletion in patients with rheumatoid arthritis: serial studies of immunological parameters" Arthritis Rheum (Abstract #1350), 46(9):5506 (Sep. 1, 2002).
Capel, P., et al., "Heterogeneity of human IgG Fc receptors" Immunomethods 4(1):25-34 (Feb. 1, 1994).
Carter, P., et al., "'Knobs-into-holes' provides a rational design strategy for engineering antibody CH3 domains for heavy chain heterodimerization" Immunotechnology 2(1):73 (Jan. 1996).
Carter, P., et al., "Humanization of an Anti-p185%superscript:HER2\\\ Antibody for Human Cancer Therapy" PNAS 89(10):4285-4289 (May 15, 1992).
Chari, R., et al., "Immunoconjugates containing novel maytansinoids: Promising anticancer drugs" Cancer Res 52(1):127-131 (Jan. 1, 1992).
Charlton, K.A., "Expression and isolation of recombinant antibody fragments in *E. coli* " Methods Mol Biol 248:245-254 ( 2003).
Chen, C., et al., "Enhancement and Destruction of Antibody Function by Somatic Mutation: Unequal Occurrence is Controlled by V Gene Combinatorial Associations" EMBO J 14(12):2784-2794 (Jun. 15, 1995).
Chen, X. et al., "Fusion Protein Linkers: Property, Design and Functionality" Adv Drug Deliv Rev 65(10):1357-1369 (Oct. 15, 2013).
Cheong et al., "Affinity enhancement of bispecific antibody against two different epitopes in the same antigen" Biochemical and Biophysical Research Communications 173(3):795-800 (Dec. 31, 1990).
Chothia et al., "Canonical structures for the hypervariable regions of immunoglobulins" J Mol Biol 196(4):901-917 (Apr. 23, 1987).
Chowdhury, P., "Engineering hot spots for affinity enhancement of antibodies" Methods Mol Biol 207:179-196 ( 2003).
Clackson et al., "Making antibody fragments using phage display libraries" Nature 352(6336):624-628 (Aug 15, 1991).
Clynes, R., et al., "Fc receptors are required in passive and active immunity to melanoma" PNAS USA 95(2):652-656. (Jan. 1, 1998).
Clynes, R., et al., "Fe receptors are required in passive and active immunity to melanoma" PNAS USA 95(2):652-656 (Jan. 1, 1998).
Coll, A., et al., "Rituximab therapy for the type B syndrome of severe insulin resistance" New Engl J Med 350(3):310-311 (Jan. 15, 2004).

(56) References Cited

OTHER PUBLICATIONS

Coloma et al., "Position Effects of Variable Region Carbohydrate on the Affinity and in Vivo Behavior of an Anti-(1-6) Dextran Antibody" Journal of Immunology 162:2162-2170 ( 1999).

Communication Pursuant to Article 94(3) EPC issued by the European Patent Office, dated Sep. 2, 2009, in related European Patent Appl. No. 06 829 502.1.

Cover page with English translation of Office Action issued by the Peruvian Patent Office, dated Feb. 10, 2010.

Cragg, M., et al., "Antibody Specificity Controls in Vivo Effector Mechanisms of Anti-CD20 Regents" Blood 103(7):2738-2743 (Apr. 1, 2004).

Cragg, M., et al., "Complement-mediated lysis by anti-CD20 mAb correlates with segregation into lipid rafts" Blood 101(3):1045-1052 (Feb. 1, 2003).

Cribbs et al., "Adjuvant-dependent modulation of Th1 and Th2 responses to immunization with b-amyloid" International Immunology 15(4):505-514 ( 2003).

Cross, A., et al., "Preliminary Results from a Phase II trial of Rituximab in MS" Abstract 8th Ann. Meeting of the Americas Committee, for Research and Treamtnet in Multiple Sclerosis, San Francisco, CA -US, Pgs. 20-21 ( Oct. 19,2003).

Cunningham, B., et al., "High-resolution epitope mapping o-f hGH-receptor interactions by alanine-scanning mutagensis" Science 244(4908):1081-1085 (Jun. 2, 1989).

"CytoTox 96® non-radioactive cytotoxicity assay (Promega, Madison, WI)": 21.

Dall'Acqua, W., et al., "Antibody humanization by framework shuffling" Methods 36(1):43-60 (Jan. 17, 2005).

D'Arena, G., et al., "Late and long-lasting response in an adult chronic idiopathic thrombocytopenic purpura after extended course of rituximab" Leuk Lymphoma 44(3):561-562 (Mar. 1, 2003).

De Haas, M., et al., "Fcγ receptors of phagocytes" J Lab Clin Med 126(4):330-341 (Oct. 1, 1995).

De Vita, S., et al., "Efficacy and Safety of Rituximab Treatment in Type II Mixed Cryoglobulinemia" Abstract (Arthritis & Rheum., Abstract #469,) ACR Concurrent Session Vaculitis: Novel Treatment and Pathogenesis, New Orleans, LA-US, pgs. S206 ( Oct. 26,2002).

De Vita, S., et al., "Efficacy of Selective B Cell Blockade in the Treatment of Rheumatoid Arthritis" Arthritis Rheum 46(8):2029-2033 (Aug. 2002).

Deyev, S., et al., "Modern Technologies for Creating Synthetic Antibodies for Clinical Application" Acta Naturae 11(1):32-50 (Apr. 1, 2009).

Dubowchik, G., et al., "Doxorubicin immunoconjugates containing bivalent, lysosomally-cleavable dipeptide linkages" Bioorg Med Chem Lett 12(11):1529-1532 (Jun. 3, 2002).

Duncan, A., et al., "The Binding Site for C1q on IgG" Nature 332(6166):738-740 (Apr. 21, 1988).

Dupuy, A., et al., "Treatment of refractory pemphigus vulgaris with rituximab (anti-CD20 monoclonal antibody)" Arch Dermatol 140(1):91-96 (Jan 1, 2004).

Edwards, B., et al., "The remarkable flexibility of the human antibody repertoire; isolation of over one thousand different antibodies to a single protein, BLyS" J Mol Biol 334(1):103-118 (Nov. 14, 2003).

Edwards, J., et al., "B-lymphocyte depletion therapy in rheumatoid arthritis and other autoimmune disorders" Biochem Soc Trans 30(4):824-828 (Aug. 1, 2002).

Edwards, J., et al., "Efficacy and safety of Rituximab, a B-cell targeted chimeric monoclonal antibody: a randomized, placebo-controlled trial in patients with rheumatoid arthritis" Arthritis Rheum (Abstract #446), 46(9):S197 ( 2002).

Edwards, J., et al., "Sustained Improvement in Rheumatoid Arthritis Following a Protocol Designed to Deplete B Lymphocytes" Rheumatology 40(2):205-211 (Feb. 1, 2001).

Einfeld, D., et al., "Molecular Cloning of the Human B Cell CD20 Receptor Predicts a Hydrophobic Protein with Multiple Transmembrane Domains" EMBO J 7(3):711-717 (Mar. 1, 1988).

Eisenberg R., "SLE—Rituximab in lupus" Arthritis Res Ther 5(4):157-159 ( 2003).

Emery et al., "Sustained Efficacy at 48 Weeks after Single treatment Course of Rituximab in patients with Rheumatoid Arthritis" Arthritis Rheum ((Abstract #1095)), 48(9 Suppl 5439) ( 2003).

Endo et al., "Glycosylation of the variable region of immunoglobulin G—site specific maturation of the sugar chain" Mol Immunol 32(13):931-940 ( 1995).

English translation Notice of the Result of Substantive Examination of a Patent Application issued by the Patents Office of the Cooperation Council for the Arab States of the Gulf GCC, dated Jan. 2, 2010, in related Appl. No. 7376.

English translation of Japanese Office Action (Notification of Reasons for Rejection), issued May 28, 2019, in the related Japanese Patent Application No. 2018-516702.

English translation of Notice of Grounds for Rejection in Japanese Patent Application No. 2009-053951, dispatched on Aug. 11, 2011.

English translation of Notice of Preliminary Rejection and cited references issued by the Korean Patent Office, dated Jan. 13, 2011, in related Korean Patent Application No. 7012289/2008.

English translation of Office Action and Search Report issued by the Taiwanese Patent Office, dated Jul. 22, 2009, in related Patent Application No. 095146304.

English translation of Office Action issued by Israeli Patent Office dated Jul. 14, 2010, in related Israeli Patent Application No. 191004.

English translation of Office Action issued by the Mexican Patent Office, dated Mar. 18, 2011, in related Mexican Patent Appl. No. Mx/a/2008/006948.

English translation of Office Action issued by the Pakistani Patent Office, dated Jul. 30, 2009, in related Pakistani Patent Appl. No. 162912006.

English translation of Office Action issued by the Russian Patent Office, dated Mar. 23, 2011, in related Russian batent Application 2008 128 138.

English translation of Office Action issued by the Russian Patent Office, dated Sep. 23, 2010, in related Russian Patent Application 2008 128 138.

English translation of Office Action issued by the State Intellectual Property Office of the PRC, dated Dec. 28, 2010, in related Chinese Application No. 200680046307.9.

English translation of Office Action issued by the Taiwan Patent Office in Roc (Taiwan) Patent Application No. 095146304, dated Aug. 20, 2012.

English translation of Office Action--Preliminary Examination Report issued by the Ukrainian Patent Office, dated Jun. 14, 2011, in related Ukrainian Patent Application No. a 20080879.

Eriksson, "Short-term outcome and safety in 5 patients with ANCA-positive vasculitis treated with rituximab" Kidney Blood Press R (Abstract P87), 26:294 ( 2003).

Examiner's First Report issued by the Australian Patent Office, dated Aug. 23, 2010, in related Australian patent application No. 2006326301.

Felgenhauer et al., "Protein size and cerebrospinal fluid composition" Klin. WSCHR 52:1158-1164 ( 1974).

Flatman, S., et al., "Process analytics for purification of monoclonal antibodies" J Chromatogr 848(1):79-87 (Mar. 15, 2007).

Frenkel et al., "High affinity binding of monoclonal antibodies to the sequential epitope EFRH of b-amyloid peptide is essential for modulation of fibrillar aggregation" Journal of Immunology 95:136-142 ( 1999).

Frenkel et al "Immunization against Alzheimer's b-amyloid plaques via EFRH phage administration" PNAS 97(21): 11455-11459 ( 2000).

Frenkel et al., "N-terminal EFRH sequence of Alzheimer's b-amyloid peptide represents the epitope of its anti-aggregating antibodies" Journal of Neuroimmunology 88:85-90 ( 1998).

Gazzano-Santoro, H., et al., "A non-radioactive complement-dependent cytotoxicity assay for anti-CD20 monoclonal antibody" J Immunol Methods 202(2):163-171 (Mar. 28, 1997).

Gerngross, T. U., et al., "Advances in the production of human therapeutic proteins in yeasts and filamentous fungi" Nat Biotech 22(11):1409-1414 (Nov. 1, 2004).

(56) References Cited

OTHER PUBLICATIONS

Gessner, J., et al., "The IgG Fc Receptor Family" Ann Hematol 76(6):231-248 (Jun. 1, 1998).
Ghoshal et al., "Tau-66: evidence for a novel tau conformation in Alzheimer's disease" Journal of Neurochemistry 77:1372-1385 ( 2001).
Glenner et al., "Alzheimer'S Disease and Dowi\'S Syndrome: Sharing of a Unique Cerebrovascular Amyloid Fibril Protein" Biochem Biophys Res Commun. 122(3):1131-1135 ( 1984).
Gorman, C. et al., "Does B cell depletion have a role to play in the treatment of systemic lupus erythematosus?" Lupus 13(5):312-316 ( 2004).
Graham, F., et al., "Characteristics of a Human Cell Line Transformed by DNA from Human Adenovirus Type 5" J Gen Virol 36(1):59-72 (Jul. 1, 1977).
Gulko et al., Biotechnology 3:3-8 ( 2000).
Guyer, R., et al., "Immunoglobulin binding by mouse intestinal epithelial cell receptors" J Immunol 117(2):587-593 (Aug. 1, 1976).
Hardy, "Amyloid, the presenilins and Alzheimer's disease" Trends Neurosci. 20:154-159 ( 1997).
Harper et al., "Models of Amyloid Seeding in Alzheimer'S Disease and Scrapie: Mechanistic Truths and Physiological Consequences of the Time-Dependent Solubility of Amyloid Proteins" Annu. Rev. Biochem. 66:385-407 ( 1997).
Hawker et al., "Rituximab in patients with primary progressive multiple sclerosis: results of a randomized double-blind placebo-controlled multicenter trial" Ann Neurol 66(4):460-471 (Oct. 2009).
Hellstrom, I et al., "Strong antitumor activities of IgG3 antibodies to a human melanoma-associated ganglioside" PNAS USA 82(5):1499-1502 (Mar. 1, 1985).
Hellstrom, I., et al., "Antitumor effects of L6, an IgG2a antibody that reacts with most human carcinomas" PNAS US 83(18)7059-7063 (Sep. 1, 1986).
Hellstrom, K., et al. Controlled Drug Delivery: Fundamentals and Applications "Chapter 15: Antibodies for Drug. !Delivery" Robinson, J., and Lee, V., eds., Second edition, Basel, CH and New York, NY-US:Marcel Dekker, Inc., vol. 29:623-642 ( 1987).
Hezareh, M., et al., "Effector function activities of a panel of mutants of a broadly neutralizing antibody against human immunodeficiency virus type 1." J Virol 75(24):12161-12168 (Dec. 1, 2001).
Higashida, J., et al., "Treatment of DMARD-Refractory Rheumatoid Arthritis With Rituximab" Poster (Abstract #LB11) Annual Scientific Meeting of the American College of Rheumatology, New Orleans, LA -US, ( Oct. 24-29,2002).
Hinman, L., et al., "Preparation and characterization of monoclonal antibody conjugates novel and potent family of antitumor antibiotics" Cancer Res 53(14):3336-3342 of the calicheamicins: a (Jul. 15, 1993).
Hoogenboom, H., et al., "Overview of antibody phage-display technology and Biol 178:1-37 ( 2002) its applications" Methods Mol Biol 178:1-37 ( 2002).
Idusogie, E. et al., "Mapping of the C1q Binding Site on Rituxan, A Chimeric Antibody with a human IgG1 Fc" J Immunol 164(8):4178-4184 (Apr. 15, 2000)
International Search Report and Written Opinion (dated Mar. 6, 2014) for International Patent Application No. PCT/EP2013/067595.
International Preliminary Report on Patentability (IPRP) for PCT/EP2016/073413 dated Apr. 3, 2018.
International Search Report and Written Opinion for PCT/EP 2016/073413 dated Jan. 9, 2017.
International Search Report and Written Opinion prepared by the European Patent Office dated Apr. 8, 2015, for International Application No. PCT/EP2014/079353.
International Search Report and Written Opinion prepared by the European Patent Office dated Jan. 23, 2016, for International Application No. PCT/EP2016/064460.
International Search Report for PCT/EP 2016/073413 dated Jan. 9, 2017.
International Search Report PCT/EP2016/073411 dated Dec. 14, 2016.
Janeway, C., "Autoimmune disease: immunotherapy by peptides?" Nature 341(6242):482-483 (Oct. 12, 1989).
Jarrett et al., Cell 73:1055-1058 ( 1993).
Jayne, D., "Current attitudes to the therapy of vasculitis" Kidney Blood Press R 26(4):231-239 ( 2003).
Jayne, D., et al., "B-cell depletion with rituximab for refractory vasculitis" Kidney Blood Press R (Abstract P88), 26:294-295 ( 2003).
Jeffrey, S., et al., "Dipeptide-based highly potent doxorubicin antibody conjugates" Bioorg Med Chem Lett 16(2):358-362 (Jan. 15, 2006).
Jost et al., the Journal of Biological Chemistry 269(42):26267-26273 ( 1994).
Kabat et al., "Sequences of Proteins of Immunological Interest" NIH Publication NIH 91/3242 (Fifth Edition), 1:647-669 ( 1991).
Kabat, E. et al., "Sequences of Proteins of Immunological Interest" 1(Fifth Edition):661-723 ( 1991).
Kabat, E. et al., "Sequences of Proteins of Immunological Interest" 1(Fifth Edition):647-660 ( 1991).
Kabat, E., et al. Sequences of Proteins of Immunological Interest 5th edition,NIH,:2 pp. ( 1991).
Kam, N. et al., "Carbon nanotubes as multifunctional biological transporters and near-infrared agents for selective cancer cell destruction" PNAS USA 102(33):11600-11605 (Aug. 16, 2005).
Kanda, Y., et al., "Comparison of cell lines for stable production of fucose-negative antibodies with enhanced ADCC" Biotechnol Bioeng 94(4):680-688 (Jul. 5, 2006).
Kashmiri, S., et al., "SDR grafting—a new approach to antibody humanization" Methods 36:25-34 (Jan. 1, 2005).
Kay et al. et al., "An M13 phage library displaying random 38-amino-acid peptides affinity to selected targets" Gene 128:59-65 ( 1993).
Kazkaz, H., et al., "Anti B cell Therapy (rituximab) in the treatment of autoimmune diseases" Curr Opin Pharmacol 4(4):398-402 (Aug. 1, 2004).
Keogh, K. et al., "Rituximab for Remission Induction in Severe ANCA-Associated Vascultites. A Report of a Prospective Open-Label Pilot Trial in 10 Patients" Abstract (Abstract 605) American College of Rheumatlogy, Session title: Vascultitis, Orlando, Florida -US, p. 1 (Oct. 18,2004).
Kim, J., et al., "Localization of the site of the murine IgG1 molecule that is involved in binding to the murine intestinal Fc receptor" Eur J Immunol 24(10):2429-2434 (Oct. 1, 1994).
Kindt et al. Kuby Immunol Sixth edition, New York:W. H. Freeman and Company,:91 ( 2007).
King, H.D., et al., "Monoclonal antibody conjugates of doxorubicin prepared with branched peptide linkers: Inhibition of aggregation by methoxytriethyleneglycol chains" J Med Chem 45(19):4336-4343 (Sep. 12, 2002).
Kjeldsen et al., Gene 170:107-112 ( 1996).
Klemmer, N., et al., "Treatment of antibody mediated autoimmune disorders with a Anti-CD20 monoclonal antibody Yes : Rituximab" Arthritis Rheum (Abstract #1623), 48( Suppl Supp! 9):S624 (Sep. 1, 2003).
Klimka, a et al., "Human anti-CD30 recombinant antibodies by guided phage antibody selection using cell panning" Br J Cancer 83(2):252-260 (Mar. 1, 2000).
Knappik et al., "Fully Synthetic Human Combinatorial Antibody Libraries (HuCAL) Based on Modular Consensus Frameworks and CDRs Randomized with Trinucleotides" J. Mol. Biol. 296(1):57-86 (Feb. 11, 2000).
Kneitz, C., et al., "Effective B cell depletion with rituximab in the treatment of autoimmune diseases" Immunobiology 206(5):519-527 (Dec. 1, 2002).
Kontermann et al., "Dual targeting strategies with bispecific antibodies" MABS 4(2):182-197 ( 2012).
Koo et al., "Amyloid diseases: Abnormal protein aggregation in neurodegeneration" PNAS 96:9989-9990 ( 1999).
Kozbor, D., et al., "A Human Hybrid Myeloma for Production fo Human Monoclonal Antibodies" J Immunol 133(6):3001-3005 (Dec. 1, 1984).

(56) References Cited

OTHER PUBLICATIONS

Kratz, F., et al., "Prodrugs of anthracyclines in cancer chemotherapy" Curr Med Chem 13(5):477-523 (Mar. 1, 2006).
Kussie et al., "A Single Engineered Amino Acid Substitution Changes Antibody Fine Specificity" Journal of Immunology 152:146-152 (1994).
Lake and Dionne et al. Burger's Medicinal Chemistry and Drug Discovery "6" Abraham, 6th edition, Hoboken:John Wiley & Sons, Inc., vol. 5:223-247 (2003).
Layios, N., et al., "Remission of severe cold agglutinin disease after Rituximab therapy" Leukemia 15(1):187-188 (Jann. 1, 2001).
Leandro, M., et al., "An open study of B lymphocyte depletion in systemic lupus erythematosus" Arthritis Rheum 46(10):2673-2677 (Oct. 1, 2002).
Leandro, M., et al., "B cell repopulation occurs mainly from naive B cells in patients with rheumatoid arthritis and systemic lupus erythematosus treated with rituximab" Arthritis Rheum (Abstract#1160), 48( SUPPL Suppl 9):S464 (Oct. 27, 2003).
Leandro, M., et al., "Clinical outcome in 22 patients with rheumatoid arthritis treated with B lymphocyte depletion" Ann Rheum Dis 61(10):883-888 (Oct. 1, 2002).
Leandro, M., et al., "Treatment of refractory lupus nephritis with B lymphocyte depletion" Arthritis Rheum (Abstract #924), 48( Suppl Supplement 9):S378 ( 2003).
Leibiger et al., et al., "Variable domain-linked oligosaccharides of a human monoclonal IgG : structure and influence on antigen binding" Biochem. J. 338:529-538 ( 1999).
Levine, "A Pilot Study of Rituximab Therapy for Refractory Dermatomyositis" Arthritis Rheum (Abstract #1299), 46( Suppl Suppl 9):S488-S489 ( 2002).
Levine, T., et al., "IgM antibody-related polyneuropathies: B-cell depletion chemotherapy using Rituximab" Neurology 52(8):1701-1704 (May 12, 1999).
Li et al., Acta Theriologica Sinica 26(1):38-43 ( 2006).
Li et al., "Antibody conjugation via one and two C-terminal selenocysteines" Methods 65:133-138 ( 2014).
Li, H., et al., "Optimization of humanized igGs in glycoengineered pichia pastoris" Nat Biotechnol 24(2):210-215 (Feb. 1, 2006).
Li, J., et al., "Human antibodies for immunotherapy development generated via a human B cell hybridoma technology" PNAS USA 103(10):3557-3562 (Mar. 7, 2006).
Liang and Tedder et al. Wiley Encyclopedia of Molecular Medicine John Wiley & Sons, Inc., New York:John :Wiley,:562-564 (Jan. 15, 2002).
Lloyd, C., et al., "Modelling the human immune response: performance of a 1011 human antibody repertoire against a broad panel of a therapeutically relevant antigens" Protein Eng Des Sel 22(3):159-168 (Mar. 1, 2009).
Lonberg, N., "Human antibodies from transgenic animal" Nat Biotechnol 23(9):1117-11125 (2005).
Lonberg, N., et al., "Fully human antibodies fromm transgenic mouse and phage display platforms" Curr Opin Immunol 20(4):450-459 (Aug. 1, 2008).
Lund, J., et al., "Oligosaccharide-protein interaction in IgG can modulate recognition by Fc gamma receptors" FASEB J. 9(1):115-119 (Jan. 1, 1995).
MacCallum, R., et al., "Antibody-antigen Interactions: Contact Analysis and Binding Site Topgraphy"J Mol Biol 262(5):732-745 (Oct. 11, 1996).
Morgan, A. et al., "The N-terminal end of the CH2 domain of chimeric human IgG1 anti-HLA-DR is necessary for C1q, Fc gamma RI and Fc gamma RIII binding" Immunology 86(2);319-324 (Oct. 1, 1995).
Ni et al., "Research progress and future perspectives in antibodomics and antibodomic drugs" Xiandai Mianyixue ((Abstract only)), 26(4):265-268 ( 2006).
Office Action issued by the Colombian Patent Office in Application No. 2008 049920-A, dated Sep. 6, 2012.
Office Action issued by the Malaysian Patent Office in Application No. P1 20081349, dated Nov. 14, 2012.

Office Action issued by the New Zealand Patent Office, dated Apr. 13, 2010, in related New Zealand Patent Appl. No. 068241.
Petkova, S., et al., "Enhanced half-life of genetically engineered human IgG1 antibodies in a humanized FcRn mouse model: potential application in humorally mediated autoimmune disease" Int Immunol 18(12):1759-1769.
Press, O., et al., "Monoclonal Antibody IF5 (Anti-CD20) Serotherapy of Human B Cell Lymphomas" Blood. 69(2):584-591 (Feb. 1, 1987).
Presta, L., et al., "Humanization of Antibody Directed Against IgE" J Immunol 151(5):2623-2632 (Sep. 1, 1993).
Ravetch and Kinet et al., "Fc receptors" Ann. Rev. Immunol. 9:457-492 ( 1991).
Ravetch, J. et al., "IgG Fc receptors" Ann Rev Immunol 19:275-290 ( 2001).
Riechmann, L., "Reshaping human antibodies for therapy" Nature 332(6162):323-327 (Mar. 24, 1988).
Schneider, C., et al., "Primary structure of human transferrin receptor deduced from the mRNA sequence" Nature 311(5987):675-678 (Oct. 18, 1984).
Shields et al., "High Resolution Mapping of the Binding Site on Human IgG1 for FcγRI, FcγRII, FcγRIII, and FcRn and Design of IgG1 Variants with Improved Binding to the FcγR" J Biol Chem 276(9):6591-6604 ( 2001).
Sinha et al., "Cellular mechanisms of b-amyloid production and secretion" PNAS 96:11049-11053 ( 1999).
Spiess, C., et al., "Alternative molecular formats and therapeutic applications for bispecific antibodies" Mol Immunol 67( Suppl 2 Pt A):95-106 (Jan. 27, 2015).
Stahl, H., et al., "Rituximab in RA: Efficacy and safety from a randomised, controlled trial" Ann Rheum Dis 62( Suppl Suppl 1) ( 2003).
Stasi, R., et al., "Rituximab chimeric anti-CD20 monoclonal antibody treatment for adults with chronic idiopathic thrombocytopenic purpura" Blood 98(4):952-957 (Aug. 15, 2001).
Sumbria, R., et al., "Disaggregation of Amyloid Plaque in Brain of Alzheimer's Disease Transgenic Mice with Daily Subcutaneous Administration of a Tetravalent Bispecific Antibody That Targets the Transferrin Receptor and the Abeta Amyloid Peptide" Mol Pharm 10(9):3507-3513 (Sep. 3, 2013).
Thorpe, Monoclonal Antibodies 84: Biological and Clinical Applications A. Pinchera, G. Doria, F. Dammacco & Bargellesi,Editrice Kurtis s.r.l. (Publisher),:475-506 ( 1985)
Torgov, M., et al., "Generation of an intensely potent anthracycline by a monoclonal antibody--β-galactosidase conjugate" Bioconjugate Chem 16(3):717-21 (May 1, 2005).
Valentine, M., et al., "Phosphorylation of the CD20 Phosphoprotein in Resting B Lymphocytes" J Biol Chem :264(19):11282-11287 (Jul. 5, 1989).
Van De Winkel, J.G., et al., "Biology of human immunoglobulin G Fc receptors" J Leukocyte Biol 49(5):511-524 (May 1, 1991).
Van Dijk and Van De Winkel et al., "Human antibodies as next generation therapeutics" Curr Opin Chem 5(4):368-374 (Aug. 2001).
Vitetta et al., "Redesigning nature's poisons to create anti-tumor reagents" Science 238:1098-1104 ( 1987).
Vollmers, H., et al., "The 'early birds': Natural IgM antibodies and immune surveillance" Histol Histopathol 20(3):927-937 (Jul. 1, 2005).
Von Budingen, H., et al., "B cells in multiple sclerosis: connecting the dots" Curr Opin Immunol 23(6):713-720 (Dec. 1, 2011).
Wagner, E., et al., "Transferrin-Polycation Conjugates as Carriers for DNA Uptake Into Cells" PNAS USA 87(9):3410-3414 (May 1, 1990).
Weissmiller et al., Translational Neurodegeneration 1(14):1-9 ( 2012).
Wright, A., et al., "Effect of glycosylation on antibody function: Implications for genetic engineering" Trends Biotechnol 15(1):26-32 (Jan. 1, 1997).
Wu, G.Y. and C. H. Wu., "Receptor-Mediated in Vitro Gene Transformation by a Soluble DNA Carrier System" J Biol Chem 262(10):4429-4432 (Apr. 5, 1987).
Yamane-Ohnuki, N., et al., "Establishment of FUT8 knockout Chinese hamster ovary cells: an ideal host cell line for producing

(56) References Cited

OTHER PUBLICATIONS completely defucosylated antibodies with enhanced antibody-dependent cellular cytotoxicity" Biotechnol Bioeng 87(5):614-622 (Sep. 5, 2004).
Zaja, F., et al., "B-cell depletion with rituximab as treatment for immune hemolytic anemia and chronic thrombocytopenia" Haematologica 87(2):189-195 (Feb. 1, 2002).
Zaja, F., et al., "Rituximab in a case of cold agglutinin disease" Br J Haematol 115(1):232-233 (Oct. 1, 2001).
Supreme People's Court of People's Republic of China Administrative Judgment (2019) Zui Gao Fa Zhi XingZhong No. 235.
Pardridge et al., "Selective Transport of an Anti-Transferrin Receptor Antibody Through the Blood-Brain Barrier in Vivo" Journal of Pharmacology and Experimental Therapeutics 259(1):66-70 ( 1991).
Ulbrich et al., "Transferrin-and transferrin-receptor-antibody-modified nanoparticles enable drug delivery across the blood-brain barrier (BBB)" European Journal of Pharmaceutics and Biopharmaceutics 71:251-256 ( 2009).
Yan et al., "Soluble expression and target study to brain of anti-TfRScFv" Chinese Journal of Biotechnology (English abstract), 20(3):342-347 ( 2004).
Zhao et al., "Expression, purification and activity analysis of anti-human transferrin receptor scFv" Chinese Journal of Biotechnology (English abstract), 22(3):488-491 ( 2006).
Chen et al., "Modern methods for delivery of drugs across the blood—brain barrier" Advanced Drug Delivery Reviews 64:640-665 ( 2012).
Pardridge, W.M., "Re-Engineering Biopharmaceuticals for Delivery to Brain with Molecular Trojan Horses" Bioconjugate Chemistry 19(7):1327-1338 ( 2008).
NCBI et al., "Sequence Viewer v3.1 Report—Complete Nucleotide Sequence of the High Molecular Weight Human IGF-I mRNA" (NCBI_IGF-1_P01343),:1-3 (Nov. 4, 2016).
Zhai et al., "GenBank NCBI) Accesion No. AGB. 75998":1 (Sep. 23, 2021).

ately 0.1%) of an IgG injected in the bloodstream are able to penetrate into the CNS compartment (Felgenhauer, Klin. Wschr. 52 (1974) 1158-1164). This will certainly limit any pharmacological effect due to the low concentration within CNS of the antibody.

```
                        SEQUENCE LISTING

<160> NUMBER OF SEQ ID NOS: 97

<210> SEQ ID NO 1
<211> LENGTH: 122
<212> TYPE: PRT
<213> ORGANISM: Oryctolagus cuniculus

<400> SEQUENCE: 1

Gln Ser Met Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Arg Tyr
                85                  90                  95

Gly Thr Ser Tyr Pro Asp Tyr Gly Asp Ala Asn Gly Phe Asp Pro Trp
            100                 105                 110

Gly Pro Gly Thr Leu Val Thr Val Ser Ser
        115                 120

<210> SEQ ID NO 2
<211> LENGTH: 122
<212> TYPE: PRT
<213> ORGANISM: Artificial Sequence
<220> FEATURE:
<223> OTHER INFORMATION: anti-TfR mAb 567 VH (=humanized 299 VH_basic)

<400> SEQUENCE: 2

Gln Ser Met Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80
```

```
Ser Pro Thr Thr Glu Asp Thr Ala Thr Tyr Phe Cys Ala Arg Arg Tyr
            85                  90                  95

Gly Thr Ser Tyr Pro Asp Tyr Gly Asp Ala Asn Gly Phe Asp Pro Trp
            100                 105                 110

Gly Pro Gly Thr Leu Val Thr Val Ser Ser
            115                 120

<210> SEQ ID NO 3
<211> LENGTH: 124
<212> TYPE: PRT
<213> ORGANISM: Artificial Sequence
<220> FEATURE:
<223> OTHER INFORMATION: 299-001 VH humanization variant

<400> SEQUENCE: 3

Val Gln Leu Val Glu Thr Gly Gly Gly Leu Ile Gln Pro Gly Gly Ser
1               5                   10                  15

Leu Arg Leu Ser Cys Ala Ala Ser Gly Phe Ser Leu Ser Ser Tyr Ala
            20                  25                  30

Met Ser Trp Val Arg Gln Ala Pro Gly Lys Gly Leu Glu Trp Val Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
            115                 120

<210> SEQ ID NO 4
<211> LENGTH: 125
<212> TYPE: PRT
<213> ORGANISM: Artificial Sequence
<220> FEATURE:
<223> OTHER INFORMATION: 299-002 VH humanization variant

<400> SEQUENCE: 4

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Ala Met Ser Trp Val Arg Gln Ala Pro Gly Lys Gly Leu Glu Trp Val
        35                  40                  45

Gly Tyr Ile Trp Ser Gly Gly Ser Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Tyr Gly Thr Ser Tyr Pro Asp Tyr Gly Asp Ala Asn Gly Phe
            100                 105                 110

Asp Pro Trp Gly Gln Gly Thr Leu Val Thr Val Ser Ser
            115                 120                 125
```

-continued

```
<210> SEQ ID NO 5
<211> LENGTH: 124
<212> TYPE: PRT
<213> ORGANISM: Artificial Sequence
<220> FEATURE:
<223> OTHER INFORMATION: 299-005 VH humanization variant

<400> SEQUENCE: 5

Gln Ser Met Glu Glu Thr Gly Gly Gly Leu Ile Gln Pro Gly Gly Ser
1               5                   10                  15

Leu Arg Leu Ser Cys Ala Ala Ser Gly Phe Ser Leu Ser Ser Tyr Ala
            20                  25                  30

Met Ser Trp Val Arg Gln Ala Pro Gly Lys Gly Leu Glu Trp Val Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Pro Gly Thr Leu Val Thr Val Ser Ser
        115                 120

<210> SEQ ID NO 6
<211> LENGTH: 124
<212> TYPE: PRT
<213> ORGANISM: Artificial Sequence
<220> FEATURE:
<223> OTHER INFORMATION: 299-006 VH humanization variant

<400> SEQUENCE: 6

Gln Gln Leu Val Glu Thr Gly Gly Gly Leu Ile Gln Pro Gly Gly Ser
1               5                   10                  15

Leu Arg Leu Ser Cys Ala Ala Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
        115                 120

<210> SEQ ID NO 7
<211> LENGTH: 124
<212> TYPE: PRT
<213> ORGANISM: Artificial Sequence
<220> FEATURE:
<223> OTHER INFORMATION: 299-007 VH humanization variant_DANG

<400> SEQUENCE: 7

Gln Gln Leu Val Glu Thr Gly Gly Gly Leu Ile Gln Pro Gly Gly Ser
1               5                   10                  15
```

-continued

Leu Arg Leu Ser Cys Ala Ala Ser Gly Phe Ser Leu Ser Ser Tyr Ala
            20                  25                  30

Met Ser Trp Val Arg Gln Ala Pro Gly Lys Gly Leu Glu Trp Ile Gly
            35                  40                  45

Tyr Ile Trp Ser Gly Gly Ser Thr Asp Tyr Ala Ser Trp Ala Lys Gly
50                      55                  60

Arg Phe Thr Ile Ser Arg Asp Asn Ser Lys Asn Thr Leu Tyr Leu Gln
65                      70                  75                  80

Met Asn Ser Leu Arg Ala Glu Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
            115                 120

<210> SEQ ID NO 8
<211> LENGTH: 122
<212> TYPE: PRT
<213> ORGANISM: Artificial Sequence
<220> FEATURE:
<223> OTHER INFORMATION: 299-008 VH humanization variant

<400> SEQUENCE: 8

Gln Gln Leu Val Glu Thr Gly Gly Gly Leu Ile Gln Pro Gly Gly Ser
1               5                   10                  15

Leu Arg Leu Ser Cys Ala Ala Ser Gly Phe Ser Leu Ser Ser Tyr Ala
            20                  25                  30

Met Ser Trp Val Arg Gln Ala Pro Gly Lys Gly Leu Glu Trp Ile Gly
            35                  40                  45

Tyr Ile Trp Ser Gly Gly Ser Thr Asp Tyr Ala Ser Trp Ala Lys Gly
50                      55                  60

Arg Phe Thr Ile Ser Lys Thr Ser Thr Thr Leu Tyr Leu Gln Met Asn
65                      70                  75                  80

Ser Leu Arg Ala Glu Asp Thr Ala Val Tyr Tyr Cys Ala Arg Arg Tyr
                85                  90                  95

Gly Thr Ser Tyr Pro Asp Tyr Gly Asp Ala Asn Gly Phe Asp Pro Trp
            100                 105                 110

Gly Gln Gly Thr Leu Val Thr Val Ser Ser
            115                 120

<210> SEQ ID NO 9
<211> LENGTH: 124
<212> TYPE: PRT
<213> ORGANISM: Artificial Sequence
<220> FEATURE:
<223> OTHER INFORMATION: 299-009 VH humanization variant_DANG

<400> SEQUENCE: 9

Gln Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
            20                  25                  30

Met Ser Trp Val Arg Gln Ala Pro Gly Lys Gly Leu Glu Trp Val Gly
            35                  40                  45

Tyr Ile Trp Ser Gly Gly Ser Thr Asp Tyr Ala Asp Ser Val Lys Gly
50                      55                  60

```
Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: 299-009 VH humanization variant_DASG

<400> SEQUENCE: 10

Gln Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
                20                  25                  30

Met Ser Trp Val Arg Gln Ala Pro Gly Lys Gly Leu Glu Trp Val Gly
            35                  40                  45

Tyr Ile Trp Ser Gly Gly Ser Thr Asp Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Tyr Gly Thr Ser Tyr Pro Asp Tyr Gly Asp Ala Ser Gly Phe Asp
            100                 105                 110

Pro Trp Gly Gln Gly Thr Leu Val Thr Val Ser Ser
        115                 120

<210> SEQ ID NO 11
<211> LENGTH: 124
<212> TYPE: PRT
<213> ORGANISM: Artificial Sequence
<220> FEATURE:
<223> OTHER INFORMATION: 299-009 VH humanization variant_DAQG

<400> SEQUENCE: 11

Gln Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
                20                  25                  30

Met Ser Trp Val Arg Gln Ala Pro Gly Lys Gly Leu Glu Trp Val Gly
            35                  40                  45

Tyr Ile Trp Ser Gly Gly Ser Thr Asp Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Tyr Gly Thr Ser Tyr Pro Asp Tyr Gly Asp Ala Gln Gly Phe Asp
            100                 105                 110
```

```
Pro Trp Gly Gln Gly Thr Leu Val Thr Val Ser Ser
        115                 120
```

<210> SEQ ID NO 12
<211> LENGTH: 124
<212> TYPE: PRT
<213> ORGANISM: Artificial Sequence
<220> FEATURE:
<223> OTHER INFORMATION: 299-011 VH humanization variant

<400> SEQUENCE: 12

```
Gln Gln Leu Leu Glu Ser Gly Gly Leu Val Gln Pro Gly Gly Ser
1               5                   10                  15

Leu Arg Leu Ser Cys Ala Ala Ser Gly Phe Ser Leu Ser Ser Tyr Ala
            20                  25                  30

Met Ser Trp Val Arg Gln Ala Pro Gly Lys Gly Leu Glu Trp Val Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
        115                 120
```

<210> SEQ ID NO 13
<211> LENGTH: 125
<212> TYPE: PRT
<213> ORGANISM: Artificial Sequence
<220> FEATURE:
<223> OTHER INFORMATION: 299-012 VH humanization variant

<400> SEQUENCE: 13

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Ala Met Ser Trp Ile Arg Gln Pro Pro Gly Lys Gly Leu Glu Trp Ile
        35                  40                  45

Gly Tyr Ile Trp Ser Gly Gly Ser Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Tyr Gly Thr Ser Tyr Pro Asp Tyr Gly Asp Ala Asn Gly Phe
            100                 105                 110

Asp Pro Trp Gly Gln Gly Thr Leu Val Thr Val Ser Ser
        115                 120                 125
```

<210> SEQ ID NO 14
<211> LENGTH: 125
<212> TYPE: PRT
<213> ORGANISM: Artificial Sequence
<220> FEATURE:
<223> OTHER INFORMATION: 299-013 VH humanization variant -continued

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Ala Met Ser Trp Ile Arg Gln Pro Pro Gly Lys Gly Leu Glu Trp Ile
        35                  40                  45

Gly Tyr Ile Trp Ser Gly Gly Ser Thr Asp Tyr Asn Pro Ser Leu Lys
    50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Arg Tyr Gly Thr Ser Tyr Pro Asp Tyr Gly Asp Ala Asn Gly Phe
            100                 105                 110

Asp Pro Trp Gly Gln Gly Thr Leu Val Thr Val Ser Ser
            115                 120                 125

<210> SEQ ID NO 15
<211> LENGTH: 124
<212> TYPE: PRT
<213> ORGANISM: Artificial Sequence
<220> FEATURE:
<223> OTHER INFORMATION: 299-015 VH humanization variant

<400> SEQUENCE: 15

Gln Gln Leu Gln Glu Ser Gly Pro Gly Leu Val Lys Pro Ser Glu Thr
1               5                   10                  15

Leu Ser Leu Thr Cys Thr Val Ser Gly Phe Ser Leu Ser Ser Tyr Ala
            20                  25                  30

Met Ser Trp Val Arg Gln Pro Pro Gly Lys Gly Leu Glu Trp Ile Gly
        35                  40                  45

Tyr Ile Trp Ser Gly Gly Ser Thr Asp Tyr Asn Pro Ser Leu Lys Ser
    50                  55                  60

Arg Val Thr Ile Ser Val Asp Thr Ser Lys Asn Gln Val Ser Leu Lys
65                  70                  75                  80

Leu Ser Ser Val Thr Ala Ala Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
            115                 120

<210> SEQ ID NO 16
<211> LENGTH: 124
<212> TYPE: PRT
<213> ORGANISM: Artificial Sequence
<220> FEATURE:
<223> OTHER INFORMATION: 299-016 VH humanization variant

<400> SEQUENCE: 16

Gln Gln Leu Gln Glu Ser Gly Pro Gly Leu Val Lys Pro Ser Glu Thr
1               5                   10                  15

Leu Ser Leu Thr Cys Thr Val Ser Gly Phe Ser Leu Ser Ser Tyr Ala
            20                  25                  30

Met Ser Trp Val Arg Gln Pro Pro Gly Lys Gly Leu Glu Trp Ile Gly
        35                  40                  45

Tyr Ile Trp Ser Gly Gly Ser Thr Asp Tyr Asn Pro Ser Leu Lys Ser
            50                  55                  60

Arg Val Thr Ile Ser Val Asp Thr Ser Lys Asn Gln Val Ser Leu Lys
 65                  70                  75                  80

Leu Ser Ser Val Thr Ala Ala Asp Thr Ala Val Tyr Tyr Cys Ala Arg
                 85                  90                  95

Arg Tyr Gly Thr Ser Tyr Pro Asp Tyr Gly Asp Ala Asn Gly Phe Asp
                100                 105                 110

Pro Trp Gly Pro Gly Thr Leu Val Thr Val Ser Ser
            115                 120

<210> SEQ ID NO 17
<211> LENGTH: 124
<212> TYPE: PRT
<213> ORGANISM: Artificial Sequence
<220> FEATURE:
<223> OTHER INFORMATION: 299-017 VH humanization variant

<400> SEQUENCE: 17

Gln Gln Leu Gln Glu Ser Gly Pro Gly Leu Val Lys Pro Ser Glu Thr
 1               5                  10                  15

Leu Ser Leu Thr Cys Thr Val Ser Gly Phe Ser Leu Ser Ser Tyr Ala
                 20                  25                  30

Met Ser Trp Val Arg Gln Pro Pro Gly Lys Gly Leu Glu Trp Ile Gly
             35                  40                  45

Tyr Ile Trp Ser Gly Gly Ser Thr Asp Tyr Asn Pro Ser Leu Lys Ser
            50                  55                  60

Arg Val Thr Ile Ser Lys Asp Thr Ser Lys Asn Gln Val Ser Leu Lys
 65                  70                  75                  80

Leu Ser Ser Val Thr Ala Ala Asp Thr Ala Val Tyr Tyr Cys Ala Arg
                 85                  90                  95

Arg Tyr Gly Thr Ser Tyr Pro Asp Tyr Gly Asp Ala Asn Gly Phe Asp
                100                 105                 110

Pro Trp Gly Pro Gly Thr Leu Val Thr Val Ser Ser
            115                 120

<210> SEQ ID NO 18
<211> LENGTH: 125
<212> TYPE: PRT
<213> ORGANISM: Artificial Sequence
<220> FEATURE:
<223> OTHER INFORMATION: 299-018 VH humanization variant

<400> SEQUENCE: 18

Gln Val Gln Leu Gln Glu Ser Gly Pro Gly Leu Val Lys Pro Ser Gln
 1               5                  10                  15

Thr Leu Ser Leu Thr Cys Thr Val Ser Gly Phe Ser Leu Ser Ser Tyr
                 20                  25                  30

Ala Met Ser Trp Ile Arg Gln His Pro Gly Lys Gly Leu Glu Trp Ile
             35                  40                  45

Gly Tyr Ile Trp Ser Gly Gly Ser Thr Asp Tyr Ala Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

```
Arg Arg Tyr Gly Thr Ser Tyr Pro Asp Tyr Gly Asp Ala Asn Gly Phe
                100                 105                 110

Asp Pro Trp Gly Gln Gly Thr Leu Val Thr Val Ser Ser
            115                 120                 125

<210> SEQ ID NO 19
<211> LENGTH: 124
<212> TYPE: PRT
<213> ORGANISM: Artificial Sequence
<220> FEATURE:
<223> OTHER INFORMATION: 299-019 VH humanization variant

<400> SEQUENCE: 19

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
                20                  25                  30

Met Ser Trp Ile Arg Gln His Pro Gly Lys Gly Leu Glu Trp Ile Gly
            35                  40                  45

Tyr Ile Trp Ser Gly Gly Ser Thr Asp Tyr Ala Pro Ser Leu Lys Ser
    50                  55                  60

Arg Val Thr Ile Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
        115                 120

<210> SEQ ID NO 20
<211> LENGTH: 124
<212> TYPE: PRT
<213> ORGANISM: Artificial Sequence
<220> FEATURE:
<223> OTHER INFORMATION: 299-020 VH humanization variant

<400> SEQUENCE: 20

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
                20                  25                  30

Met Ser Trp Ile Arg Gln His Pro Gly Lys Gly Leu Glu Trp Ile Gly
            35                  40                  45

Tyr Ile Trp Ser Gly Gly Ser Thr Asp Tyr Ala Pro Ser Leu Lys Ser
    50                  55                  60

Arg Val Thr Ile Ser Val Asp Thr Ser Lys Asn Gln Val Ser Leu Lys
65                  70                  75                  80

Leu Ser Ser Val Thr Ala Ala Asp Thr Ala Val Tyr Tyr Cys Ala Arg
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
        115                 120

<210> SEQ ID NO 21
<211> LENGTH: 124
<212> TYPE: PRT
```

```
<213> ORGANISM: Artificial Sequence
<220> FEATURE:
<223> OTHER INFORMATION: 299-021 VH humanization variant

<400> SEQUENCE: 21

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Val Asp Thr Ser Lys Asn Gln Val Ser Leu Lys
65              70                  75                  80

Leu Ser Ser Val Thr Ala Ala Asp Thr Ala Val Tyr Tyr Cys Ala Arg
            85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
            115                 120

<210> SEQ ID NO 22
<211> LENGTH: 124
<212> TYPE: PRT
<213> ORGANISM: Artificial Sequence
<220> FEATURE:
<223> OTHER INFORMATION: 299-022 VH humanization variant

<400> SEQUENCE: 22

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Val Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Val Asp Thr Ser Lys Asn Gln Val Ser Leu Lys
65              70                  75                  80

Leu Ser Ser Val Thr Ala Ala Asp Thr Ala Val Tyr Tyr Cys Ala Arg
            85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
            115                 120

<210> SEQ ID NO 23
<211> LENGTH: 122
<212> TYPE: PRT
<213> ORGANISM: Artificial Sequence
<220> FEATURE:
<223> OTHER INFORMATION: 299-023 VH humanization variant_DANG

<400> SEQUENCE: 23

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30
```

```
Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Asn Gly Phe Asp Pro Trp
                100                 105                 110

Gly Gln Gly Thr Leu Val Thr Val Ser Ser
                115                 120

<210> SEQ ID NO 24
<211> LENGTH: 122
<212> TYPE: PRT
<213> ORGANISM: Artificial Sequence
<220> FEATURE:
<223> OTHER INFORMATION: 299-023 VH humanization variant_DASG

<400> SEQUENCE: 24

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
                20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
                100                 105                 110

Gly Gln Gly Thr Leu Val Thr Val Ser Ser
                115                 120

<210> SEQ ID NO 25
<211> LENGTH: 122
<212> TYPE: PRT
<213> ORGANISM: Artificial Sequence
<220> FEATURE:
<223> OTHER INFORMATION: 299-023 VH humanization variant_DAQG

<400> SEQUENCE: 25

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
                20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80
```

```
Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Gln Gly Phe Asp Pro Trp
            100                 105                 110

Gly Gln Gly Thr Leu Val Thr Val Ser Ser
        115                 120

<210> SEQ ID NO 26
<211> LENGTH: 110
<212> TYPE: PRT
<213> ORGANISM: Oryctolagus cuniculus

<400> SEQUENCE: 26

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Cys Tyr Ser Ser Ser Asn
                85                  90                  95

Val Asp Asn Thr Phe Gly Gly Gly Thr Glu Val Val Val Lys
            100                 105                 110

<210> SEQ ID NO 27
<211> LENGTH: 110
<212> TYPE: PRT
<213> ORGANISM: Artificial Sequence
<220> FEATURE:
<223> OTHER INFORMATION: anti-TfR mAb 567 VL (=humanized 299 VL_basic)

<400> SEQUENCE: 27

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Ser Tyr Ser Ser Ser Asn
                85                  90                  95

Val Asp Asn Thr Phe Gly Gly Gly Thr Glu Val Val Val Lys
            100                 105                 110

<210> SEQ ID NO 28
<211> LENGTH: 110
<212> TYPE: PRT
<213> ORGANISM: Artificial Sequence
<220> FEATURE:
<223> OTHER INFORMATION: 567 VL humanization variant_PNYA
```

-continued

<400> SEQUENCE: 28

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
50                  55                  60

Ser Gly Ser Gly Thr Gln Phe Thr Leu Thr Ile Ser Gly Val Glu Pro
65                  70                  75                  80

Ala Asp Ala Ala Thr Tyr Tyr Cys Gln Gln Asn Tyr Ala Ser Ser Asn
                85                  90                  95

Val Asp Asn Thr Phe Gly Gly Gly Thr Glu Val Val Val Lys
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: 299-001 VL humanization variant

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 30
<211> LENGTH: 110
<212> TYPE: PRT
<213> ORGANISM: Artificial Sequence
<220> FEATURE:
<223> OTHER INFORMATION: 299-002 VL humanization variant_SYS

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: 299-003 VL humanization variant

<400> SEQUENCE: 31

Ala Tyr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 32
<211> LENGTH: 110
<212> TYPE: PRT
<213> ORGANISM: Artificial Sequence
<220> FEATURE:
<223> OTHER INFORMATION: 299-004 VL humanization variant

<400> SEQUENCE: 32

Ala Tyr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 33
<211> LENGTH: 110
<212> TYPE: PRT
<213> ORGANISM: Artificial Sequence
<220> FEATURE:
<223> OTHER INFORMATION: 299-005 VL humanization variant

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: 299-006 VL humanization variant_SYS

<400> SEQUENCE: 34

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 35
<211> LENGTH: 110
<212> TYPE: PRT
<213> ORGANISM: Artificial Sequence
<220> FEATURE:
<223> OTHER INFORMATION: 299-007 VL humanization variant

<400> SEQUENCE: 35

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Asn
                85                  90                  95

Val Asp Asn Thr Phe Gly Gly Gly Thr Lys Val Glu Ile Lys
            100                 105                 110

<210> SEQ ID NO 36
<211> LENGTH: 110
<212> TYPE: PRT
<213> ORGANISM: Artificial Sequence
<220> FEATURE:
<223> OTHER INFORMATION: 299-008 VL humanization variant

<400> SEQUENCE: 36

Ala Tyr Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 37
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 37

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys
            100                 105                 110

<210> SEQ ID NO 38
<211> LENGTH: 110
<212> TYPE: PRT
<213> ORGANISM: Artificial Sequence
<220> FEATURE:
<223> OTHER INFORMATION: 299-009 VL humanization variant_SYA

<400> SEQUENCE: 38

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ala Ser Ser Asn
                85                  90                  95

Val Asp Asn Thr Phe Gly Gly Gly Thr Lys Val Glu Ile Lys
            100                 105                 110

<210> SEQ ID NO 39
<211> LENGTH: 110
<212> TYPE: PRT
<213> ORGANISM: Artificial Sequence
<220> FEATURE:
<223> OTHER INFORMATION: 299-009 VL humanization variant_NYS

<400> SEQUENCE: 39

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ser Ser Ser Asn
                85                  90                  95

Val Asp Asn Thr Phe Gly Gly Gly Thr Lys Val Glu Ile Lys
            100                 105                 110

<210> SEQ ID NO 40
<211> LENGTH: 110
<212> TYPE: PRT
<213> ORGANISM: Artificial Sequence
<220> FEATURE:
<223> OTHER INFORMATION: 299-009 VL humanization variant_GYS

<400> SEQUENCE: 40

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ser Asn
                85                  90                  95

Val Asp Asn Thr Phe Gly Gly Gly Thr Lys Val Glu Ile Lys
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: 299-009 VL humanization variant_CYS

<400> SEQUENCE: 41

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Cys Tyr Ser Ser Ser Asn
                85                  90                  95

Val Asp Asn Thr Phe Gly Gly Gly Thr Lys Val Glu Ile Lys
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: 299-010 VL humanization variant

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 43
<211> LENGTH: 110
<212> TYPE: PRT
<213> ORGANISM: Artificial Sequence
<220> FEATURE:
<223> OTHER INFORMATION: 299-012 VL humanization variant_HYS

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ser Ser Asn
                85                  90                  95

Val Asp Asn Thr Phe Gly Gly Gly Thr Lys Val Glu Ile Lys
            100                 105                 110

<210> SEQ ID NO 44
<211> LENGTH: 110
<212> TYPE: PRT
<213> ORGANISM: Artificial Sequence
<220> FEATURE:
<223> OTHER INFORMATION: 299-014 VL humanization variant

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Ser Tyr Ser Ser Ser Asn
                85                  90                  95

Val Asp Asn Thr Phe Gly Gly Gly Thr Lys Val Glu Ile Lys
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: 299-015 VL humanization variant_AYS

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Ser Ser Tyr
            20                  25                  30

Leu Ile Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Ala Tyr Ser Ser Ser Asn
                85                  90                  95

Val Asp Asn Thr Phe Gly Gly Gly Thr Lys Val Glu Ile Lys
            100                 105                 110

<210> SEQ ID NO 46
<211> LENGTH: 110
<212> TYPE: PRT
<213> ORGANISM: Artificial Sequence
<220> FEATURE:
<223> OTHER INFORMATION: 299-017 VL humanization variant_TYS

<400> SEQUENCE: 46

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ser Ser Asn
                85                  90                  95

Val Asp Asn Thr Phe Gly Gly Gly Thr Lys Val Glu Ile Lys
            100                 105                 110

<210> SEQ ID NO 47
<211> LENGTH: 119
<212> TYPE: PRT
<213> ORGANISM: Mus musculus

<400> SEQUENCE: 47

Glu Val Gln Leu Gln Gln Ser Gly Ala Val Leu Val Lys Pro Gly Ala
1               5                   10                  15

Ser Val Lys Leu Ser Cys Pro Ala Ser Gly Phe Asn Ile Lys Asp Thr
            20                  25                  30

Tyr Ile His Trp Val Gln Arg Pro Glu Gln Gly Leu Glu Trp Ile
        35                  40                  45

Gly Arg Ile Asp Pro Ala Asn Gly Asp Thr Lys Cys Asp Pro Lys Phe
    50                  55                  60

Gln Val Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Val Arg Asp Tyr Leu Tyr Pro Tyr Phe Asp Phe Trp Gly Gln Gly
            100                 105                 110

Thr Thr Leu Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: 494 VH variant D52A

<400> SEQUENCE: 48

```
Glu Val Gln Leu Gln Gln Ser Gly Ala Val Leu Val Lys Pro Gly Ala
1               5                   10                  15

Ser Val Lys Leu Ser Cys Pro Ala Ser Gly Phe Asn Ile Lys Asp Thr
            20                  25                  30

Tyr Ile His Trp Val Ile Gln Arg Pro Glu Gln Gly Leu Glu Trp Ile
        35                  40                  45

Gly Arg Ile Ala Pro Ala Asn Gly Asp Thr Lys Ser Asp Pro Lys Phe
    50                  55                  60

Gln Val Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Val Arg Asp Tyr Leu Tyr Pro Tyr Tyr Phe Asp Phe Trp Gly Gln Gly
                100                 105                 110

Thr Thr Leu Thr Val Ser Ser
            115
```

<210> SEQ ID NO 49
<211> LENGTH: 119
<212> TYPE: PRT
<213> ORGANISM: Artificial Sequence
<220> FEATURE:
<223> OTHER INFORMATION: 494 VH variant D52L

<400> SEQUENCE: 49

```
Glu Val Gln Leu Gln Gln Ser Gly Ala Val Leu Val Lys Pro Gly Ala
1               5                   10                  15

Ser Val Lys Leu Ser Cys Pro Ala Ser Gly Phe Asn Ile Lys Asp Thr
            20                  25                  30

Tyr Ile His Trp Val Ile Gln Arg Pro Glu Gln Gly Leu Glu Trp Ile
        35                  40                  45

Gly Arg Ile Leu Pro Ala Asn Gly Asp Thr Lys Ser Asp Pro Lys Phe
    50                  55                  60

Gln Val Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Val Arg Asp Tyr Leu Tyr Pro Tyr Tyr Phe Asp Phe Trp Gly Gln Gly
                100                 105                 110

Thr Thr Leu Thr Val Ser Ser
            115
```

<210> SEQ ID NO 50
<211> LENGTH: 119
<212> TYPE: PRT
<213> ORGANISM: Artificial Sequence
<220> FEATURE:
<223> OTHER INFORMATION: 494 VH variant D31G

<400> SEQUENCE: 50

```
Glu Val Gln Leu Gln Gln Ser Gly Ala Val Leu Val Lys Pro Gly Ala
1               5                   10                  15

Ser Val Lys Leu Ser Cys Pro Ala Ser Gly Phe Asn Ile Lys Gly Thr
            20                  25                  30

Tyr Ile His Trp Val Ile Gln Arg Pro Glu Gln Gly Leu Glu Trp Ile
        35                  40                  45
```

```
Gly Arg Ile Asp Pro Ala Asn Gly Asp Thr Lys Ser Asp Pro Lys Phe
         50                  55                  60

Gln Val Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95

Val Arg Asp Tyr Leu Tyr Pro Tyr Tyr Phe Asp Phe Trp Gly Gln Gly
            100                 105                 110

Thr Thr Leu Thr Val Ser Ser
            115

<210> SEQ ID NO 51
<211> LENGTH: 119
<212> TYPE: PRT
<213> ORGANISM: Artificial Sequence
<220> FEATURE:
<223> OTHER INFORMATION: 494 VH variant L101A

<400> SEQUENCE: 51

Glu Val Gln Leu Gln Gln Ser Gly Ala Val Leu Val Lys Pro Gly Ala
 1               5                  10                  15

Ser Val Lys Leu Ser Cys Pro Ala Ser Gly Phe Asn Ile Lys Asp Thr
                 20                  25                  30

Tyr Ile His Trp Val Ile Gln Arg Pro Glu Gln Gly Leu Glu Trp Ile
             35                  40                  45

Gly Arg Ile Asp Pro Ala Asn Gly Asp Thr Lys Ser Asp Pro Lys Phe
         50                  55                  60

Gln Val Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95

Val Arg Asp Tyr Ala Tyr Pro Tyr Tyr Phe Asp Phe Trp Gly Gln Gly
            100                 105                 110

Thr Thr Leu Thr Val Ser Ser
            115

<210> SEQ ID NO 52
<211> LENGTH: 119
<212> TYPE: PRT
<213> ORGANISM: Artificial Sequence
<220> FEATURE:
<223> OTHER INFORMATION: 494-001 VH humanization variant

<400> SEQUENCE: 52

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                 20                  25                  30

Tyr Ile His Trp Val Ile Gln Ala Pro Gly Gln Gly Leu Glu Trp Met
             35                  40                  45

Gly Arg Ile Asp Pro Ala Asn Gly Asp Thr Lys Ser Asp Pro Lys Phe
         50                  55                  60

Gln Val Arg Val Thr Ile Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

-continued

Val Arg Asp Tyr Leu Tyr Pro Tyr Tyr Phe Asp Phe Trp Gly Gln Gly
            100                 105                 110

Thr Thr Val Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: 494-002 VH humanization variant

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Ile Gln Ala Pro Gly Gln Gly Leu Glu Trp Met
        35                  40                  45

Gly Arg Ile Asp Pro Ala Asn Gly Asp Thr Lys Ser Ala Pro Lys Phe
    50                  55                  60

Gln Val Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Val Arg Asp Tyr Leu Tyr Pro Tyr Tyr Phe Asp Phe Trp Gly Gln Gly
            100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: 494-003 VH humanization variant

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Ile Gln Ala Pro Gly Gln Gly Leu Glu Trp Met
        35                  40                  45

Gly Arg Ile Asp Pro Ala Asn Gly Asp Thr Lys Ser Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Val Arg Asp Tyr Leu Tyr Pro Tyr Tyr Phe Asp Phe Trp Gly Gln Gly
            100                 105                 110

Thr Thr Val Thr Val Ser Ser
        115

<210> SEQ ID NO 55
<211> LENGTH: 119
<212> TYPE: PRT

<213> ORGANISM: Artificial Sequence
<220> FEATURE:
<223> OTHER INFORMATION: 494-004 VH humanization variant

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Ile His Trp Val Ile Gln Ala Pro Gly Gln Gly Leu Glu Trp Met
        35                  40                  45

Gly Arg Ile Asp Pro Ala Asn Gly Asp Thr Lys Ser Asp Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
        115
```

<210> SEQ ID NO 56
<211> LENGTH: 119
<212> TYPE: PRT
<213> ORGANISM: Artificial Sequence
<220> FEATURE:
<223> OTHER INFORMATION: 494-005 VH humanization variant

<400> SEQUENCE: 56

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Ile His Trp Val Ile Gln Arg Pro Gly Gln Gly Leu Glu Trp Met
        35                  40                  45

Gly Arg Ile Asp Pro Ala Asn Gly Asp Thr Lys Ser Asp Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
        115
```

<210> SEQ ID NO 57
<211> LENGTH: 119
<212> TYPE: PRT
<213> ORGANISM: Artificial Sequence
<220> FEATURE:
<223> OTHER INFORMATION: 494-006 VH humanization variant

<400> SEQUENCE: 57

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asn Ile Lys Asp Thr
            20                  25                  30
```

Tyr Ile His Trp Val Ile Gln Arg Pro Gly Lys Gly Leu Glu Trp Ile
            35                  40                  45

Gly Arg Ile Asp Pro Ala Asn Gly Asp Thr Lys Ser Asp Pro Ser Leu
        50                  55                  60

Gln Ser Arg Val Thr Ile Ser Ala Asp Thr Ser Lys Asn Gln Ala Ser
65                  70                  75                  80

Leu Lys Leu Ser Ser Val Thr Ala Ala Asp Thr Ala Val Tyr Tyr Cys
                85                  90                  95

Val Arg Asp Tyr Leu Tyr Pro Tyr Tyr Phe Asp Phe Trp Gly Gln Gly
                100                 105                 110

Thr Thr Val Thr Val Ser Ser
            115

<210> SEQ ID NO 58
<211> LENGTH: 119
<212> TYPE: PRT
<213> ORGANISM: Artificial Sequence
<220> FEATURE:
<223> OTHER INFORMATION: 494-007 VH humanization variant

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Ile Gln Ala Pro Gly Lys Gly Leu Glu Trp Val
            35                  40                  45

Gly Arg Ile Asp Pro Ala Asn Gly Asp Thr Lys Ser Asp Pro Ser Val
        50                  55                  60

Gln Val Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Tyr Leu Tyr Pro Tyr Tyr Phe Asp Phe Trp Gly Gln Gly
                100                 105                 110

Thr Thr Val Thr Val Ser Ser
            115

<210> SEQ ID NO 59
<211> LENGTH: 107
<212> TYPE: PRT
<213> ORGANISM: Mus musculus

<400> SEQUENCE: 59

Lys Ile Val Met Thr Gln Ser Pro Lys Ser Met Ser Met Ser Val Gly
1               5                   10                  15

Glu Arg Val Thr Leu Asn Cys Arg Ala Ser Glu Ser Val Asp Thr Tyr
            20                  25                  30

Val Ser Trp Tyr Gln Gln Lys Pro Glu Gln Ser Pro Glu Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Thr Tyr Asn Tyr Pro Leu
                85                  90                  95

Thr Phe Gly Ala Gly Thr Lys Leu Glu Leu Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: 494-001 VL humanization variant

<400> SEQUENCE: 60

Lys Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gly Gln Thr Tyr Asn Tyr Pro Leu
                85                  90                  95

Thr Phe Gly Gln Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: 494-002 VL humanization variant

<400> SEQUENCE: 61

Lys Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Thr Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Asp Tyr Tyr Cys Gly Gln Thr Tyr Asn Tyr Pro Leu
                85                  90                  95

Thr Phe Gly Gln Gly Thr Lys Leu Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: 494-003 VL humanization variant

<400> SEQUENCE: 62

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Glu Ser Val Asp Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Thr Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Asp Tyr Tyr Cys Gln Thr Tyr Asn Tyr Pro Leu
                85                  90                  95

Thr Phe Gly Gln Gly Thr Lys Leu Glu Ile Lys
            100                 105
```

<210> SEQ ID NO 63
<211> LENGTH: 107
<212> TYPE: PRT
<213> ORGANISM: Artificial Sequence
<220> FEATURE:
<223> OTHER INFORMATION: 494-004 VL humanization variant

<400> SEQUENCE: 63

```
Lys Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Asp Tyr Tyr Cys Gln Thr Tyr Asn Tyr Pro Leu
                85                  90                  95

Thr Phe Gly Gln Gly Thr Lys Leu Glu Ile Lys
            100                 105
```

<210> SEQ ID NO 64
<211> LENGTH: 118
<212> TYPE: PRT
<213> ORGANISM: Mus musculus

<400> SEQUENCE: 64

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
        35                  40                  45

Gly Arg Ile Asn Pro His Asn Gly Gly Thr Asp Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Tyr Tyr Ser Leu Asp Tyr Trp Gly Gln Gly Thr
            100                 105                 110
```

```
Leu Val Thr Val Ser Ser
        115

<210> SEQ ID NO 65
<211> LENGTH: 106
<212> TYPE: PRT
<213> ORGANISM: Mus musculus

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ile Arg Tyr Ile
            20                  25                  30

His Trp Tyr Gln Gln Lys Pro Gly Lys Ala Pro Lys Arg Leu Ile Tyr
            35                  40                  45

Asp Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Arg Asn Ser Tyr Pro Trp Thr
                85                  90                  95

Phe Gly Gln Gly Thr Arg Leu Glu Ile Lys
            100                 105

<210> SEQ ID NO 66
<211> LENGTH: 7
<212> TYPE: PRT
<213> ORGANISM: Oryctolagus cuniculus

<400> SEQUENCE: 66

Gly Phe Ser Leu Ser Ser Tyr
1               5

<210> SEQ ID NO 67
<211> LENGTH: 5
<212> TYPE: PRT
<213> ORGANISM: Oryctolagus cuniculus

<400> SEQUENCE: 67

Ser Tyr Ala Met Ser
1               5

<210> SEQ ID NO 68
<211> LENGTH: 5
<212> TYPE: PRT
<213> ORGANISM: Oryctolagus cuniculus

<400> SEQUENCE: 68

Trp Ser Gly Gly Ser
1               5

<210> SEQ ID NO 69
<211> LENGTH: 16
<212> TYPE: PRT
<213> ORGANISM: Oryctolagus cuniculus

<400> SEQUENCE: 69

Tyr Ile Trp Ser Gly Gly Ser Thr Asp Tyr Ala Ser Trp Ala Lys Gly
1               5                   10                  15

<210> SEQ ID NO 70
<211> LENGTH: 16
```

```
<212> TYPE: PRT
<213> ORGANISM: Artificial Sequence
<220> FEATURE:
<223> OTHER INFORMATION: 299-000 HVR-H2 Kabat G65S

<400> SEQUENCE: 70

Tyr Ile Trp Ser Gly Gly Ser Thr Asp Tyr Ala Ser Trp Ala Lys Ser
1               5                   10                  15

<210> SEQ ID NO 71
<211> LENGTH: 17
<212> TYPE: PRT
<213> ORGANISM: Oryctolagus cuniculus

<400> SEQUENCE: 71

Arg Tyr Gly Thr Ser Tyr Pro Asp Tyr Gly Asp Ala Asn Gly Phe Asp
1               5                   10                  15
Pro

<210> SEQ ID NO 72
<211> LENGTH: 17
<212> TYPE: PRT
<213> ORGANISM: Artificial Sequence
<220> FEATURE:
<223> OTHER INFORMATION: 299-000 HVR-H3 DASG

<400> SEQUENCE: 72

Arg Tyr Gly Thr Ser Tyr Pro Asp Tyr Gly Asp Ala Ser Gly Phe Asp
1               5                   10                  15
Pro

<210> SEQ ID NO 73
<211> LENGTH: 17
<212> TYPE: PRT
<213> ORGANISM: Artificial Sequence
<220> FEATURE:
<223> OTHER INFORMATION: 299-000 HVR-H3 DAQG

<400> SEQUENCE: 73

Arg Tyr Gly Thr Ser Tyr Pro Asp Tyr Gly Asp Ala Gln Gly Phe Asp
1               5                   10                  15
Pro

<210> SEQ ID NO 74
<211> LENGTH: 11
<212> TYPE: PRT
<213> ORGANISM: Oryctolagus cuniculus

<400> SEQUENCE: 74

Gln Ala Ser Gln Ser Ile Ser Ser Tyr Leu Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: 299-000 HVR-L1 RAA

<400> SEQUENCE: 75

Arg Ala Ser Gln Ser Ile Ser Ser Tyr Leu Ala
1               5                   10

<210> SEQ ID NO 76
```

-continued

```
<211> LENGTH: 7
<212> TYPE: PRT
<213> ORGANISM: Oryctolagus cuniculus

<400> SEQUENCE: 76

Arg Ala Ser Thr Leu Ala Ser
1               5

<210> SEQ ID NO 77
<211> LENGTH: 12
<212> TYPE: PRT
<213> ORGANISM: Oryctolagus cuniculus

<400> SEQUENCE: 77

Gln Gln Cys Tyr Ser Ser Ser Asn Val Asp Asn Thr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: 299-000 HVR-L3 NYA

<400> SEQUENCE: 78

Gln Gln Asn Tyr Ala Ser Ser Asn Val Asp Asn Thr
1               5                   10

<210> SEQ ID NO 79
<211> LENGTH: 119
<212> TYPE: PRT
<213> ORGANISM: Artificial Sequence
<220> FEATURE:
<223> OTHER INFORMATION: anti-CD20 antibody VH

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 80
<211> LENGTH: 112
<212> TYPE: PRT
<213> ORGANISM: Artificial Sequence
<220> FEATURE:
<223> OTHER INFORMATION: anti-CD20 antibody VL

<400> SEQUENCE: 80

Asp Ile Val Met Thr Gln Thr Pro Leu Ser Leu Pro Val Thr Pro Gly
1               5                   10                  15
```

```
Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 81
<211> LENGTH: 126
<212> TYPE: PRT
<213> ORGANISM: Homo sapiens

<400> SEQUENCE: 81

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser
        115                 120                 125
```

<210> SEQ ID NO 82
<211> LENGTH: 108
<212> TYPE: PRT
<213> ORGANISM: Homo sapiens

<400> SEQUENCE: 82

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys
            100                 105
```

<210> SEQ ID NO 83
<211> LENGTH: 116
<212> TYPE: PRT
<213> ORGANISM: Artificial Sequence
<220> FEATURE:
<223> OTHER INFORMATION: humanized anti-alpha synuclein acntibody 9E4 VH

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 84
<211> LENGTH: 113
<212> TYPE: PRT
<213> ORGANISM: Artificial Sequence
<220> FEATURE:
<223> OTHER INFORMATION: humanized anti-alpha synuclein acntibody 9E4 VL

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 85
<211> LENGTH: 115
<212> TYPE: PRT
<213> ORGANISM: Mus musculus

<400> SEQUENCE: 85

Gln Val Gln Leu Gln Gln Ser Gly Ala Glu Leu Ala Lys Pro Gly Thr
1               5                   10                  15

```
Ser Val Gln Met Ser Cys Lys Ala Ser Gly Tyr Thr Phe Thr Asn Tyr
            20                  25                  30

Trp Met Asn Trp Ile Lys Ala Arg Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Lys Ala Ile Leu Thr Ala Asp Lys Ser Ser Asn Thr Ala Tyr
65                  70                  75                  80

Met His Leu Ser Ser Leu Thr Ser Glu Asp Ser Ala Val Tyr Phe Cys
            85                  90                  95

Ala Ser Gly Gly His Leu Ala Tyr Trp Gly Gln Gly Thr Val Val Thr
            100                 105                 110

Val Ser Ala
        115
```

```
<210> SEQ ID NO 86
<211> LENGTH: 112
<212> TYPE: PRT
<213> ORGANISM: Mus musculus

<400> SEQUENCE: 86

Asp Val Val Met Thr Gln Ile Pro Leu Tyr Leu Ser Val Ser Pro Gly
1               5                   10                  15

Asp Gln Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Phe Cys Ser Gln Ser
            85                  90                  95

Ala His Val Pro Trp Thr Phe Gly Gly Gly Thr Lys Leu Glu Ile Arg
            100                 105                 110
```

```
<210> SEQ ID NO 87
<211> LENGTH: 115
<212> TYPE: PRT
<213> ORGANISM: Mus musculus

<400> SEQUENCE: 87

Val Gln Leu Gln Gln Ser Gly Pro Glu Leu Val Lys Pro Gly Thr Ser
1               5                   10                  15

Val Lys Ile Ser Cys Lys Ala Ser Gly Tyr Ser Phe Thr Ser Tyr Tyr
            20                  25                  30

Ile His Trp Val Lys Gln Ser Pro Gly Gln Gly Leu Glu Trp Ile Gly
        35                  40                  45

Trp Ile Tyr Pro Gly Ser Gly Asn Thr Lys Tyr Ser Glu Lys Phe Lys
    50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
            85                  90                  95

Arg Asp Gly Cys Tyr Gly Phe Ala Tyr Trp Gly Gln Gly Thr Leu Val
            100                 105                 110
```

Thr Val Ser
        115

<210> SEQ ID NO 88
<211> LENGTH: 111
<212> TYPE: PRT
<213> ORGANISM: Mus musculus

<400> SEQUENCE: 88

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Phe Leu Ile Cys Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
            100                 105                 110

<210> SEQ ID NO 89
<211> LENGTH: 115
<212> TYPE: PRT
<213> ORGANISM: Oryctolagus cuniculus

<400> SEQUENCE: 89

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Ile Asn Ser Tyr Ala
            20                  25                  30

Met Ile Trp Val Arg Gln Ala Pro Gly Glu Gly Leu Glu Trp Ile Gly
        35                  40                  45

Val Ile Tyr Pro Ser Gly Asn Thr Tyr Tyr Ala Asn Trp Ala Lys Gly
    50                  55                  60

Arg Phe Thr Val Ser Arg Thr Ser Thr Thr Val Asp Leu Lys Ile Thr
65                  70                  75                  80

Ser Pro Thr Thr Glu Asp Thr Ala Thr Tyr Phe Cys Ala Arg Arg Asp
                85                  90                  95

Gly Thr Asp Lys Thr Phe Asn Ile Trp Gly Pro Gly Thr Leu Val Thr
            100                 105                 110

Val Ser Leu
        115

<210> SEQ ID NO 90
<211> LENGTH: 112
<212> TYPE: PRT
<213> ORGANISM: Oryctolagus cuniculus

<400> SEQUENCE: 90

Gln Val Leu Thr Gln Thr Pro Ser Pro Val Ser Ala Ala Val Gly Gly
1               5                   10                  15

Thr Val Thr Ile Asn Cys Gln Ala Ser Gln Asn Val Tyr Gly Asp Asn
            20                  25                  30

Tyr Leu Ala Trp Tyr Gln Gln Lys Pro Gly Gln Pro Pro Lys Leu Leu
                35                  40                  45

Ile Tyr Glu Ala Ser Lys Leu Ala Ser Gly Val Pro Pro Arg Phe Ser
 50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Gln Gly Glu Phe Leu Cys Thr
                 85                  90                  95

Thr Ser Asp Cys Phe Thr Phe Gly Gly Gly Thr Gly Val Val Val Arg
                100                 105                 110

<210> SEQ ID NO 91
<211> LENGTH: 119
<212> TYPE: PRT
<213> ORGANISM: Oryctolagus cuniculus

<400> SEQUENCE: 91

Gln Ser Val Glu Glu Ser Gly Gly Arg Leu Val Thr Pro Gly Thr Pro
 1               5                  10                  15

Leu Thr Leu Thr Cys Thr Val Ser Gly Ile Asp Leu Ser Arg Tyr Ala
                20                  25                  30

Met Ser Trp Val Arg Gln Ala Pro Gly Lys Gly Leu Glu Trp Ile Gly
                35                  40                  45

Val Ile Asn Ser Ser Gly Ala Thr Tyr Tyr Ala Ser Trp Ala Lys Gly
 50                  55                  60

Arg Phe Thr Ile Ser Glu Thr Ser Thr Thr Val Glu Leu Lys Ile Thr
 65                  70                  75                  80

Ser Pro Thr Thr Glu Asp Thr Ala Thr Tyr Phe Cys Ala Arg Trp Thr
                 85                  90                  95

Tyr Asp Asp Tyr Gly Asp Phe Gln Gly Phe Asn Ile Trp Gly Pro Gly
                100                 105                 110

Thr Leu Val Thr Val Ser Leu
            115

<210> SEQ ID NO 92
<211> LENGTH: 111
<212> TYPE: PRT
<213> ORGANISM: Oryctolagus cuniculus

<400> SEQUENCE: 92

Ala Val Leu Thr Gln Thr Pro Ser Pro Val Ser Ala Ala Val Gly Gly
 1               5                  10                  15

Thr Val Thr Ile Ser Cys Gln Ser Ser Gln Ser Val Tyr Asn Asn Asn
                20                  25                  30

Asp Leu Ala Trp Tyr Gln Gln Lys Pro Gly Gln Pro Pro Lys Leu Leu
                35                  40                  45

Ile Tyr Arg Ala Ser Lys Leu Ala Ser Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Gly Tyr Asp Asp Asp
                 85                  90                  95

Ala Asp Met Gly Ala Phe Gly Gly Gly Thr Glu Val Val Val Lys
                100                 105                 110

<210> SEQ ID NO 93

<211> LENGTH: 111
<212> TYPE: PRT
<213> ORGANISM: Artificial Sequence
<220> FEATURE:
<223> OTHER INFORMATION: heavy chain variable domain

<400> SEQUENCE: 93

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Asp Thr
            20                  25                  30

Met Ile Trp Val Arg Gln Ala Pro Gly Glu Gly Leu Glu Trp Ile Gly
        35                  40                  45

Ser Ile Tyr Thr Asp Ser Gly Asn Thr Trp Tyr Ala Ser Trp Val Lys
    50                  55                  60

Gly Arg Phe Thr Ile Ser Lys Thr Ser Ser Thr Val Asp Leu Arg
65                  70                  75                  80

Ile Thr Ser Pro Thr Thr Glu Asp Thr Ala Thr Tyr Phe Cys Ala Arg
                85                  90                  95

Asn Phe Ser Val Trp Gly Pro Gly Thr Leu Val Thr Val Ser Leu
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: light chain variable domain

<400> SEQUENCE: 94

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Asn Ser Asp
            20                  25                  30

Arg Leu Ala Trp Phe Gln Gln Met Arg Gly Gln Pro Pro Lys Leu Leu
        35                  40                  45

Ile Tyr Asp Val Ser Lys Leu Ala Ser Gly Val Pro Ser Arg Phe Ser
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Asp Cys Ser
                85                  90                  95

Ser Ala Glu Cys Asn Val Phe Gly Gly Gly Thr Glu Val Val Val Lys
            100                 105                 110

<210> SEQ ID NO 95
<211> LENGTH: 20
<212> TYPE: PRT
<213> ORGANISM: Artificial Sequence
<220> FEATURE:
<223> OTHER INFORMATION: peptidic linker

<400> SEQUENCE: 95

Gly Gly Gly Gly Ser Gly Gly Gly Gly Ser Gly Gly Gly Gly Ser Gly
1               5                   10                  15

Gly Gly Gly Ser
            20

<210> SEQ ID NO 96
<211> LENGTH: 32

```
<212> TYPE: PRT
<213> ORGANISM: Artificial Sequence
<220> FEATURE:
<223> OTHER INFORMATION: peptidic linker

<400> SEQUENCE: 96

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20              25              30

<210> SEQ ID NO 97
<211> LENGTH: 536
<212> TYPE: PRT
<213> ORGANISM: Homo sapiens

<400> SEQUENCE: 97

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
290                 295                 300
```

```
Pro Thr Leu Ala Asn Ser Thr His His Asn Val Arg Leu Leu Met Leu
305                 310                 315                 320

Asp Asp Gln Arg Leu Leu Pro His Trp Ala Lys Val Val Leu Thr
            325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
        450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
        530                 535
```

ANTI-TRANSFERRIN RECEPTOR ANTIBODIES WITH TAILORED AFFINITY

CROSS REFERENCE TO RELATED APPLICATIONS

This application is a continuation of U.S. patent application Ser. No. 15/847,448, filed on Dec. 19, 2017, which is a continuation of International Application No. PCT/EP2016/064460, having an International Filing Date of Jun. 22, 2016, and which claims the benefit of priority to EP 15173508.1, filed Jun. 24, 2015, and EP 15176084.0, filed Jul. 9, 2015, the entire contents of which are incorporated herein by reference.

SEQUENCE LISTING

This application contains a Sequence Listing submitted via EFS-Web and hereby incorporated by reference in its entirety. Said ASCII copy, created on Apr. 22, 2019, is named P32937-US-1_sequencelisting.txt, and is 97,964 bytes in size.

FIELD OF THE INVENTION

The present invention relates to an anti-transferrin receptor antibodies with designed off-rates for the human transferrin receptor and their use as blood-brain-barrier shuttle module.

BACKGROUND

Brain penetration of neurological disorder drugs such as e.g. large biotherapeutic drugs or small molecule drugs having a low brain penetration, is strictly limited by the extensive and impermeable blood-brain-barrier (BBB) together with the other cell component in the neurovascular unit (NVU). Many strategies to overcome this obstacle have been tested and one is to utilize transcytosis pathways mediated by endogenous receptors expressed on the brain capillary endothelium (blood-brain-barrier-receptor). Recombinant proteins such as monoclonal antibodies or peptides have been designed against these receptors to enable receptor-mediated delivery of biotherapeutics to the brain. However, strategies to maximize brain uptake while minimizing miss-sorting within the brain endothelial cells (BECs), and the extent of accumulation within certain organelles (especially organelles that leads to degradation of the biotherapeutic) in BECs, remain unexplored.

Monoclonal antibodies and other biotherapeutics have huge therapeutic potential for treatment of pathology in the central nervous system (CNS). However, their route into the brain is prevented by the BBB. Previous studies have illustrated that a very small percentage (approxim It was previously found that the percentage of the antibody that distributes into the CNS could be improved by exploiting BBB receptors (i.e., transferrin receptor, insulin receptor and the like) (see, e.g., WO 95/02421).

Therefore, there is a need for delivery systems of neurological disorder drugs across the BBB to shuttle the drugs into the brain efficiently.

In WO 2014/033074 a blood-brain-barrier shuttle is reported.

In WO 2014/189973 anti-transferrin receptor antibodies and methods of use are reported. It is further reported that targeting a BBB receptor with a traditional specific high-affinity antibody generally resulted in limited increase in BBB transport. It was later found that the magnitude of antibody uptake into and distribution in the CNS is inversely related to its binding affinity for the BBB receptor amongst the anti-BBB antibodies studied. For example, a low-affinity antibody to transferrin receptor (TfR) dosed at therapeutic dose levels greatly improves BBB transport and CNS retention of the anti-TfR antibody relative to a higher-affinity anti-TfR antibody, and makes it possible to more readily attain therapeutic concentrations in the CNS (Atwal et al., Sci. Transl. Med. 3 (2011) 84ra43). Proof of such BBB transport was achieved using a bispecific antibody that binds both TfR and the amyloid precursor protein (APP) cleavage enzyme, (3-secretase (BACE1). A single systemic dose of the bispecific anti-TfR/BACE1 antibody engineered using a low-affinity antibody not only resulted in significant antibody uptake in brain, but also dramatically reduced levels of brain Aβ1-40 compared to monospecific anti-BACE1 alone, suggesting that BBB penetrance affects the potency of anti-BACE1 (Atwal et al., Sci. Transl. Med. 3 (2011) 84ra43; Yu et al., Sci. Transl. Med. 3 (2011) 84ra44).

Further a thorough nonclinical safety evaluation of monoclonal antibodies (mAbs) intended for therapeutic application is very important due to the increasing complexity of antibody engineering aspects and the variability induced by the diversity of recombinant production cell systems for generation of antibodies. Furthermore, their complex structure, unique biologic functions and the longer half-lives of mAbs compared with traditional small molecule drugs add to the safety considerations in addition to concerns due to prolonged clinical use of mAbs for the treatment of chronic diseases (Lynch, C. M., et al., mAbs 1 (2009) 2-11; Kim, S. J., et al., Mol. Cells 20 (2005) 17-29).

The overall goal of the nonclinical studies for mAbs is to define the toxicological properties of the mAb in question and provide information for product development. The main objectives of the nonclinical evaluation are (1) identification of target organs for toxicity and to determine whether the toxicity is reversible following the treatment, (2) identification of a safe starting dose for human Phase I clinical trials and subsequent dose escalation schemes, (3) provide information to monitor safety parameters in the clinical trials and (4) provide safety data to support claims on the product label. In order to achieve these goals, both in vitro and in vivo nonclinical studies aimed at defining and understanding the pharmacological properties of the antibody are conducted (Lynch, C. M., et al., mAbs 1 (2009) 2-11; Cavagnaro, J. A., In: Cavagnaro, J. A. (Ed.) "Preclinical safety evaluation of biopharmaceuticals"; Hoboken, N.J.: Wiley 2008; 45-65).

For successful nonclinical safety evaluation of a mAb, the most relevant animal species should be chosen for toxicity testing (Lynch, C. M., et al., mAbs 1 (2009) 2-11; Chapman, K., et al., Nat. Rev. Drug Discov. 6 (2007) 120-126). A relevant species is one in which the antibody is pharmacologically active, the target antigen should be present or expressed and tissue cross-reactivity profile should be similar to humans (Lynch, C. M., et al., mAbs 1 (2009) 2-11; Chapman, K., et al., Nat. Rev. Drug Discov. 6 (2007) 120-126; Subramanyam, M. and Mertsching, E., In: Cavagnaro J. A. (Ed.); Preclinical safety evaluation of biopharmaceuticals. Hoboken, N.J.: Wiley 2008; 181-205; Hall, W.

C., et al., In: Cavagnaro, J. A. (Ed.); Preclinical safety evaluation of biopharmaceuticals. Hoboken, N.J.: Wiley 2008; 207-240). Using immunochemical or functional assays, a relevant animal species that expresses the desired epitope and demonstrates a tissue cross-reactivity profile similar to human tissues can be identified (Lynch, C. M., et al., mAbs 1 (2009) 2-11; Hall, W. C., et al., In: Cavagnaro, J. A. (Ed.); Preclinical safety evaluation of biopharmaceuticals. Hoboken, N.J.: Wiley 2008; 207-240). Species cross-reactivity studies, which are useful in this process, involve an immunohistochemical survey of tissues from a variety of species using commercially available multi-species tissue microarrays (Lynch, C. M., et al., mAbs 1 (2009) 2-11; Hall, W. C., et al., In: Cavagnaro, J. A. (Ed.); Preclinical safety evaluation of biopharmaceuticals. Hoboken, N.J.: Wiley 2008; 207-240). Alternatively, evaluation of antibody binding to cells from these animals by flow-activated cell sorting (FACS) is typically more sensitive than immunohistochemical analysis of tissue sections (Lynch, C. M., et al., mAbs 1 (2009) 2-11; Subramanyam, M. and Mertsching, E., In: Cavagnaro J. A. (Ed.); Preclinical safety evaluation of biopharmaceuticals. Hoboken, N.J.: Wiley 2008; 181-205). DNA and amino acid sequences of the target antigen should be compared across species; the homology between species should be determined (Lynch, C. M., et al., mAbs 1 (2009) 2-11; Subramanyam, M. and Mertsching, E., In: Cavagnaro J. A. (Ed.); Preclinical safety evaluation of biopharmaceuticals. Hoboken, N.J.: Wiley 2008; 181-205).

In addition, the biodistribution, function and structure of the antigen should be comparable between the relevant animal species and humans to allow evaluation of toxicity arising from antibody binding of the target antigen, which is referred to as on-target toxicity (Lynch, C. M., et al., mAbs 1 (2009) 2-11; 19,20). Furthermore, strong similarities in target antigen tissue distribution in the animal species and humans make it more likely that target organs of toxicity identified in animals will predict potential toxicities in humans. A lack of similarity in antigen tissue distribution between the animal species and humans does not entirely preclude use of the animal species for toxicity studies, but these differences must be taken into consideration for human risk assessment. As for antigen density or affinity, absolute equivalence between the animal model and humans is similarly not required.

Justification for the relevancy of the species selected for toxicity testing should be included in the regulatory submission. If only one species is used for safety evaluation, a summary of experiments that demonstrate the absence of additional relevant species is warranted (Lynch, C. M., et al., mAbs 1 (2009) 2-11).

If the monoclonal antibody intended for a therapeutic use does not have a species cross-reactivity either a surrogate antibody has to be used or a different species for the model. Thus, surrogate antibodies are a potential solution to the limited safety testing possible with humanized monoclonal antibodies with restricted species cross-reactivity. However, there are currently no defined criteria by which a potential surrogate antibody should be judged prior to its use in determining safety issues for the clinical agent (Regulatory Toxicology and Pharmacology Volume 40, Issue 3, December 2004, Pages 219-226).

Thus, to identify an animal model for a particular mAb the above considerations have to made. But nevertheless it is necessary that the mAb in question has a cross-reactivity with the target antigen of the test species. Otherwise even the most suitable test species cannot be used. Therefore, there is the need for mAbs that have no intra-species cross reactivity but an inter-species cross reactivity for its target in human and the species intended for non-clinical trials.

In EP 2 708 560 an antibody specifically recognising transferrin receptor is reported. In FR 2 953 841 antibodies directed against the transferrin receptor and uses thereof for immunotherapy of iron-dependent tumours are reported. In US 2009/162359 bivalent, bispecific antibodies are reported.

SUMMARY

It has been found that the anti-transferrin receptor antibodies as reported herein can be used as blood-brain-barrier shuttle module to deliver a brain effector entity across the blood-brain-barrier into the brain. In certain embodiments, the blood-brain-barrier shuttle module is a monovalent binding entity that specifically binds to the transferrin receptor. The anti-transferrin receptor antibodies as reported herein when used as blood-brain-barrier shuttle module are useful, e.g., for the diagnosis or treatment of neurological disorders, such as Alzheimer's disease, Parkinson's Disease and Alzheimer's Disease with Parkinson's Disease co-morbidity.

Reported herein are anti-transferrin receptor antibodies that specifically bind to human transferrin receptor (huTfR) and cynomolgus transferrin receptor (cyTfR). In certain embodiments, the anti-transferrin receptor antibody binds to human transferrin receptor (huTfR) and cynomolgus transferrin receptor (cyTfR);

has an off-rate for the human transferrin receptor that is equal to or less than (i.e. at most) that of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 64 and a light chain variable domain of SEQ ID NO: 65;

binds with an off-rate for the human transferrin receptor that is between and including 0.1 l/s and 0.005 l/s.

One aspect as reported herein is an anti-transferrin receptor antibody that specifically binds to human transferrin receptor and cynomolgus transferrin receptor, which comprises i) a humanized heavy chain variable domain derived from the heavy chain variable domain of SEQ ID NO: 01, and ii) a humanized light chain variable domain derived from the light chain variable domain of SEQ ID NO: 26, wherein the antibody has an off-rate for the human transferrin receptor that is equal to or less than (i.e. at most) the off-rate of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 64 and a light chain variable domain of SEQ ID NO: 65.

In one embodiment the off-rate for the human transferrin receptor is between and including 0.1 l/s and 0.005 l/s.

In one embodiment the antibody has in the light chain variable domain at position 80 a proline amino acid residue (P) (numbering according to Kabat).

In one embodiment the antibody has in the light chain variable domain at position 91 an asparagine amino acid residue (N) (numbering according to Kabat).

In one embodiment the antibody has in the light chain variable domain at position 93 an alanine amino acid residue (A) (numbering according to Kabat).

In one embodiment the antibody has in the heavy chain variable domain at position 100g a serine amino acid residue (S) (numbering according to Kabat).

In one embodiment the antibody has in the heavy chain variable domain at position 100g a glutamine amino acid residue (Q) (numbering according to Kabat).

In one embodiment the antibody has in the heavy chain variable domain at position 65 a serine amino acid residue (S) (numbering according to Kabat).

In one embodiment the antibody has in the heavy chain variable domain at position 105 a glutamine amino acid residue (Q) (numbering according to Kabat).

In one embodiment the antibody the antibody has in the light chain variable domain at position 80 a proline amino acid residue (P), in the light chain variable domain at position 91 an asparagine amino acid residue (N), in the light chain variable domain at position 93 an alanine amino acid residue (A), in the heavy chain variable domain at position 100g a serine amino acid residue (S), in the heavy chain variable domain at position 65 a serine amino acid residue (S), and in the heavy chain variable domain at position 105 a glutamine amino acid residue (Q) (numbering according to Kabat).

In one embodiment the antibody the antibody has in the light chain variable domain at position 80 a proline amino acid residue (P), in the light chain variable domain at position 91 an asparagine amino acid residue (N), in the light chain variable domain at position 93 an alanine amino acid residue (A), in the heavy chain variable domain at position 100g a glutamine amino acid residue (Q), in the heavy chain variable domain at position 65 a serine amino acid residue (S), and in the heavy chain variable domain at position 105 a glutamine amino acid residue (Q) (numbering according to Kabat).

One aspect as reported herein is an anti-transferrin receptor antibody comprising (a) a HVR-H1 comprising the amino acid sequence of SEQ ID NO: 66; (b) a HVR-H2 comprising the amino acid sequence of SEQ ID NO: 68; (c) a HVR-H3 comprising the amino acid sequence of SEQ ID NO: 71, 72 or 73; (d) a HVR-L1 comprising the amino acid sequence of SEQ ID NO: 75; (e) a HVR-L2 comprising the amino acid sequence of SEQ ID NO: 76; and (f) a HVR-L3 comprising the amino acid sequence of SEQ ID NO: 78.

In one preferred embodiment the anti-transferrin receptor antibody comprises (a) a HVR-H1 comprising the amino acid sequence of SEQ ID NO: 66; (b) a HVR-H2 comprising the amino acid sequence of SEQ ID NO: 68; (c) a HVR-H3 comprising the amino acid sequence of SEQ ID NO: 72; (d) a HVR-L 1 comprising the amino acid sequence of SEQ ID NO: 75; (e) a HVR-L2 comprising the amino acid sequence of SEQ ID NO: 76; and (f) a HVR-L3 comprising the amino acid sequence of SEQ ID NO: 78.

One aspect as reported herein is an anti-transferrin receptor antibody that specifically bind to human transferrin receptor (huTfR) comprising
i) a heavy chain variable domain (VH) sequence having at least 90% sequence identity to the amino acid sequence of SEQ ID NO: 24, and
ii) a light chain variable domain (VL) having at least 90% sequence identity to the amino acid sequence of SEQ ID NO: 37,
wherein the antibody has about the same off-rate as an antibody comprising a heavy chain variable domain (VH) sequence of SEQ ID NO: 24 and a light chain variable domain (VL) sequence of SEQ ID NO: 37.

In one embodiment the off-rate for the human transferrin receptor is between and including 0.1 l/s and 0.005 l/s.

One preferred aspect as reported herein is an anti-transferrin receptor antibody that specifically bind to human transferrin receptor (huTfR) comprising
i) a heavy chain variable domain (VH) sequence having the amino acid sequence of SEQ ID NO: 24, and
ii) a light chain variable domain (VL) having the amino acid sequence of SEQ ID NO: 37.

In one embodiment of all aspects the antibody is a multispecific antibody having at least one binding specificity for the transferrin receptor and at least one binding specificity for a therapeutic target. In one embodiment the antibody comprises a first antigen binding site which binds the transferrin receptor and a second antigen binding site which binds a brain antigen. In a further embodiment the brain antigen is selected from the group consisting of human Abeta, epidermal growth factor receptor (EGFR), human epidermal growth factor receptor 2 (HER2), human alpha-synuclein, human tau, which is phosphorylated at a tyrosine or serine residue, human CD20, amyloid precursor protein (APP), and human glucocerebrosidase. In one preferred embodiment the multispecific antibody binds both
i) the transferrin receptor and Abeta, or
ii) the transferrin receptor and CD20, or
iii) the transferrin receptor and alpha-synuclein, or
iv) the transferrin receptor and phospho-tau, or
v) the transferrin receptor and HER2, or
vi) the transferrin receptor and glucocerebrosidase.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a heavy chain variable domain of SEQ ID NO: 81 and a light chain variable domain of SEQ ID NO: 82 binding site for human Abeta.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a heavy chain variable domain of SEQ ID NO: 79 and a light chain variable domain of SEQ ID NO: 80 binding site for human CD20. In one embodiment, the heavy chain variable region comprises a replacement of the amino acid residue at Kabat position 11 with any amino acid but leucine. In one embodiment, the substitution comprises a replacement of the amino acid residue at Kabat position 11 with a nonpolar amino acid. In one preferred embodiment, the substitution comprises a replacement of the amino acid residue at Kabat position 11 in the heavy chain variable domain of SEQ ID NO: 79 with an amino acid residue selected from the group consisting of valine, leucine, isoleucine, serine, and phenylalanine.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a heavy chain variable domain of SEQ ID NO: 83 and a light chain variable domain of SEQ ID NO: 84 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 85 and a humanized light chain variable domain derived from SEQ ID NO: 86 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 87 and a humanized light chain variable domain derived from SEQ ID NO: 88 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 89 and a humanized light chain variable domain derived from SEQ ID NO: 90 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 91 and a humanized light chain variable domain derived from SEQ ID NO: 92 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 93 and a humanized light chain variable domain derived from SEQ ID NO: 94 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and a binding site for i) glucocerebrosidase that has the amino acid sequence of SEQ ID NO: 97, or ii) a functional variant of SEQ ID NO: 97 having at least 70% sequence identity, or iii) a functional variant of SEQ ID NO: 97 having one or more amino acid mutations, deletions or insertions, or iv) a truncated functional variant of SEQ ID NO: 97 having at least one amino acid residue at the N-terminus or the C-terminus or within the amino acid sequence deleted, or v) a combination of iii) and iv).

In one embodiment of all aspects the antibody comprises
  i) a homodimeric Fc-region of the human IgG1 subclass optionally with the mutations P329G, L234A and L235A, or
  ii) a homodimeric Fc-region of the human IgG4 subclass optionally with the mutations P329G, S228P and L235E, or
  iii) a heterodimeric Fc-region whereof
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
  or
  iv) a heterodimeric Fc-region of the human IgG4 subclass whereof both Fc-region polypeptides comprise the mutations P329G, L234A and L235A and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
  or
  v) a heterodimeric Fc-region of the human IgG4 subclass whereof both Fc-region polypeptides comprise the mutations P329G, S228P and L235E and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C.

In one embodiment of all aspects the antibody is a CrossMab.

One aspect as reported herein is an anti-transferrin receptor antibody comprising
  i) a heavy chain variable domain selected from the group consisting of SEQ ID NO: 52, 53, 54, 55, 56, 57 and 58, and a light chain variable domain selected from the group consisting of SEQ ID NO: 60, 61, 62 and 63,
  or
  ii) a heavy chain variable domain selected from the group consisting of SEQ ID NO: 2, 3, 4, 5, 6, 7, 8, 9, 10, 11, 12, 13, 14, 15, 16, 17, 18, 19, 20, 21, 22, 23, 24 and 25, and a light chain variable domain selected from the group consisting of SEQ ID NO: 27, 28, 29, 30, 31, 32, 33, 34, 35, 36, 37, 38, 39, 40, 41, 42, 43, 44, 45, 46 and 47.

One aspect as reported herein is a pharmaceutical formulation comprising an antibody as reported herein and a pharmaceutically acceptable carrier.

One aspect as reported herein is an antibody as reported herein for use as a medicament.

One aspect as reported herein is the use of an antibody as reported herein in the manufacture of a medicament for treating a neurological disorder.

In one embodiment the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, CNS inflammation, Alzheimer's Disease, Parkinson's Disease, multiple sclerosis, CD20 positive cancer with brain metastases, and Her2 positive cancer with brain metastases.

One aspect as reported herein is the use of an antibody as reported herein in the manufacture of a medicament for transporting one or more compounds across the blood-brain-barrier (BBB).

DESCRIPTION OF THE FIGURES

FIG. 1A is a scheme of transcytosis assay. FIG. 1B shows the transcytosis assay results for 128.1 biotin monovalent.

DETAILED DESCRIPTION OF EMBODIMENTS OF THE INVENTION

Figure 1A:
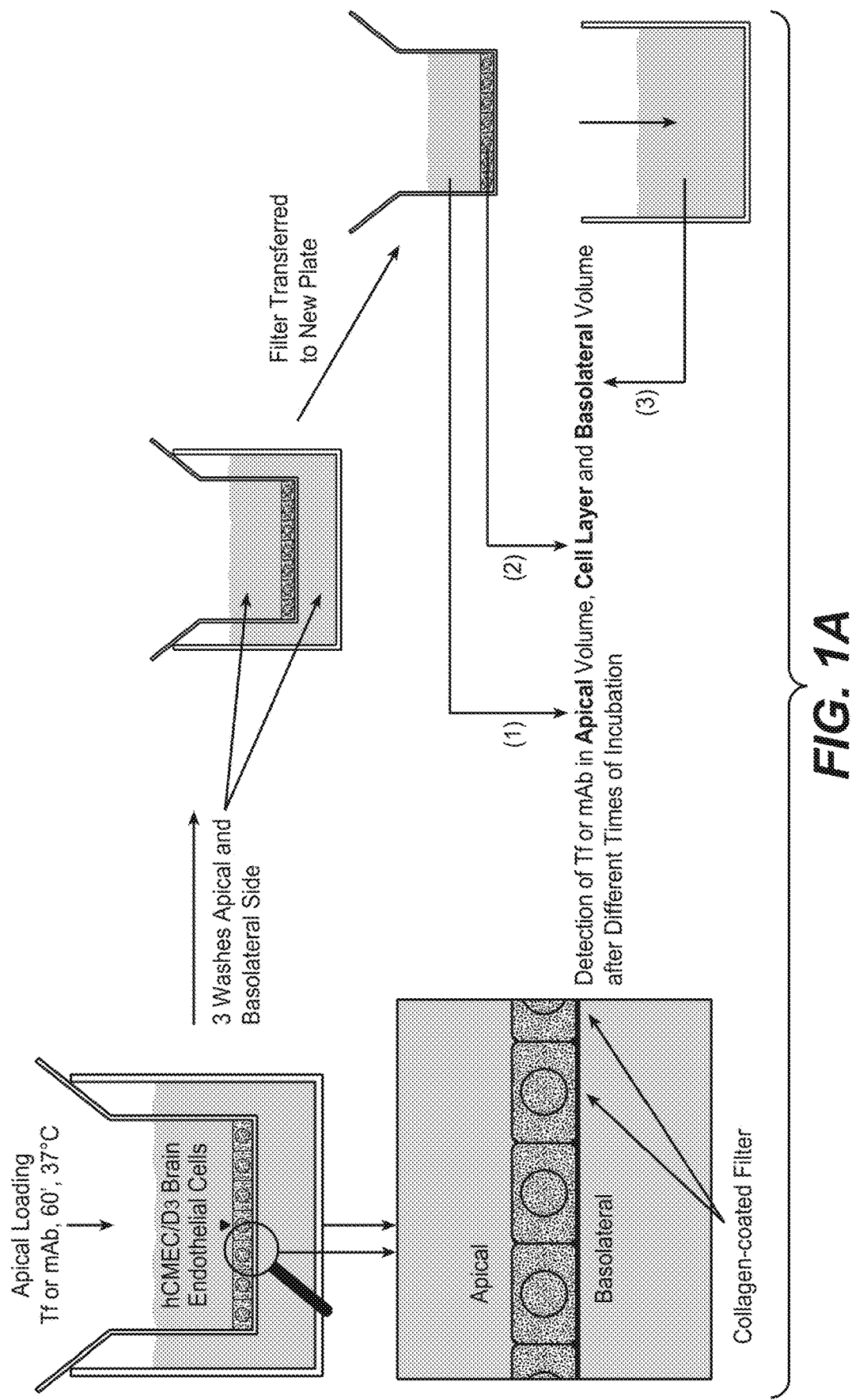
FIGS. 1A and 1B illustrate transcytosis assay.

Herein is reported a humanized variant of the rabbit antibody 299 showing high transcytosis in an transcytosis assay according to Example 8, that has cross-reactivity to human and cynomolgus transferrin receptor, i.e. specifically binds to both orthologs of the transferrin receptor, that shows good cellular staining and that has a similar half-life (mirrored by the off-rate) as the murine antibody 128.1 for the cynomolgus transferrin receptor for the human transferrin-receptor.

One aspect as reported herein is a humanized antibody that specifically binds to human transferrin receptor, wherein the antibody comprises in the heavy chain variable domain the HVRs of SEQ ID NO: 66, 68 and 72, and in the light chain variable domain the HVRs of SEQ ID NO: 75, 76 and 78.

In one embodiment the humanized antibody comprises a heavy chain variable domain of SEQ ID NO: 24 and a light chain variable domain of SEQ ID NO: 37.

In one embodiment the humanized antibody is effector function silent.

In one embodiment the humanized antibody specifically binds to human transferrin receptor and to cynomolgus transferrin receptor.

In one embodiment the humanized antibody is a) a full length antibody of the human subclass IgG1, or b) a full length antibody of the human subclass IgG4, or c) a full length antibody of the human subclass IgG1 with the mutations L234A, L235A and P329G, d) a full length antibody of the human subclass IgG4 with the mutations S228P, L235E and optionally P329G, e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or f) a full length antibody of the human subclass IgG4 with the mutations S228P, L235E and optionally P329G in both heavy chains and the mutations T366W and S354C in one heavy chain and the mutations T366S, L368A, Y407V and Y349C in the respective other heavy chain.

One aspect as reported herein is a bispecific antibody comprising i) a first binding site comprising a heavy chain variable domain of SEQ ID NO: 24 and a light chain variable domain of SEQ ID NO: 37, and ii) a second binding site selected from a) a heavy chain variable domain of SEQ ID NO: 81 and a light chain variable domain of SEQ ID NO: 82, or b) a heavy chain variable domain of SEQ ID NO: 83 and a light chain variable domain of SEQ ID NO: 84, or c) a heavy chain variable domain of SEQ ID NO: 85 and a light chain variable domain of SEQ ID NO: 86, or d) a heavy chain variable domain of SEQ ID NO: 87 and a light chain variable domain of SEQ ID NO: 88, or e) a heavy chain variable domain of SEQ ID NO: 91 and a light chain variable domain of SEQ ID NO: 92, or f) a heavy chain variable domain of SEQ ID NO: 89 and a light chain variable domain of SEQ ID NO: 90, or g) a heavy chain variable domain of SEQ ID NO: 93 and a light chain variable domain of SEQ ID NO: 94, or h) a heavy chain variable domain of SEQ ID NO: 79 and a light chain variable domain of SEQ ID NO: 80.

One aspect as reported herein is a pharmaceutical formulation comprising the antibody according as reported herein and optionally a pharmaceutically acceptable carrier.

One aspect as reported herein is an antibody as reported herein for use as a medicament.

One aspect as reported herein is an antibody as reported herein for use in the treatment of a neurological disorder.

One aspect as reported herein is the use of an antibody as reported herein in the manufacture of a medicament.

One aspect as reported herein is a method of treatment comprising administering an antibody as reported herein for treating a neurological disorder.

I. DEFINITIONS

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
  (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
  (b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);
  (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628). The numbering of the amino acid residues in the variable region (light chain and heavy chain variable region) will be done according to Kabat (Kabat, E. A. et al., Sequences of Proteins of Immunological Interest, 5th ed., Bethesda Md. (1991), NIH Publication 91-3242, Vols. 1-3).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "blood-brain-barrier" (BBB) denotes the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal cord barrier within the spinal cord, and the blood-retinal barrier within the retina are contiguous capillary barriers within the CNS, and are herein collectively referred to an the blood-brain-barrier or BBB. The BBB also encompasses the blood-CSF barrier (choroid plexus) where the barrier is comprised of ependymal cells rather than capillary endothelial cells.

The term "central nervous system" (CNS) denotes the complex of nerve tissues that control bodily function, and includes the brain and spinal cord.

The term "blood-brain-barrier-receptor" (BBBR) denotes an extracellular membrane-linked receptor protein expressed on brain endothelial cells which is capable of transporting molecules across the BBB or be used to transport exogenous administrated molecules. Examples of BBBR include but are not limited to transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). An exemplary BBBR is the transferrin receptor (TfR).

The term "brain effector entity" denotes a molecule that is to be transported to the brain across the BBB. The effector entity typically has a characteristic therapeutic activity that is desired to be delivered to the brain. Effector entities include neurologically disorder drugs and cytotoxic agents such as e.g. polypeptides and antibodies, in particular monoclonal antibodies or fragments thereof directed to a brain target.

The term "monovalent binding entity" denotes a molecule able to bind specifically and in a monovalent binding mode to a BBBR. The blood brain shuttle module and/or conjugate as reported herein are characterized by the presence of a single unit of a monovalent binding entity i.e. the blood brain shuttle module and/or conjugate of the present invention comprise exactly one unit of the monovalent binding entity. The monovalent binding entity includes but is not limited to polypeptides, full length antibodies, antibody fragments including Fab, Fab', Fv fragments, single-chain antibody molecules such as e.g. single chain Fab, scFv. The monovalent binding entity can for example be a scaffold protein engineered using state of the art technologies like phage display or immunization. The monovalent binding entity can also be a polypeptide. In certain embodiments, the monovalent binding entity comprises a CH2-CH3 Ig domain and a single chain Fab (scFab) directed to a blood-brain-barrier-receptor. The scFab is coupled to the C-terminal end of the CH2-CH3 Ig domain by a linker. In certain embodiments, the scFab is directed to the transferrin receptor.

The term "monovalent binding mode" denotes a specific binding to the BBBR where the interaction between the monovalent binding entity and the BBBR takes place through one single epitope. The monovalent binding mode prevents any dimerization/multimerization of the BBBR due to a single epitope interaction point. The monovalent binding mode prevents that the intracellular sorting of the BBBR is altered.

The term "epitope" denotes any polypeptide determinant capable of specific binding to an antibody. In certain embodiments, epitope determinants include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "transferrin receptor" (TfR) is a transmembrane glycoprotein (with a molecular weight of about 180,000 Da) which is composed of two disulfide-bonded sub-units (each of apparent molecular weight of about 90,000 Da) and is involved in iron uptake in vertebrates. In one embodiment, the TfR herein is human TfR comprising the amino acid sequence as reported in Schneider et al. (Nature 311 (1984) 675-678).

The term "imaging agent" denotes a compound that has one or more properties that permit its presence and/or location to be detected directly or indirectly. Examples of such imaging agents include proteins and small molecule compounds incorporating a labeled entity that permits detection.

The terms "CNS antigen" and "brain target" denote an antigen and/or molecule expressed in the CNS, including the brain, which can be targeted with an antibody or small molecule. Examples of such antigen and/or molecule include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), glucocerebrosidase and caspase 6.

The term "that specifically binds" denotes an antibody selectively or preferentially binding to an antigen. The binding affinity is generally determined using a standard assay, such as Scatchard analysis, or surface plasmon resonance technique (e.g. using BIACORE®).

The term "CH2-CH3 Ig entity" as used herein refers to a protein entity derived from immunoglobulin CH2 or CH3 domains. The "CH2-CH3 Ig entity" comprises two "CH2-CH3" polypeptides forming a dimer. The immunoglobulin can be IgG, IgA, IgD, IgE or IgM. In one embodiment, the CH2-CH3 Ig entity derived from an IgG immunoglobulin and is referred to herein as "CH2-CH3 IgG entity". The term includes native sequence of CH2-CH3 domains and variant CH2-CH3 domains. In one embodiment, the "CH2-CH3 Ig entity" derives from human heavy chain CH2-CH3 IgG domain which extends from Cys226, or from Pro230, to the carboxyl-terminus of the heavy chain. However, the C-terminal lysine (Lys447) of the Fc region may or may not be present. Unless otherwise specified herein, numbering of amino acid residues in the CH2-CH3 domain region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "conjugate" is fusion protein of the present invention conjugated to one or more heterologous molecule(s), including but not limited to a label, neurological disorder drug or cytotoxic agent.

The term "linker" denotes a chemical linker or a single chain peptidic linker that covalently connects different entities of the blood-brain-barrier shuttle module and/or the fusion polypeptide and/or the conjugate as reported herein. The linker connects for example the brain effector entity to the monovalent binding entity. For example, if the monovalent binding entity comprises a CH2-CH3 Ig entity and a scFab directed to the blood-brain-barrier-receptor, then the linker conjugates the scFab to the C-terminal end of the CH3-CH2 Ig entity. The linker conjugating the brain effector entity to the monovalent binding entity (first linker) and the linker connecting the scFab to the C-terminal end of the CH2-CH3 Ig domain (second linker) can be the same or different.

Single chain peptidic linkers, comprising of from one to twenty amino acid residues joined by peptide bonds, can be used. In certain embodiments, the amino acids are selected from the twenty naturally-occurring amino acids. In certain other embodiments, one or more of the amino acids are selected from glycine, alanine, proline, asparagine, glutamine and lysine. In other embodiments, the linker is a chemical linker. In certain embodiments, the linker is a single chain peptidic linker with an amino acid sequence with a length of at least 25 amino acid residues, in one preferred embodiment with a length of 32 to 50 amino acid residues. In one embodiment the peptidic linker is a (GxS)n linker with G=glycine, S=serine, (x=3, n=8, 9 or 10) or (x=4 and n=6, 7 or 8), in one embodiment with x=4, n=6 or 7, in one preferred embodiment with x=4, n=7. In one embodiment the linker is (G4S)4 (SEQ ID NO: 95). In one embodiment the linker is (G4S)6G2 (SEQ ID NO: 96).

Conjugation may be performed using a variety of chemical linkers. For example, the monovalent binding entity or the fusion polypeptide and the brain effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker may be a "cleavable linker" facilitating release of the effector entity upon delivery to the brain. For example, an acid-labile linker, peptidase-sensitive linker, photolabile linker, dimethyl linker or disulfide-containing linker (Chan et al, Cancer Res. 52 (1992) 127-131; U.S. Pat. No. 5,208,020) may be used.

Covalent conjugation can either be direct or via a linker. In certain embodiments, direct conjugation is by construction of a polypeptide fusion (i.e. by genetic fusion of the two genes encoding the monovalent binding entity towards the BBBR and effector entity and expressed as a single polypeptide (chain)). In certain embodiments, direct conjugation is by formation of a covalent bond between a reactive group on one of the two portions of the monovalent binding entity against the BBBR and a corresponding group or acceptor on the brain effector entity. In certain embodiments, direct conjugation is by modification (i.e. genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e. an amino acid) with a desired reactive group (i.e. a cysteine residue) may be introduced into, e.g., the monovalent binding entity towards the BBBR antibody and a disulfide bond formed with the neurological drug. Methods for covalent conjugation of nucleic acids to proteins are also known in the art (i.e., photocrosslinking, see, e.g., Zatsepin et al. Russ. Chem. Rev. 74 (2005) 77-95). Conjugation may also be performed using a variety of linkers. For example, a monovalent binding entity and a effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptidic linkers, comprised of from one to twenty amino acid residues joined by peptide bonds, may also be used. In certain such embodiments, the amino acid residues are selected from the twenty naturally-occurring amino acids. In certain other such embodiments, one or more of the amino acid residues are selected from glycine, alanine, proline, asparagine, glutamine and lysine. The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used.

II. COMPOSITIONS AND METHODS

The equilibrium dissociation constants ($K_D$) are commonly used to describe molecular interactions. It is used as a measure of two molecules' interaction strength (e.g. affinity) with each other. Thus, the $K_D$ value is a measure for the strength of a bimolecular interaction.

But the $K_D$ value as such does not describe the kinetics of the molecular interaction, i.e. from the $K_D$ value it cannot be deduced on the one hand how quickly the two molecules bind to each other (association rate constant or "on rate") and on the other hand how quickly the molecules dissociate (dissociation rate constant or "off-rate"). Characterizing bimolecular interactions only by their $K_D$ value neglects the fact that an identical $K_D$ value can be made up by extremely different (differing orders of magnitude) on and off-rates as the $K_D$ value is the ratio thereof.

But the on- and off-rates are important for characterizing the binding behavior of molecules. The off-rate is especially important because it characterizes the binding duration of e.g. an antibody to its antigen. A long off-rate correlates to a slow dissociation of the formed complex whereas a short off-rate correlates to a quick dissociation.

In order to have a long-lasting (i.e. less frequent dosing requiring) or a tailor-made (e.g. depending on the surrounding conditions) interaction the off-rates have to be determined experimentally. This is even more important as it is next to impossible to predict the off-rate. Additionally the correlation between off-rate and binding affinity is poor as outlined above. For example, due to the fact that the $K_D$ value is the ratio of on- and off-rate even weak binders can stay bound long to their target whereas tight binders can dissociate rapidly.

A typical bottleneck in antibody generation projects is ranking of the many candidates obtained after panning on the basis of antibody binding strength. Ideally, such method will work without prior labeling of antigens and with crude bacterial lysates. Ylera, F., et al. (Anal. Biochem. 441 (2013) 208-213) reported a method for off-rate screening for selection of high-affinity anti-drug antibodies of crude *Escherichia coli* lysates containing monovalent Fab fragments. They have the off-rate chosen as the ranking parameter because amongst other things the off-rate is concentration-independent. They have chosen the monovalent format to avoid avidity effects during the off-rate ranking and affinity determination as they would be observed with full IgG. It has been found by Ylera et al. that the clone with the best koff-rate was identified by the koff ranking step, but would not have been identified using only ELISA signal strength as the selection criterion.

Murray, J. B., et al. (J. Med. Chem. 57 (2014) 2845-2850) reported Off-Rate Screening (ORS) By Surface Plasmon Resonance as An Efficient Method to Kinetically Sample Hit to Lead Chemical Space from Unpurified Reaction Products. It is outlined that the dissociation rate constant kd (off-rate) is the component of ligand-protein binding with the most significant potential to enhance compound potency. The authors do outline that measuring affinity kinetically throughout a drug discovery program is more informative than steady state affinity equilibrium determination. For example, a compound with a 10-fold slower on- and off-rate would not be recognized as different if evaluated by equilibrium measures of affinity. Furthermore the authors have found that the data determined with the BIAcore T200 instrument shows an average difference in the kds between crude and pure samples of 19%, similarly, the data determined with the older BIAcore T100 instrument had a 15% difference. The authors observe that the ids vary by an average of only 30% when compared across instruments and across time. This demonstrates that carryover contamination, long-term storage, and differing equipment have a modest effect on the observed kds. Indeed, these small deviations in the kds closely reflect the differences observed in multilaboratory studies where variability observed has been reported to be from 14% to 40% depending on the system (Murray, J. B., et al., J. Med. Chem. 57 (2014) 2845-2850; Katsamba, P. S., et al., Anal. Biochem. 352 (2006) 208-221).

In WO 2014/189973 anti-transferrin receptor antibodies and methods of use are reported. It is further reported that targeting a BBB receptor with a traditional specific high-affinity antibody generally resulted in limited increase in BBB transport. It was later found that the magnitude of antibody uptake into and distribution in the CNS is inversely related to its binding affinity for the BBB receptor amongst the anti-BBB antibodies studied. For example, a low-affinity antibody to transferrin receptor (TfR) dosed at therapeutic dose levels greatly improves BBB transport and CNS retention of the anti-TfR antibody relative to a higher-affinity anti-TfR antibody, and makes it possible to more readily attain therapeutic concentrations in the CNS (Atwal et al., Sci. Transl. Med. 3 (2011) 84ra43). Proof of such BBB transport was achieved using a bispecific antibody that binds both TfR and the amyloid precursor protein (APP) cleavage enzyme, β-secretase (BACE1). A single systemic dose of the bispecific anti-TfR/BACE1 antibody engineered using a low-affinity antibody not only resulted in significant antibody uptake in brain, but also dramatically reduced levels of brain Aβ1-40 compared to monospecific anti-BACE1 alone, suggesting that BBB penetrance affects the potency of anti-BACE1 (Atwal et al., Sci. Transl. Med. 3 (2011) 84ra43; Yu et al., Sci. Transl. Med. 3 (2011) 84ra44).

The data and experiments available highlight several causative mechanisms behind increasing uptake of an antibody into the CNS using a lower-affinity antibody approach.

First, high affinity anti-BBB-receptor (BBB-R) antibodies (e.g., anti-TfR antibody from Atwal et al. and Yu et al., supra) limit brain uptake by quickly saturating the BBB-R in the brain vasculature, thus reducing the total amount of antibody taken up into the brain and also restricting its distribution to the vasculature. Strikingly, lowering affinity for the BBB-R improves brain uptake and distribution, with a robust shift observed in localization from the vasculature to neurons and associated neuropil distributed within the CNS. It has been found that the affinity has to be below a certain upper level and above a certain lower level.

Second, the lower affinity of the antibody for the BBB-R is proposed to impair the ability of the antibody to return to the vascular side of the BBB via the BBB-R from the CNS side of the membrane because the overall affinity of the antibody for the BBB-R is low and the local concentration of the antibody on the CNS side of the BBB is non-saturating due to the rapid dispersal of the antibody into the CNS compartment.

Third, in vivo, and as observed for the TfR system, antibodies with less affinity for the BBB-R are not cleared from the system as efficiently as those with greater affinity for the BBB-R, and thus remain at higher circulating concentrations than their higher-affinity counterparts. This is advantageous because the circulating antibody levels of the lower-affinity antibody are sustained at therapeutic levels for a longer period of time than the higher-affinity antibody, which consequently improves uptake of antibody in brain for a longer period of time. Furthermore, this improvement in both plasma and brain exposure may reduce the frequency of dosing in the clinic, which would have potential benefit not only for patient compliance and convenience but also in lessening any potential side effects or off-target effects of the antibody and/or of a therapeutic compound coupled thereto.

These prior studies utilized mouse antibodies which bound specifically to mouse TfR, but which did not specifically recognize primate or human TfR. Accordingly, herein are provided antibodies and functional parts thereof which do specifically recognize both primate, especially cynomolgus, and human TfR, in order to facilitate safety and efficacy studies in primates with the antibodies prior to therapeutic or diagnostic use in humans.

A thorough nonclinical safety evaluation of monoclonal antibodies (mAbs) intended for therapeutic application is very important due to the increasing complexity of antibody engineering aspects and the variability induced by the diversity of recombinant production cell systems for generation of antibodies. Furthermore, their complex structure, unique biologic functions and the longer half-lives of mAbs compared with traditional small molecule drugs add to the safety considerations in addition to concerns due to prolonged clinical use of mAbs for the treatment of chronic diseases (Lynch, C. M., et al., mAbs 1 (2009) 2-11; Kim, S. J., et al., Mol. Cells 20 (2005) 17-29).

The overall goal of the nonclinical studies for mAbs is to define the toxicological properties of the mAb in question and provide information for product development. The main objectives of the nonclinical evaluation are (1) identification of target organs for toxicity and to determine whether the toxicity is reversible following the treatment, (2) identification of a safe starting dose for human Phase I clinical trials and subsequent dose escalation schemes, (3) provide information to monitor safety parameters in the clinical trials and (4) provide safety data to support claims on the product label. In order to achieve these goals, both in vitro and in vivo nonclinical studies aimed at defining and understanding the pharmacological properties of the antibody are conducted (Lynch, C. M., et al., mAbs 1 (2009) 2-11; Cavagnaro, J. A., In: Cavagnaro, J. A. (Ed.) "Preclinical safety evaluation of biopharmaceuticals"; Hoboken, N.J.: Wiley 2008; 45-65).

For successful nonclinical safety evaluation of a mAb, the most relevant animal species should be chosen for toxicity testing (Lynch, C. M., et al., mAbs 1 (2009) 2-11; Chapman, K., et al., Nat. Rev. Drug Discov. 6 (2007) 120-126). A relevant species is one in which the antibody is pharmacologically active, the target antigen should be present or expressed and tissue cross-reactivity profile should be similar to humans (Lynch, C. M., et al., mAbs 1 (2009) 2-11; Chapman, K., et al., Nat. Rev. Drug Discov. 6 (2007) 120-126; Subramanyam, M. and Mertsching, E., In: Cavagnaro J. A. (Ed.); Preclinical safety evaluation of biopharmaceuticals. Hoboken, N.J.: Wiley 2008; 181-205; Hall, W. C., et al., In: Cavagnaro, J. A. (Ed.); Preclinical safety evaluation of biopharmaceuticals. Hoboken, N.J.: Wiley 2008; 207-240). Using immunochemical or functional assays, a relevant animal species that expresses the desired epitope and demonstrates a tissue cross-reactivity profile similar to human tissues can be identified (Lynch, C. M., et al., mAbs 1 (2009) 2-11; Hall, W. C., et al., In: Cavagnaro, J. A. (Ed.); Preclinical safety evaluation of biopharmaceuticals. Hoboken, N.J.: Wiley 2008; 207-240). Species cross-reactivity studies, which are useful in this process, involve an immunohistochemical survey of tissues from a variety of species using commercially available multi-species tissue microarrays (Lynch, C. M., et al., mAbs 1 (2009) 2-11; Hall, W. C., et al., In: Cavagnaro, J. A. (Ed.); Preclinical safety evaluation of biopharmaceuticals. Hoboken, N.J.: Wiley 2008; 207-240). Alternatively, evaluation of antibody binding to cells from these animals by flow-activated cell sorting (FACS) is typically more sensitive than immunohistochemical analysis of tissue sections (Lynch, C. M., et al., mAbs 1 (2009) 2-11; Subramanyam, M. and Mertsching, E., In: Cavagnaro J. A. (Ed.); Preclinical safety evaluation of biopharmaceuticals. Hoboken, N.J.: Wiley 2008; 181-205). DNA and amino acid sequences of the target antigen should be compared across species; the homology between species should be determined (Lynch, C. M., et al., mAbs 1 (2009) 2-11; Subramanyam, M. and Mertsching, E., In: Cavagnaro J. A. (Ed.); Preclinical safety evaluation of biopharmaceuticals. Hoboken, N.J.: Wiley 2008; 181-205).

In addition, the biodistribution, function and structure of the antigen should be comparable between the relevant animal species and humans to allow evaluation of toxicity arising from antibody binding of the target antigen, which is referred to as on-target toxicity (Lynch, C. M., et al., mAbs 1 (2009) 2-11; 19,20). Furthermore, strong similarities in target antigen tissue distribution in the animal species and humans make it more likely that target organs of toxicity identified in animals will predict potential toxicities in humans. A lack of similarity in antigen tissue distribution between the animal species and humans does not entirely preclude use of the animal species for toxicity studies, but these differences must be taken into consideration for human risk assessment. As for antigen density or affinity, absolute equivalence between the animal model and humans is similarly not required. Justification for the relevancy of the species selected for toxicity testing should be included in the regulatory submission. If only one species is used for safety evaluation, a summary of experiments that demonstrate the absence of additional relevant species is warranted (Lynch, C. M., et al., mAbs 1 (2009) 2-11).

If the monoclonal antibody intended for a therapeutic use does not have a species cross-reactivity either a surrogate antibody has to be used or a different species for the model. Thus, surrogate antibodies are a potential solution to the limited safety testing possible with humanized monoclonal antibodies with restricted species cross-reactivity. However, there are currently no defined criteria by which a potential surrogate antibody should be judged prior to its use in determining safety issues for the clinical agent (Regulatory Toxicology and Pharmacology Volume 40, Issue 3, December 2004, Pages 219-226).

Thus, to identify an animal model for a particular mAb the above considerations have to be made. But nevertheless it is necessary that the mAb in question has a cross-reactivity with the target antigen of the test species. Otherwise even the most suitable test species cannot be used. Therefore, there is the need for mAbs that have no intra-species cross reactivity but an inter-species cross reactivity for its target in human and the species intended for non-clinical trials.

A. Exemplary Anti-Transferrin Antibodies

Herein are reported anti-transferrin receptor antibodies that have an off-rate for binding to the human transferrin receptor that is within a certain range in order to ensure proper BBB shuttling. It has been found that this range is defined at the one end by the off-rate of the murine anti-transferrin receptor antibody 128.1 (variable domain amino acid sequences given in SEQ ID NO: 64 and 65) determined by surface plasmon resonance for the cynomolgus transferrin receptor and at the other end by 5% of that off-rate (i.e. a 20-times slower dissociation). In one embodiment the off-rate for the human transferrin receptor is between and including 0.1 l/s and 0.005 l/s.

The humanized antibodies of clone 299 as reported herein were not available by applying standard humanization techniques. It was required to introduce non-standard mutations in the amino acid sequence in order to obtain a humanized antibody with transferrin receptor binding off-rates within the intended range of and including 0.1 l/s and 0.005 l/s. This is especially important as the antibodies as reported herein are being developed for crossing the human blood-brain-barrier to shuttle a therapeutic payload into the brain.

It has been found that in order to obtain a suitable and developable humanized antibody two cysteine amino acid residues in the light chain of the parental rabbit antibody had to be replaced by a proline and an asparagine amino acid residue, respectively. In addition to be within the given off-rate range a serine residue present in the middle of the rabbit CDRL3 had to be replaced by an alanine residue.

Is has further been found that it is advantageous to change three amino acid residues in the heavy chain at positions 65, 100g and 105 (numbering according to Kabat).

All numbering as used herein is based on the Kabat variable domain numbering scheme.

Rabbit anti-transferrin antibody clone 299 showed properties comparable to that of the anti-transferrin receptor antibody 128.1. This can be seen from the following Table.

| origin | transcytosis loading [pg] | transcytosis % basolateral | total basolateral [pg] | total apical [pg] | sum transported [pg] |
|---|---|---|---|---|---|
| mAb 128.1 | 2226 | 34 | 757 | 1229 | 1986 |
| clone-299 | 2773 | 36 | 998 | 1346 | 2344 |

| origin | loading % of mAb 128.1 | total basolateral % of mAb 128.1 | total apical % of mAb 128.1 | sum transported % of mAb 128.1 | EC50 [ng/mL] FACS hTfR-CHO |
|---|---|---|---|---|---|
| mAb 128.1 | 100 | 100 | 100 | 100 | 96 |
| clone-299 | 125 | 132 | 110 | 118 | 275 |

| origin | max. geo. mean hTfR-CHO | EC50 [ng/mL] FACS cyTfR | max. geo. mean Cyno TfR-CHO | ratio EC50 Cyno/human | ratio max Cyno/human |
|---|---|---|---|---|---|
| mAb 128.1 | 78200 | 314 | 52100 | 3.3 | 0.6 |
| clone-299 | 55600 | 241 | 52000 | 0.9 | 1.0 |

| origin | BIAcore off-rate huTfR [1/s] | BIAcore t½ huTfR [min] | BIAcore off-rate cyTfR [1/s] | BIAcore t½ Cyno TfR [min] | ratio t½ human/Cyno |
|---|---|---|---|---|---|
| mAb 128.1 | 6.06E−04 | 19 | 5.47E−02 | 0.2 | 90.2 |
| clone-299 | 6.16E−04 | 19 | 2.77E−04 | 42 | 0.4 |

In the following Table the off-rates of humanization variants of the rabbit light chain variable domain of clone 299 in combination with humanization variants of the rabbit heavy chain variable domain of clone 299 are shown. Binding partner was human transferrin receptor (determined at 25° C.).

| | VH | | | | | | | | | |
|---|---|---|---|---|---|---|---|---|---|---|
| VL | 0 (rb) | 1 | 2 | 5 | 6 | 7 | 8 | 9 | 11 | 12 |
| 0 (rb) | 4.34E−04 | 9.08E−04 | 8.06E−04 | 7.72E−04 | 6.63E−04 | 5.15E−04 | 4.06E−04 | 9.01E−04 | 9.05E−04 | 9.21E−04 |
| 1 | 5.69E−03 | 1.00E−03 | 1.00E−03 | 1.00E−03 | 1.00E−03 | 7.52E−03 | 3.19E−03 | 6.94E−03 | 1.00E−03 | 1.00E−03 |
| 2 | 1.25E−03 | 2.86E−03 | 2.75E−03 | 2.41E−03 | 1.87E−03 | 1.31E−03 | 1.01E−03 | 3.99E−03 | 3.85E−03 | 6.35E−03 |

-continued

| | | | | | VH | | | | | |
|---|---|---|---|---|---|---|---|---|---|---|
| 3 | 1.32E−03 | 4.31E−03 | 3.84E−03 | 3.16E−03 | 2.82E−03 | 1.45E−03 | 1.00E−03 | 4.17E−03 | 5.65E−03 | 5.86E−03 |
| 4 | 1.36E−03 | 2.56E−03 | 2.63E−03 | 2.38E−03 | 1.87E−03 | 1.25E−03 | 7.88E−04 | 2.70E−03 | 3.88E−03 | 3.11E−03 |
| 5 | 1.94E−03 | 2.71E−03 | 2.62E−03 | 2.53E−03 | 1.66E−03 | 1.35E−03 | 1.07E−03 | 3.50E−03 | 4.56E−03 | 5.82E−03 |
| 6 | 1.90E−03 | 5.38E−03 | 5.55E−03 | 4.64E−03 | 3.06E−03 | 1.97E−03 | 1.40E−03 | 6.83E−03 | 6.71E−03 | 7.05E−03 |
| 7 | 4.63E−03 | 7.33E−03 | 7.50E−03 | 6.97E−03 | 5.63E−03 | 3.66E−03 | 2.31E−03 | 7.61E−03 | 7.81E−03 | 7.71E−03 |
| 8 | 1.39E−03 | 4.85E−03 | 3.94E−03 | 3.78E−03 | 3.01E−03 | 1.72E−03 | 1.16E−03 | 5.23E−03 | 5.52E−03 | 5.31E−03 |
| 9-NYA | 1.41E−03 | 2.46E−03 | 2.21E−03 | 2.03E−03 | 1.41E−03 | 1.21E−03 | 1.01E−03 | 2.52E−03 | 2.42E−03 | 2.19E−03 |
| 10 | 1.88E−03 | 6.77E−03 | 6.49E−03 | 6.53E−03 | 4.55E−03 | 2.64E−03 | 1.73E−03 | 7.19E−03 | 7.16E−03 | 7.79E−03 |
| 12 | 5.41E−03 | 7.05E−03 | 8.14E−03 | 1.00E−03 | 7.78E−03 | 7.75E−03 | 6.72E−03 | 1.00E−03 | 7.87E−03 | 1.00E−03 |
| 14 | 1.78E−03 | 2.99E−03 | 2.44E−03 | 2.33E−03 | 2.20E−03 | 1.53E−03 | 1.04E−03 | 3.32E−03 | 3.51E−03 | 5.46E−03 |
| 15 | 6.63E−03 | 6.69E−03 | 6.38E−03 | 6.37E−03 | 4.21E−03 | 2.73E−03 | 1.81E−03 | 7.39E−03 | 7.09E−03 | 7.76E−03 |
| 17 | 1.49E−03 | 7.56E−03 | 7.12E−03 | 7.45E−03 | 7.17E−03 | 1.87E−03 | 1.12E−03 | 4.25E−03 | 7.55E−03 | 7.27E−03 |

| | VH | | | | | | | | | |
|---|---|---|---|---|---|---|---|---|---|---|
| VL | 13 | 15 | 16 | 17 | 18 | 19 | 20 | 21 | 22 | 23-DANG |
| 0 (rb) | 4.82E−04 | 7.63E−04 | 6.53E−04 | 4.13E−04 | 1.09E−03 | 1.00E−03 | 1.11E−03 | 5.65E−04 | 5.06E−04 | 3.38E−04 |
| 1 | 1.00E−03 | 7.72E−03 | 7.71E−03 | 4.33E−03 | 1.00E−03 | 1.00E−03 | 1.00E−03 | 7.71E−03 | 5.78E−03 | 2.80E−03 |
| 2 | 2.46E−03 | 2.16E−03 | 1.97E−03 | 1.05E−03 | 4.89E−03 | 7.69E−03 | 5.25E−03 | 1.38E−03 | 1.26E−03 | 7.15E−04 |
| 3 | 2.77E−03 | 2.07E−03 | 1.73E−03 | 8.43E−04 | 6.65E−03 | 1.00E−03 | 7.15E−03 | 1.94E−03 | 1.43E−03 | 7.83E−04 |
| 4 | 1.30E−03 | 1.34E−03 | 1.27E−03 | 7.23E−04 | 3.35E−03 | 1.00E−03 | 4.36E−03 | 1.46E−03 | 1.18E−03 | 7.61E−04 |
| 5 | 2.18E−03 | 2.14E−03 | 2.23E−03 | 1.23E−03 | 3.49E−03 | 1.00E−03 | 3.52E−03 | 1.37E−03 | 1.41E−03 | 8.80E−04 |
| 6 | 3.65E−03 | 3.50E−03 | 3.39E−03 | 1.71E−03 | 6.74E−03 | 1.00E−03 | 6.06E−03 | 2.07E−03 | 2.14E−03 | 1.16E−03 |
| 7 | 6.68E−03 | 5.43E−03 | 5.25E−03 | 2.33E−03 | 7.66E−03 | 1.00E−03 | 7.14E−03 | 2.38E−03 | 3.37E−03 | 1.55E−03 |
| 8 | 2.47E−03 | 2.09E−03 | 1.97E−03 | 1.11E−03 | 6.77E−03 | 6.71E−03 | 6.58E−03 | 1.74E−03 | 1.65E−03 | 9.41E−04 |
| 9-NYA | 1.39E−03 | 1.42E−03 | 1.36E−03 | 9.34E−04 | 2.21E−03 | 6.17E−03 | 1.89E−03 | 1.13E−03 | 1.26E−03 | 7.69E−04 |
| 10 | 5.89E−03 | 3.99E−03 | 4.24E−03 | 1.88E−03 | 7.46E−03 | 1.00E−03 | 7.05E−03 | 2.11E−03 | 2.09E−03 | 1.20E−03 |
| 12 | 7.85E−03 | 7.64E−03 | 7.54E−03 | 2.84E−03 | 1.00E−03 | 1.00E−03 | 1.00E−03 | 7.54E−03 | 6.44E−03 | 1.87E−03 |
| 14 | 2.22E−03 | 1.94E−03 | 1.75E−03 | 1.05E−03 | 3.00E−03 | 7.96E−03 | 2.39E−03 | 1.03E−03 | 1.12E−03 | 7.33E−04 |
| 15 | 7.11E−03 | 6.03E−03 | 4.77E−03 | 1.56E−03 | 7.58E−03 | 1.00E−03 | 7.85E−03 | 1.92E−03 | 1.79E−03 | 9.86E−04 |
| 17 | 3.39E−03 | 1.69E−03 | 1.66E−03 | 9.88E−04 | 5.30E−03 | 1.00E−03 | 4.57E−03 | 9.97E−04 | 9.38E−04 | 6.94E−04 |

The combination of VH23 with VL9 was chosen as starting point for further engineering to develop a binding site that is reflecting the binding properties of the antibody 128.1 to the cynomolgus transferrin receptor with respect to the binding to human transferrin receptor more closely.

In the following Table the off-rates of different exemplary variants of VH23 and VL9 as well as different other variable domain humanization variants for the human transferrin receptor are shown in comparison (determined according to Example 14, 25° C.).

In the following Table the kinetic data of different exemplary variants of VH23 and VL9 are shown in comparison (determine according to Example 13).

| BIAcore Assay @ 25° C. | TfR | kd [s$^{-1}$] | ka [s$^{-1}$M$^{-1}$] | kD [M] |
|---|---|---|---|---|
| mAb 128.1 | cynomolgus | 7.33E−02 | 5.41E+05 | 1.36E−07 |
| VH23-DASG/VL09-NYA | human | 3.95E−02 | 8.83E+04 | 4.47E−07 |
| VH23-DAQG/VL09-NYA | human | 1.37E−02 | 1.21E+05 | 1.13E−07 |
| VH23-DANG/VL09-NYA | human | 8.83E−03 | 1.55E+05 | 5.72E−08 |

In the following Table the off-rates of humanization variants of the murine light chain variable domain of clone 494 in combination with humanization variants of the murine heavy chain variable domain of clone 494 are shown. Binding partner was human transferrin receptor.

| | VK9-NYA | VK9-SYA | VK9-GYS | VK9-CYS | VH567-P...NYA | VK12-HYS | VK17-TYS | VK15-AYS | VK2-SYS | VK6-SYS |
|---|---|---|---|---|---|---|---|---|---|---|
| VH23-DANG | 8.83E−03 | | 3.96E−03 | | 4.62E−03 | 1.53E−02 | 2.29E−03 | 6.97E−03 | 5.22E−03 | 1.32E−02 |
| VH23-DASG | 3.95E−02 | 4.84E−04 | 3.73E−03 | 2.33E−03 | | | | | | |
| VH23-DAQG | 1.49E−02 | 7.55E−04 | 3.75E−03 | 1.51E−03 | | | | | | |
| VH9-DANG | 1.82E−03 | | | 6.52E−03 | | | | | 4.02E−02 | |
| VH9-DAQG | 1.25E−03 | | | | | | | | | |
| VH7-DANG | | | | | | | | | | 3.08E−02 | reference: 128.1 = 7.78E−02 (determined for the cynomolgus transferrin receptor).

| | VH | | | | |
|---|---|---|---|---|---|
| VL | 0 (mu) | 1 | 2 | 3 | 4 |
| 0 (mu) | 1.36E−04 | 1.37E−04 | 1.56E−04 | 1.48E−04 | 1.77E−04 |
| 1 | 3.70E−04 | 4.10E−04 | 4.54E−04 | 4.76E−04 | 4.48E−04 |
| 2 | 3.64E−04 | 3.99E−04 | 4.26E−04 | 4.15E−04 | 4.38E−04 |
| 3 | 3.39E−04 | 3.86E−04 | 4.30E−04 | 4.34E−04 | 4.52E−04 |

-continued

| | VH | | | | |
|---|---|---|---|---|---|
| VL | 0 (mu) | 1 | 2 | 3 | 4 |
| 4 | 5.42E-04 | 6.57E-04 | 7.03E-04 | 6.83E-04 | 7.05E-04 |
| 5 | 5.44E-04 | 6.84E-04 | 7.17E-04 | 7.17E-04 | 7.28E-04 |
| 6 | 3.81E-04 | 4.86E-04 | 5.27E-04 | 5.50E-04 | 5.52E-04 |
| 7 | 2.32E-04 | 2.74E-04 | 2.99E-04 | 3.06E-04 | 3.26E-04 |

In more detail, in one aspect, the invention is based, in part, on the finding that the anti-transferrin receptor antibody as reported herein can be used as blood-brain-barrier shuttle module to deliver a brain effector entity across the blood-brain-barrier into the brain. In certain embodiments, the blood-brain-barrier shuttle module is a monovalent binding entity that specifically binds to the transferrin receptor. The anti-transferrin receptor antibodies as reported herein when used as blood-brain-barrier shuttle module are useful, e.g., for the diagnosis or treatment of neurological disorders, such as Alzheimer's disease, Parkinson's Disease and Alzheimer's Disease with Parkinson's Disease co-morbidity.

It has been found that an antibody comprising the heavy chain variable domain of SEQ ID NO: 24 and the light chain variable domain of SEQ ID NO: 37 reflects with respect to the human transferrin receptor the binding properties of the murine antibody 128.1 with respect to the cynomolgus transferrin receptor regarding the binding off-rate.

Accordingly, one aspect as reported herein is an isolated antibody that binds to human transferrin receptor (huTfR) and cynomolgus transferrin receptor (cyTfR), wherein the antibody has an off-rate determined by surface plasmon resonance for the human transferrin receptor between 0.1 l/s and 0.005 l/s.

Another aspect as reported herein is the use of an antibody or antibody fragment that binds to human transferrin receptor (huTfR) and cynomolgus transferrin receptor (cyTfR), wherein the antibody has an off-rate determined by surface plasmon resonance for the human transferrin receptor between 0.1 l/s and 0.005 l/s, for the delivery of a therapeutic entity across the blood-brain-barrier.

In one embodiment the off-rate is determined at 500, 250, 125, 62.5, 31.25, 15.625 and 0 nM.

In one embodiment the off-rate is determined using a surface plasmon resonance chip with a biotin surface and a running buffer of 1×PBS supplemented with 250 mM sodium chloride at a flow rate of 10 µL/min.

In one embodiment the association is monitored for 180 seconds and the dissociation is monitored for 600 seconds.

In one embodiment the off-rate is determined on a BIAcore T200.

In one embodiment the off-rate is between 0.08 l/s and 0.008 l/s.

In one embodiment of all aspects the off-rate is determined at 25° C.

In one embodiment of all aspects the off-rate is the off-rate determined at 25° C.

One aspect as reported herein is an anti-transferrin receptor antibody that specifically binds to human transferrin receptor (huTfR) and cynomolgus transferrin receptor (cyTfR), which comprises i) a humanized heavy chain variable domain derived from the heavy chain variable domain of SEQ ID NO: 01 and ii) a humanized light chain variable domain derived from the light chain variable domain of SEQ ID NO: 26, wherein the light chain variable domain has at position 80 a proline amino acid residue (P), at position 91 an asparagine amino acid residue (N) and at position 93 an alanine amino acid residue (A) (numbering according to Kabat).

In one embodiment the antibody further has in the heavy chain variable domain at position 100g a serine amino acid residue (S) (numbering according to Kabat).

In one embodiment the antibody further has in the heavy chain variable domain at position 65 a serine amino acid residue (S) (numbering according to Kabat).

In one embodiment the antibody further has in the heavy chain variable domain at position 105 a glutamine amino acid residue (Q) (numbering according to Kabat).

One aspect as reported herein is an anti-transferrin receptor antibody that specifically binds to human transferrin receptor (huTfR) and cynomolgus transferrin receptor (cyTfR), which comprises i) a humanized heavy chain variable domain derived from the heavy chain variable domain of SEQ ID NO: 01 and ii) a humanized light chain variable domain derived from the light chain variable domain of SEQ ID NO: 26, wherein the antibody has an off-rate in the unit l/s for the human transferrin receptor that is equal to or less than (i.e. at most) the off-rate in the unit l/s of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 64 and a light chain variable domain of SEQ ID NO: 65.

In one embodiment the antibody has an off-rate in the unit l/s for the human transferrin receptor that is i) equal to or less than (i.e. at most) the off-rate in the unit l/s of the anti-transferrin receptor antibody 128.1 for the cynomolgus transferrin receptor and ii) equal to or more than (i.e. at least) 5% of the off-rate in the unit l/s of the anti-transferrin receptor antibody 128.1 for the cynomolgus transferrin receptor.

One aspect as reported herein is an anti-transferrin receptor antibody that specifically binds to human transferrin receptor (huTfR) and cynomolgus transferrin receptor (cyTfR). In certain embodiments, an anti-transferrin receptor antibody
  binds to human transferrin receptor (huTfR) and cynomolgus transferrin receptor (cyTfR);
  has an off-rate in the unit l/s for the human transferrin receptor that is equal to or less than (i.e. at most) that of the anti-transferrin receptor antibody 128.1 for the cynomolgus transferrin receptor, whereby the off-rates are determined by surface plasmon resonance, and whereby the anti-transferrin receptor antibody 128.1 has a heavy chain variable domain of SEQ ID NO: 64 and a light chain variable domain of SEQ ID NO: 65;
  binds with an off-rate for the human transferrin receptor that is between and including 0.1 l/s and 0.005 l/s.

In one aspect, herein is provided an anti-transferrin receptor antibody comprising at least one, two, three, four, five, or six HVRs selected from (a) a HVR-H1 comprising the amino acid sequence of SEQ ID NO: 66; (b) a HVR-H2 comprising the amino acid sequence of SEQ ID NO: 68; (c) a HVR-H3 comprising the amino acid sequence of SEQ ID NO: 71, 72 or 73; (d) a HVR-L1 comprising the amino acid sequence of SEQ ID NO: 75; (e) a HVR-L2 comprising the amino acid sequence of SEQ ID NO: 76; and (f) a HVR-L3 comprising the amino acid sequence of SEQ ID NO: 78.

In one aspect, the invention provides an antibody comprising at least one, at least two, or all three VH HVR sequences selected from (a) a HVR-H1 comprising the amino acid sequence of SEQ ID NO: 66; (b) a HVR-H2 comprising the amino acid sequence of SEQ ID NO: 68; and (c) a HVR-H3 comprising the amino acid sequence of SEQ ID NO: 71 or 72 or 73. In one aspect, the invention provides an antibody comprising at least one, at least two, or all three VH HVR sequences selected from (a) a HVR-H1 comprising the amino acid sequence of SEQ ID NO: 66; (b) aHVR-H2 comprising the amino acid sequence of SEQ ID NO: 68; and (c) a HVR-H3 comprising the amino acid sequence of SEQ ID NO: 72. In one aspect, the invention provides an antibody comprising at least one, at least two, or all three VH HVR sequences selected from (a) a HVR-H1 comprising the amino acid sequence of SEQ ID NO: 66; (b) a HVR-H2 comprising the amino acid sequence of SEQ ID NO: 68; and (c) a HVR-H3 comprising the amino acid sequence of SEQ ID NO: 73. In one embodiment, the antibody comprises HVR-H3 comprising the amino acid sequence of SEQ ID NO: 71 or 72 or 73. In another embodiment, the antibody comprises HVR-H3 comprising the amino acid sequence of SEQ ID NO: 71 or 72 or 73 and HVR-L3 comprising the amino acid sequence of SEQ ID NO: 78. In a further embodiment, the antibody comprises HVR-H3 comprising the amino acid sequence of SEQ ID NO: 71 or 72 or 73, HVR-L3 comprising the amino acid sequence of SEQ ID NO: 78, and HVR-H2 comprising the amino acid sequence of SEQ ID NO: 68. In a further embodiment, the antibody comprises (a) a HVR-H1 comprising the amino acid sequence of SEQ ID NO: 66; (b) a HVR-H2 comprising the amino acid sequence of SEQ ID NO: 68; and (c) a HVR-H3 comprising the amino acid sequence of SEQ ID NO: 72.

In another aspect, the invention provides an antibody comprising at least one, at least two, or all three VL HVR sequences selected from (a) a HVR-L1 comprising the amino acid sequence of SEQ ID NO: 75; (b) a HVR-L2 comprising the amino acid sequence of SEQ ID NO: 76; and (c) a HVR-L3 comprising the amino acid sequence of SEQ ID NO: 78. In one embodiment, the antibody comprises (a) a HVR-L1 comprising the amino acid sequence of SEQ ID NO: 75; (b) a HVR-L2 comprising the amino acid sequence of SEQ ID NO: 76; and (c) a HVR-L3 comprising the amino acid sequence of SEQ ID NO: 78.

In another aspect, an antibody of the invention comprises (a) a VH domain comprising at least one, at least two, or all three VH HVR sequences selected from (i) a HVR-H1 comprising the amino acid sequence of SEQ ID NO: 66, (ii) a HVR-H2 comprising the amino acid sequence of SEQ ID NO: 68, and (iii) HVR-H3 comprising an amino acid sequence selected from SEQ ID NO: 71 or 72 or 73; and (b) a VL domain comprising at least one, at least two, or all three VL HVR sequences selected from (i) a HVR-L1 comprising the amino acid sequence of SEQ ID NO: 75, (ii) a HVR-L2 comprising the amino acid sequence of SEQ ID NO: 76, and (c) a HVR-L3 comprising the amino acid sequence of SEQ ID NO: 78.

In another aspect, the invention provides an antibody comprising (a) a HVR-H1 comprising the amino acid sequence of SEQ ID NO: 66; (b) a HVR-H2 comprising the amino acid sequence of SEQ ID NO: 68; (c) a HVR-H3 comprising the amino acid sequence of SEQ ID NO: 72; (d) a HVR-L1 comprising the amino acid sequence of SEQ ID NO: 75; (e) a HVR-L2 comprising the amino acid sequence of SEQ ID NO: 76; and (f) HVR-L3 comprising an amino acid sequence selected from SEQ ID NO: 78.

In any of the above embodiments, an anti-transferrin receptor antibody is humanized. In one embodiment, an anti-transferrin receptor antibody comprises HVRs as in any of the above embodiments, and further comprises an acceptor human framework, e.g. a human immunoglobulin framework or a human consensus framework.

In another aspect, an anti-transferrin receptor antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 24 and having about the same off-rate as an antibody comprises a heavy chain variable domain (VH) sequence of SEQ ID NO: 24. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-transferrin receptor antibody comprising that sequence retains the ability to bind to the transferrin receptor with the same off-rate. In certain embodiments, a total of 1 to 10 amino acids have been substituted, inserted and/or deleted in SEQ ID NO: 24. In certain embodiments, substitutions, insertions, or deletions occur in regions outside the HVRs (i.e., in the FRs). Optionally, the anti-transferrin receptor antibody comprises the VH sequence of SEQ ID NO: 24, including post-translational modifications of that sequence. In a particular embodiment, the VH comprises one, two or three HVRs selected from: (a) a HVR-H1 comprising the amino acid sequence of SEQ ID NO: 66, (b) a HVR-H2 comprising the amino acid sequence of SEQ ID NO: 68, and (c) a HVR-H3 comprising the amino acid sequence of SEQ ID NO: 72.

In another aspect, an anti-transferrin receptor antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 37 and having about the same off-rate as an antibody comprises a light chain variable domain (VL) sequence of SEQ ID NO: 37. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-transferrin receptor antibody comprising that sequence retains the ability to bind to the transferrin receptor with the same off-rate. In certain embodiments, a total of 1 to 10 amino acids have been substituted, inserted and/or deleted in SEQ ID NO: 37. In certain embodiments, the substitutions, insertions, or deletions occur in regions outside the HVRs (i.e., in the FRs). Optionally, the anti-transferrin receptor antibody comprises the VL sequence in SEQ ID NO: 37, including post-translational modifications of that sequence. In a particular embodiment, the VL comprises one, two or three HVRs selected from (a) a HVR-L1 comprising the amino acid sequence of SEQ ID NO: 75; (b) a HVR-L2 comprising the amino acid sequence of SEQ ID NO: 76; and (c) a HVR-L3 comprising the amino acid sequence of SEQ ID NO: 78.

In another aspect, an anti-transferrin receptor antibody is provided, wherein the antibody comprises a VH as in any of the embodiments provided above, and a VL as in any of the embodiments provided above. In one embodiment, the antibody comprises the VH and VL sequences in SEQ ID NO: 24 and SEQ ID NO: 37, respectively, including post-translational modifications of those sequences.

In a further aspect of the invention, an anti-transferrin receptor antibody according to any of the above embodiments is a monoclonal antibody, including a chimeric, humanized or human antibody. In one embodiment, an anti-transferrin receptor antibody is an antibody fragment, e.g., an Fv, Fab, Fab', scFv, diabody, or F(ab')$_2$ fragment. In another embodiment, the antibody is a full length antibody, e.g., an intact IgG1 antibody or other antibody class or isotype as defined herein.

In one embodiment of all aspects the antibody is coupled to a therapeutic compound.

In another embodiment of all aspects the antibody is coupled to an imaging agent or a label.

In another embodiment the antibody is a multispecific antibody and the therapeutic compound optionally forms one portion of the multispecific antibody. In one such embodiment, the multispecific antibody comprises a first antigen binding site which binds TfR and a second antigen binding site which binds a brain antigen. In one such aspect, the brain antigen is selected from the group consisting of: beta-secretase 1 (BACE1), Abeta, epidermal growth factor receptor (EGFR), human epidermal growth factor receptor 2 (HER2), tau, apolipoprotein E (ApoE), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), glucocerebrosidase, and caspase 6. In another embodiment, the multispecific antibody binds both TfR and BACE1. In another embodiment, the multispecific antibody binds both TfR and Abeta. In another embodiment, the multispecific antibody binds both TfR and alpha synuclein. In another embodiment, the multispecific antibody binds both TfR and CD20. In another embodiment, the multispecific antibody binds both TfR and glucocerebrosidase. In another embodiment, the therapeutic compound is a neurological disorder drug.

In one aspect of the above embodiment, the invention provides a pharmaceutical formulation comprising any of the foregoing antibodies and a pharmaceutically acceptable carrier.

In one aspect of the above embodiment, the invention provides any of the foregoing antibodies for use as a medicament.

In another aspect of the above embodiment, the invention provides the use of any of the foregoing antibodies in the manufacture of a medicament for treating a neurological disorder. In one embodiment, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation.

In another aspect of the above embodiment, the invention provides any of the foregoing antibodies for use in treating a neurological disorder. In one embodiment, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation.

In another aspect of the above embodiment, the invention provides any of the foregoing antibodies for use in transporting one or more compounds across the BBB.

In another aspect of the above embodiment, use of any of the foregoing antibodies in the manufacture of a medicament for transporting one or more compounds across the BBB is provided.

In one aspect of the above embodiment, a method of transporting a compound across the BBB in a subject is provided, comprising exposing any of the foregoing antibodies to the BBB such that the antibody transports the compound coupled thereto across the BBB. In one embodiment, the BBB is in a human subject. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In another aspect of the above embodiment, a method of increasing exposure of the CNS of a subject to a compound is provided, comprising exposing any of the foregoing antibodies to the BBB such that the antibody transports the compound coupled thereto across the BBB. In one embodiment, the BBB is in a human subject. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In one aspect of the above embodiment, a method of increasing retention in the CNS of a compound administered to a subject is provided, comprising exposing any of the foregoing antibodies to the BBB such that the retention in the CNS of the compound is increased. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In one aspect of the above embodiment, a method of treating a neurological disorder in a mammal is provided, comprising treating the mammal with any of the foregoing antibodies. In one embodiment, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation. In one embodiment, the neurological disorder is in a human subject. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In one embodiment, the antibody is modified in one or more properties selected from the effector function of the antibody Fc region, the complement activation function of the antibody, and the affinity of the antibody for TfR.

In one embodiment, the property is the effector function of the antibody Fc region.

In one embodiment, the property is the complement activation function of the antibody.

In one embodiment, the property is the affinity of the antibody for TfR.

In one embodiment, the effector function or complement activation function has been reduced or eliminated relative to a wild-type antibody of the same isotype. In one embodiment, the effector function is reduced or eliminated by a method selected from reduction of glycosylation of the antibody, modification of the antibody isotype to an isotype that naturally has reduced or eliminated effector function, and modification of the Fc region.

In one embodiment, the effector function is reduced or eliminated by reduction of glycosylation of the antibody. In one embodiment, the glycosylation of the antibody is reduced by a method selected from: production of the antibody in an environment that does not permit wild-type glycosylation; removal of carbohydrate groups already present on the antibody; and modification of the antibody such that wild-type glycosylation does not occur.

In one embodiment, the glycosylation of the antibody is reduced by a production of the antibody in an environment that does not permit wild-type glycosylation, such as production in a non-mammalian cell production system or where the antibody is produced synthetically. In one embodiment, the antibody is produced in a non-mammalian cell production system. In another embodiment, the antibody is produced synthetically.

In one embodiment, the glycosylation of the antibody is reduced by modification of the antibody such that wild-type glycosylation does not occur, such as wherein the Fc region of the antibody comprises a mutation at position 297 such that the wild-type asparagine residue at that position is replaced with another amino acid that interferes with glycosylation at that position.

In one embodiment, the effector function is reduced or eliminated by at least one modification of the Fc region. In one embodiment, the effector function or complement activation function is reduced or eliminated by deletion of all or a portion of the Fc region, or by engineering the antibody such that it does not include an Fc region or non-Fc region competent for effector function or complement activation function. In one embodiment, the at least one modification of the Fc region is selected from: a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 30 335, 338, 340, 373, 376, 382, 388, 389, 414, 416, 419, 434, 435, 437, 438, and 439; a point mutation of the Fc region to impair binding to C1q selected from the following positions: 270, 322, 329, and 321; eliminating some or all of the Fc region, and a point mutation at position 132 of the CH1 domain. In one embodiment, the modification is a point mutation of the Fc region to impair binding to C1q selected from the following positions: 270, 322, 329, and 321. In another embodiment, the modification is elimination of some or all of the Fc region. In another embodiment, complement-triggering function is reduced or eliminated by deletion of all or a portion of the Fc region, or by engineering the antibody such that it does not include an Fc region that engages the complement pathway. In one embodiment, the antibody is selected from a Fab or a single chain antibody. In another embodiment, the non-Fc region of the antibody is modified to reduce or eliminate activation of the complement pathway by the antibody. In one embodiment, the modification is a point mutation of the CH1 region to impair binding to C3. In one embodiment, the point mutation is at position 132 (see, e.g., Vidarte et al., J. Biol. Chem. 276 (2001) 38217-38223).

In one aspect of the above embodiment, the affinity of the antibody for TfR is decreased, as measured relative to a wild-type antibody of the same isotype not having lowered affinity for TfR. In one such aspect, the antibody has a $K_D$ or $IC_{50}$ for TfR of about 1 pM to about 100 μM.

In one embodiment the antibody as reported herein is effector function silent. In one embodiment the antibody has no effector function. In one embodiment the antibody is of the human IgG1 subclass and has the mutations L234A, L235A and P329G in both heavy chains (numbering according to the EU index of Kabat).

In one embodiment the antibody is
a) a full length antibody of the human subclass IgG1, or
b) a full length antibody of the human subclass IgG4, or
c) a full length antibody of the human subclass IgG1 with the mutations L234A, L235A and P329G,
d) a full length antibody of the human subclass IgG4 with the mutations S228P, L235E and optionally P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
f) a full length antibody of the human subclass IgG4 with the mutations S228P and optionally P329G in both heavy chains and the mutations T366W and S354C in one heavy chain and the mutations T366S, L368A, Y407V and Y349C in the respective other heavy chain.

In one aspect of the above embodiment, the invention provides a pharmaceutical formulation comprising any of the foregoing antibodies and a pharmaceutically acceptable carrier.

In one aspect of the above embodiment, the invention provides any of the foregoing antibodies for use as a medicament.

In another aspect of the above embodiment, the invention provides the use of any of the foregoing antibodies in the manufacture of a medicament for treating a neurological disorder. In one embodiment, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation.

In another aspect of the above embodiment, the invention provides any of the foregoing antibodies for use in treating a neurological disorder. In one embodiment, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation.

In another aspect of the above embodiment, the invention provides any of the foregoing antibodies for use in transporting one or more compounds across the BBB.

In another aspect of the above embodiment, use of any of the foregoing antibodies in the manufacture of a medicament for transporting one or more compounds across the BBB is provided.

In one aspect of the above embodiment, a method of transporting a compound across the BBB in a subject is provided, comprising exposing any of the foregoing antibodies to the BBB such that the antibody transports the compound coupled thereto across the BBB. In one embodiment, the BBB is in a human subject. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In another aspect of the above embodiment, a method of increasing exposure of the CNS of a subject to a compound is provided, comprising exposing any of the foregoing antibodies to the BBB such that the antibody transports the compound coupled thereto across the BBB. In one embodiment, the BBB is in a human subject.

In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In one aspect of the above embodiment, a method of increasing retention in the CNS of a compound administered to a subject is provided, comprising exposing any of the foregoing antibodies to the BBB such that the retention in the CNS of the compound is increased. In one embodiment, the BBB is in a human subject. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In one aspect of the above embodiment, a method of treating a neurological disorder in a mammal is provided, comprising treating the mammal with any of the foregoing antibodies. In one embodiment, the neurological disorder is selected from the group consisting of a neuropathy disorder, a neurodegenerative disease, cancer, an ocular disease disorder, a seizure disorder, a lysosomal storage disease, amyloidosis, a viral or microbial disease, ischemia, a behavioral disorder, and CNS inflammation. In another such aspect, the neurological disorder is in a human subject. In one embodiment, the antibody coupled to the compound is administered at a therapeutic dose. In one embodiment, the therapeutic dose is TfR-saturating. In another embodiment, administration of the antibody is at a dose and/or dose frequency calibrated to minimize acute clinical symptoms of the antibody administration.

In another embodiment, a method of decreasing clearance of a compound administered to a subject is provided, wherein the compound is coupled to an antibody which binds with low affinity to TfR, such that the clearance of the compound is decreased.

In another embodiment, a method of optimizing the pharmacokinetics and/or pharmacodynamics of a compound to be efficacious in the CNS in a subject is provided, wherein the compound is coupled to an antibody which binds with low affinity to TfR, and the antibody is selected such that its affinity for TfR after coupling to the compound results in an amount of transport of the antibody conjugated to the compound across the BBB that optimizes the pharmacokinetics and/or pharmacodynamics of the compound in the CNS.

In a further aspect, an anti-transferrin receptor antibody according to any of the above aspects and embodiments may incorporate any of the features, singly or in combination, as described in Sections 1-5 below:

1. Antibody Affinity

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 µg/mL of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µL/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CMS chips at ~10 response units (RU). In one embodiment, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/mL (~0.2 µM) before injection at a flow rate of 5 µL/minute to achieve approximately 10 response units (RU) of coupled protein. Following the injection of antigen, 1 M ethanolamine is injected to block non-reacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (KD) is calculated as the ratio $k_{off}/k_{on}$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for the transferrin receptor and the other is for any other antigen. Bispecific antibodies may also be used to localize cytotoxic agents to cells which express the transferrin receptor. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, Metal., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies", are also included herein (see, e.g. US 2006/0025576).

The antibody or fragment herein also includes a "Dual Acting Fab" or "DAF" comprising an antigen binding site that binds to the transferrin receptor as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

In one embodiment of all aspects as reported herein the anti-transferrin receptor antibody is a bispecific antibody.

One aspect as reported herein is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other,
  wherein the first antigen or the second antigen is the human transferrin receptor.

The antibody under a) does not contain a modification as reported under b) and the heavy chain and the light chain under a) are isolated chains.

In the antibody under b)
within the light chain
the variable light chain domain VL is replaced by the variable heavy chain domain VH of said antibody,
and
within the heavy chain
the variable heavy chain domain VH is replaced by the variable light chain domain VL of said antibody.

In one embodiment
i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid,
or
ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one preferred embodiment
i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
or
ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CH1 of the second light chain the amino acids at position 147 and 213 are substituted by E (numbering according to EU index of Kabat).

In one preferred embodiment in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

One aspect as reported herein is a bivalent, bispecific antibody comprising
a) a first light chain and a first heavy chain of an antibody specifically binding to a first antigen, and
b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other,
wherein the first antigen or the second antigen is the human transferrin receptor.

The antibody under a) does not contain a modification as reported under b) and the heavy chain and the light chain and a) are isolated chains.

In the antibody under b)
within the light chain
the variable light chain domain VL is replaced by the variable heavy chain domain VH of said antibody, and the constant light chain domain CL is replaced by the constant heavy chain domain CH1 of said antibody;
and
within the heavy chain
the variable heavy chain domain VH is replaced by the variable light chain domain VL of said antibody, and the constant heavy chain domain CH1 is replaced by the constant light chain domain CL of said antibody.

One aspect as reported herein is a bivalent, bispecific antibody comprising
a) a first light chain and a first heavy chain of an antibody specifically binding to a first antigen, and
b) a second light chain and a second heavy chain of an antibody specifically binding to a second antigen, wherein the constant domains CL and CH1 of the second light chain and the second heavy chain are replaced by each other,
wherein the first antigen or the second antigen is the human transferrin receptor.

The antibody under a) does not contain a modification as reported under b) and the heavy chain and the light chain under a) are isolated chains.

In the antibody under b)
within the light chain
the constant light chain domain CL is replaced by the constant heavy chain domain CH1 of said antibody;
and within the heavy chain
the constant heavy chain domain CH1 is replaced by the constant light chain domain CL of said antibody.

One aspect as reported herein is a multispecific antibody comprising
a) a full length antibody specifically binding to a first antigen and consisting of two antibody heavy chains and two antibody light chains, and b) one, two, three or four single chain Fab fragments specifically binding to one to four further antigens (i.e. a second and/or third and/or fourth and/or fifth antigen, preferably specifically binding to one further antigen, i.e. a second antigen), wherein said single chain Fab fragments under b) are fused to said full length antibody under a) via a peptidic linker at the C- or N-terminus of the heavy or light chain of said full length antibody, wherein the first antigen or one of the further antigens is the human transferrin receptor.

In one embodiment one or two identical single chain Fab fragments binding to a second antigen are fused to said full length antibody via a peptidic linker at the C-terminus of the heavy or light chains of said full length antibody.

In one embodiment one or two identical single chain Fab fragments binding to a second antigen are fused to said full length antibody via a peptidic linker at the C-terminus of the heavy chains of said full length antibody.

In one embodiment one or two identical single chain Fab fragments binding to a second antigen are fused to said full length antibody via a peptidic linker at the C-terminus of the light chains of said full length antibody.

In one embodiment two identical single chain Fab fragments binding to a second antigen are fused to said full length antibody via a peptidic linker at the C-terminus of each heavy or light chain of said full length antibody.

In one embodiment two identical single chain Fab fragments binding to a second antigen are fused to said full length antibody via a peptidic linker at the C-terminus of each heavy chain of said full length antibody.

In one embodiment two identical single chain Fab fragments binding to a second antigen are fused to said full length antibody via a peptidic linker at the C-terminus of each light chain of said full length antibody.

One aspect as reported herein is a trivalent, bispecific antibody comprising a) a full length antibody specifically binding to a first antigen and consisting of two antibody heavy chains and two antibody light chains, b) a first polypeptide consisting of
  ba) an antibody heavy chain variable domain (VH), or
  bb) an antibody heavy chain variable domain (VH) and an antibody constant domain 1 (CH1), wherein said first polypeptide is fused with the N-terminus of its VH domain via a peptidic linker to the C-terminus of one of the two heavy chains of said full length antibody, c) a second polypeptide consisting of
  ca) an antibody light chain variable domain (VL), or
  cb) an antibody light chain variable domain (VL) and an antibody light chain constant domain (CL), wherein said second polypeptide is fused with the N-terminus of the VL domain via a peptidic linker to the C-terminus of the other of the two heavy chains of said full length antibody, and wherein the antibody heavy chain variable domain (VH) of the first polypeptide and the antibody light chain variable domain (VL) of the second polypeptide together form an antigen-binding site specifically binding to a second antigen, and wherein the first antigen or the second antigen is the human transferrin receptor.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:

i) heavy chain variable domain position 44 to light chain variable domain position 100, or
ii) heavy chain variable domain position 105 to light chain variable domain position 43, or
iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to Kabat). In one embodiment a trivalent, bispecific antibody without said optional disulfide stabilization between the variable domains VH and VL of the single chain Fab fragments is preferred.

One aspect as reported herein is a trispecific or tetraspecific antibody, comprising a) a first light chain and a first heavy chain of a full length antibody which specifically binds to a first antigen, and b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and c) wherein one to four antigen binding peptides which specifically bind to one or two further antigens (i.e. to a third and/or fourth antigen) are fused via a peptidic linker to the C- or N-terminus of the light chains or heavy chains of a) and/or b), wherein the first antigen or the second antigen or one of the further antigens is the human transferrin receptor.

The antibody under a) does not contain a modification as reported under b) and the heavy chain and the light chain and a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

One aspect as reported herein is a bispecific, tetravalent antibody comprising
- a) two light chains and two heavy chains of an antibody, which specifically bind to a first antigen (and comprise two Fab fragments),
- b) two additional Fab fragments of an antibody, which specifically bind to a second antigen, wherein said additional Fab fragments are fused both via a peptidic linker either to the C- or N-termini of the heavy chains of a), and
wherein in the Fab fragments the following modifications were performed
- i) in both Fab fragments of a), or in both Fab fragments of b), the variable domains VL and VH are replaced by each other, and/or the constant domains CL and CH1 are replaced by each other, or
- ii) in both Fab fragments of a) the variable domains VL and VH are replaced by each other, and the constant domains CL and CH1 are replaced by each other, and
  in both Fab fragments of b) the variable domains VL and VH are replaced by each other, or the constant domains CL and CH1 are replaced by each other, or
- iii) in both Fab fragments of a) the variable domains VL and VH are replaced by each other, or the constant domains CL and CH1 are replaced by each other, and
  in both Fab fragments of b) the variable domains VL and VH are replaced by each other, and the constant domains CL and CH1 are replaced by each other, or
- iv) in both Fab fragments of a) the variable domains VL and VH are replaced by each other, and in both Fab fragments of b) the constant domains CL and CH1 are replaced by each other, or
- v) in both Fab fragments of a) the constant domains CL and CH1 are replaced by each other, and in both Fab fragments of b) the variable domains VL and VH are replaced by each other,
wherein the first antigen or the second antigen is the human transferrin receptor.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
- i) in both Fab fragments of a), or in both Fab fragments of b), the variable domains VL and VH are replaced by each other,
  and/or
  the constant domains CL and CH1 are replaced by each other.

In one embodiment in the Fab fragments the following modifications are performed:
- i) in both Fab fragments of a) the variable domains VL and VH are replaced by each other,
  and/or
  the constant domains CL and CH1 are replaced by each other.

In one embodiment in the Fab fragments the following modifications are performed:
- i) in both Fab fragments of a) the constant domains CL and CH1 are replaced by each other.

In one embodiment in the Fab fragments the following modifications are performed:
- i) in both Fab fragments of b) the variable domains VL and VH are replaced by each other,
  and/or
  the constant domains CL and CH1 are replaced by each other.

In one embodiment in the Fab fragments the following modifications are performed:
- i) in both Fab fragments of b) the constant domains CL and CH1 are replaced by each other.

One aspect as reported herein is a bispecific, tetravalent antibody comprising:
- a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
- b) two light chains of said first antibody of a),
- c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
- d) two (modified) light chains of said second antibody of c), each comprising a CL-CH1 domain pair,
wherein the first antigen or the second antigen is the human transferrin receptor.

One aspect as reported herein is a bispecific antibody comprising
- a) the heavy chain and the light chain of a first full length antibody that specifically binds to a first antigen, and
- b) the heavy chain and the light chain of a second full length antibody that specifically binds to a second antigen, wherein the N-terminus of the heavy chain is connected to the C-terminus of the light chain via a peptidic linker,
wherein the first antigen or the second antigen is the human transferrin receptor.

The antibody under a) does not contain a modification as reported under b) and the heavy chain and the light chain are isolated chains.

One aspect as reported herein is a bispecific antibody comprising
- a) a full length antibody specifically binding to a first antigen and consisting of two antibody heavy chains and two antibody light chains, and
- b) an Fv fragment specifically binding to a second antigen comprising a $VH^2$ domain and a $VL^2$ domain, wherein both domains are connected to each other via a disulfide bridge,
  wherein only either the $VH^2$ domain or the $VL^2$ domain is fused via a peptidic linker to the heavy or light chain of the full length antibody specifically binding to a first antigen,
  wherein the first antigen or the second antigen is the human transferrin receptor.

In the bispecific the heavy chains and the light chains under a) are isolated chains.

In one embodiment the other of the $VH^2$ domain or the $VL^2$ domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

One aspect as reported herein is a bispecific trivalent antibody comprising
- a) two Fab fragments that specifically binds to a first antigen,
- b) one CrossFab fragment that specifically binds to a second antigen in which the CH1 and the CL domain are exchanged for each other,
- c) one Fc-region comprising a first Fc-region heavy chain and a second Fc-region heavy chain,
  wherein the C-terminus of CH1 domains of the two Fab fragments are connected to the N-terminus of the heavy chain Fc-region polypeptides, and
  wherein the C-terminus of the CL domain of the CrossFab fragment is connected to the N-terminus of the VH domain of one of the Fab fragments,
  and
  wherein the first antigen or the second antigen is the human transferrin receptor.

One aspect as reported herein is a bispecific trivalent antibody comprising
- a) two Fab fragments that specifically binds to a first antigen,
- b) one CrossFab fragment that specifically binds to a second antigen in which the CH1 and the CL domain are exchanged for each other,
- c) one Fc-region comprising a first Fc-region heavy chain and a second Fc-region heavy chain,
  wherein the C-terminus of CH1 domain of the first Fab fragment is connected to the N-terminus of one of the heavy chain Fc-region polypeptides and the C-terminus of the CL-domain of the CrossFab fragment is connected to the N-terminus of the other heavy chain Fc-region polypeptide, and
  wherein the C-terminus of the CH1 domain of the second Fab fragment is connected to the N-terminus of the VH domain of the first Fab fragment or to the N-terminus of the VH domain of the CrossFab fragment, and
  wherein the first antigen or the second antigen is the human transferrin receptor.

One aspect as reported herein is a bispecific antibody comprising
- a) a full length antibody specifically binding to a first antigen and consisting of two antibody heavy chains and two antibody light chains, and
- b) a Fab fragment specifically binding to a second antigen comprising a $VH^2$ domain and a $VL^2$ domain comprising a heavy chain fragment and a light chain fragment, wherein
  within the light chain fragment
    the variable light chain domain $VL^2$ is replaced by the variable heavy chain domain $VH^2$ of said antibody,
  and
  within the heavy chain fragment
    the variable heavy chain domain $VH^2$ is replaced by the variable light chain domain $VL^2$ of said antibody
  wherein the heavy chain Fab fragment is inserted between the CH1 domain of one of the heavy chains of the full length antibody and the respective Fc-region of the full length antibody, and the N-terminus of the light chain Fab fragment is conjugated to the C-terminus of the light chain of the full length antibody that is paired with the heavy chain of the full length antibody into which the heavy chain Fab fragment has been inserted, and
  wherein the first antigen or the second antigen is the human transferrin receptor.

One aspect as reported herein is a bispecific antibody comprising
- a) a full length antibody specifically binding to a first antigen and consisting of two antibody heavy chains and two antibody light chains, and
- b) a Fab fragment specifically binding to a second antigen comprising a $VH^2$ domain and a $VL^2$ domain comprising a heavy chain fragment and a light chain fragment, wherein
  within the light chain fragment
    the variable light chain domain $VL^2$ is replaced by the variable heavy chain domain $VH^2$ of said antibody,
  and
  within the heavy chain fragment
    the variable heavy chain domain $VH^2$ is replaced by the variable light chain domain $VL^2$ of said antibody
  wherein the C-terminus of the heavy chain fragment of the Fab fragment is conjugated to the N-terminus of one of the heavy chains of the full length antibody and the C-terminus of the light chain fragment of the Fab fragment is conjugated to the N-terminus of the light chain of the full length antibody that pairs with the heavy chain of the full length antibody to which the heavy chain fragment of the Fab fragment is conjugated, and
  wherein the first antigen or the second antigen is the human transferrin receptor.

In one embodiment of all aspects the antibody as reported herein is a multispecific antibody, which requires heterodimerization of at least two heavy chain polypeptides, and wherein the antibody specifically binds to human transferrin receptor and a second non-human transferrin receptor antigen.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in a multispecific antibody according to the invention, which comprises a "non-crossed Fab region" derived from a first antibody, which specifically binds to a first antigen, and a "crossed Fab region" derived from a second antibody, which specifically binds to a second antigen, in combination with the particular amino acid substitutions described above for the invention.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459A1, can be used alternatively or additionally. In one embodiment the multispecific antibody as reported herein comprises the R409D and K370E mutations in the CH3 domain of the "knobs chain" and the D399K and E357K mutations in the CH3 domain of the "hole-chain" (numbering according to Kabat EU index).

In one embodiment the multispecific antibody as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multispecific antibody as reported herein comprises the Y349C and T366W mutations in one of the two CH3 domains and the S354C, T366S, L368A and Y407V mutations in the other of the two CH3 domains, or the multispecific antibody as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody as reported herein.

In one embodiment of a multispecific antibody as reported herein the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, this embodiment relates to a multispecific antibody as reported herein, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of said CH3(+/−)-engineered multispecific antibody as reported herein the positively charged amino acid is selected from K, R and H, and the negatively charged amino acid is selected from E or D.

In one embodiment of said CH3(+/−)-engineered multispecific antibody as reported herein the positively charged amino acid is selected from K and R, and the negatively charged amino acid is selected from E or D.

In one embodiment of said CH3(+/−)-engineered multispecific antibody as reported herein the positively charged amino acid is K, and the negatively charged amino acid is E.

In one embodiment of said CH3(+/−)-engineered multispecific antibody as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a multispecific antibody as reported herein the approach described in WO 2013/157953 is used to support heterodimerization of the first heavy chain and the second heavy chain of the multispecific antibody. In one embodiment of said multispecific antibody as reported herein, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multispecific antibody as reported herein the approach described in WO 2012/058768 is used to support heterodimerization of the first heavy chain and the second heavy chain of the multispecific antibody. In one embodiment of said multispecific antibody as reported herein, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:
- substituting the amino acid T at position 411 by an amino acid selected from N, R, Q, K, D, E and W (numbering according to Kabat EU index),
- substituting the amino acid D at position 399 by an amino acid selected from R, W, Y, and K (numbering according to Kabat EU index),
- substituting the amino acid S at position 400 by an amino acid selected from E, D, R and K (numbering according to Kabat EU index),
- substituting the amino acid F at position 405 by an amino acid selected from I, M, T, S, V and W (numbering according to Kabat EU index;
- substituting the amino acid N at position 390 by an amino acid selected from R, K and D (numbering according to Kabat EU index; and
- substituting the amino acid K at position 392 by an amino acid selected from V, M, R, L, F and E (numbering according to Kabat EU index).

In another embodiment of said multispecific antibody as reported herein (engineered according to WO 2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said multispecific antibody as reported herein, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multispecific antibody as reported herein the approach described in WO 2011/143545 is used to support heterodimerization of the first heavy chain and the second heavy chain of the multispecific antibody. In one embodiment of said multispecific antibody as reported herein, amino acid modifications in the CH3 domains of both heavy chains are introduced at positions 368 and/or 409 (numbering according to Kabat EU index).

In one embodiment of a multispecific antibody as reported herein the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody as reported herein, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3 (KiH)-engineered multispecific antibody as reported herein, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment of a multispecific antibody as reported herein, which is of IgG2 isotype, the approach described in WO 2011/090762 is used to support heterodimerization of the first heavy chain and the second heavy chain of the multispecific antibody.

In one embodiment of a multispecific antibody as reported herein, the approach described in WO 2009/089004 is used to support heterodimerization of the first heavy chain and the second heavy chain of the multispecific antibody. In one embodiment of said multispecific antibody as reported herein, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment of a multispecific antibody as reported herein, the approach described in WO 2007/147901 is used to support heterodimerization of the first heavy chain and the second heavy chain of the multispecific antibody. In one embodiment of said multispecific antibody as reported herein, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment of a multispecific antibody as reported herein, the approach described in WO 2007/110205 is used to support heterodimerization of the first heavy chain and the second heavy chain of the multispecific antibody In one embodiment of all aspects and embodiments as reported herein the multispecific antibody is a bispecific antibody or a trispecific antibody. In one preferred embodiment of the invention the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Blood-Brain-Barrier Shuttle Modules

In one embodiment of all aspects of the antibody is a multispecific antibody having at least one binding specificity for the transferrin receptor and at least one binding specificity for a therapeutic target. In one embodiment the antibody comprises a first antigen binding site which binds the transferrin receptor and a second antigen binding site which binds a brain antigen. In a further embodiment the brain antigen is selected from the group consisting of Abeta, epidermal growth factor receptor (EGFR), human epidermal growth factor receptor 2 (HER2), alpha-synuclein, CD20, glucocerebrosidase or amyloid precursor protein (APP). In one preferred embodiment the multispecific antibody binds both i) the transferrin receptor and Abeta, or
ii) the transferrin receptor and CD20, or
iii) the transferrin receptor and alpha-synuclein, or
iv) the transferrin receptor and phospho-tau, or
v) the transferrin receptor and HER2, or
vi) the transferrin receptor and glucocerebrosidase.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a heavy chain variable domain of SEQ ID NO: 81 and a light chain variable domain of SEQ ID NO: 82 binding site for Abeta.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a heavy chain variable domain of SEQ ID NO: 79 and a light chain variable domain of SEQ ID NO: 80 binding site for human CD20. In one embodiment, the heavy chain variable region comprises a replacement of the amino acid residue at Kabat position 11 with any amino acid but leucine. In one embodiment, the substitution comprises a replacement of the amino acid residue at Kabat position 11 with a nonpolar amino acid. In one preferred embodiment, the substitution comprises a replacement of the amino acid residue at Kabat position 11 in the heavy chain variable domain of SEQ ID NO: 79 with an amino acid residue selected from the group consisting of valine, leucine, isoleucine, serine, and phenylalanine.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a heavy chain variable domain of SEQ ID NO: 83 and a light chain variable domain of SEQ ID NO: 84 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 85 and a humanized light chain variable domain derived from SEQ ID NO: 86 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 87 and a humanized light chain variable domain derived from SEQ ID NO: 88 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 89 and a humanized light chain variable domain derived from SEQ ID NO: 90 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 91 and a humanized light chain variable domain derived from SEQ ID NO: 92 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and at least one pair of a humanized heavy chain variable domain derived from SEQ ID NO: 93 and a humanized light chain variable domain derived from SEQ ID NO: 94 binding site for human alpha-synuclein.

In one embodiment the antibody is a bispecific antibody comprising at least one pair of a heavy chain variable domain of SEQ ID NO: 24 and a light chain variable domain of SEQ ID NO: 37 forming a binding site for the transferrin receptor and a binding site for human glucocerebrosidase.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and at least one pair of a heavy chain variable domain of SEQ ID NO: 83 and a light chain variable domain of SEQ ID NO: 84 binding site for human alpha-synuclein.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and at least one pair of a humanized heavy chain variable domain derived from SEQ ID NO: 85 and a humanized light chain variable domain derived from SEQ ID NO: 86 binding site for human alpha-synuclein.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and at least one pair of a humanized heavy chain variable domain derived from SEQ ID NO: 87 and a humanized light chain variable domain derived from SEQ ID NO: 88 binding site for human alpha-synuclein.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and at least one pair of a humanized heavy chain variable domain derived from SEQ ID NO: 89 and a humanized light chain variable domain derived from SEQ ID NO: 90 binding site for human alpha-synuclein.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and at least one pair of a humanized heavy chain variable domain derived from SEQ ID NO: 91 and a humanized light chain variable domain derived from SEQ ID NO: 92 binding site for human alpha-synuclein.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and at least one pair of a humanized heavy chain variable domain derived from SEQ ID NO: 93 and a humanized light chain variable domain derived from SEQ ID NO: 94 binding site for human alpha-synuclein.

In one embodiment the antibody is a bispecific antibody comprising at least one pair of a heavy chain variable domain of SEQ ID NO: 7 and a light chain variable domain of SEQ ID NO: 34 forming a binding site for the transferrin receptor and a binding site for human glucocerebrosidase.

Monovalent binding entities that specifically bind to a blood-brain-barrier-receptor can be characterized with respect to their binding and transcytosis properties:
- efficient cell binding of BBBR expressing cells as monovalent binding entity,
- efficient in vitro transcytosis as monovalent binding entity, human-cynomolgus cross-reactivity (e.g. in BIAcore and FACS experiments).

The transcytosis screening can be performed in an hCMEC/D3 based assay. The assay can be performed in a pulse-chase mode. The hCMEC/D3 brain endothelial cells are incubated with the monovalent binding entity for 1 hour, washed thereafter and the following parameters are determined 0 hours and 4 hours post washing:
i) amount of monovalent binding entity taken up into the cells during the loading phase,
ii) basolateral amount of monovalent binding entity 4 hours post loading and washing;
iii) apical amount of monovalent binding entity 4 hours post loading and washing;
iv) amount of monovalent binding entity in the cells (by cell lysis) 0 hours and 4 hours after loading and washing;
v) total amount of monovalent binding entity 0 hours and 4 hours after loading and washing.

In order to be eligible as monovalent binding entity in a blood-brain-barrier shuttle module as reported herein the anti-transferrin receptor antibody (e.g. as monovalent binding entity) has to be i) taken up by the hCMEC/D3 cells (endocytosis), ii) transported outside the hCMEC/D3 cells (exocytosis), and iii) stable inside the hCMEC/D3 cells (no or low transport to the endosome for degradation).

Thus, in one embodiment the monovalent binding entity is characterized in a hCMEC/D3 based assay by i) an (substantial) uptake into the hCMEC/D3 cells during a one hour loading period, ii) a release into the apical and/or basolateral compartment after the loading period and a washing step within 4 hours after the washing, and iii) a low (intracellular) degradation rate.

In one embodiment the loading is at a concentration of about 2.67 µg/mL monovalent binding entity for one hour.

It has been found that a monovalent binding entity in order to be eligible as monovalent binding entity of a blood-brain-barrier shuttle module as reported herein has to show in the above described hCMEC/D3 based assay the following threshold values:
i) an amount of monovalent binding entity taken up into the cells during the loading phase of 400 pg or more,
ii) basolateral amount of monovalent binding entity 4 hours post loading and washing of 100 pg or more, and
iii) apical amount of monovalent binding entity 4 hours post loading and washing of 150 pg or more.

The mouse anti-human transferrin-receptor antibody 128.1 (for variable region sequences see WO 93/10819 and SEQ ID NO: 64 and 65) can be taken as reference. In this case the monovalent binding entity in order to be eligible as monovalent binding entity of a blood-brain-barrier shuttle module as reported herein has to show in the above described hCMEC/D3 based assay the following threshold values:
  i) an amount of monovalent binding entity taken up into the cells during the loading phase of 60% or more of the loading of antibody 128.1,
  ii) basolateral amount of monovalent binding entity 4 hours post loading and washing of 60% or more of the basolateral amount of antibody 128.1; and
  iii) apical amount of monovalent binding entity 4 hours post loading and washing of 60% or more of the apical amount of antibody 128.1.

The hCMEC/D3 based assay can be performed as follows (this is one embodiment of all aspects as reported herein):

Medium and supplements for hCMEC/D3 (see WO 2006/056879 and Weksler, B. B., et al., FASEB J. 19 (2005) 1872-1874) can be obtained from Lonza. hCMEC/D3 cells (passages 26-29) are/can be cultured to confluence on collagen-coated coverslips (microscopy) or flasks in EBM2 medium containing 2.5 FBS, a quarter of the supplied growth factors and fully complemented with supplied hydrocortisone, gentamycin and ascorbic acid.

For all transcytosis assays, high density pore ($1 \times 10^8$ pores/cm$^2$) PET membrane filter inserts (0.4 μm pore size, 12 mm diameter) are/can be used in 12-well cell culture plates. Media volumes are calculated to be 400 μL and 1600 μL for apical and basolateral chambers, respectively. Apical chambers of filter inserts are/can be coated with rat tail collagen I (7.5 μg/cm$^2$) followed by fibronectin (5 μg/mL), each incubation lasting for one hour at RT. hCMEC/D3 cells are/can be grown to confluent monolayers ($2 \times 10^5$ cells/cm$^2$) for 10-12 days in EBM2 medium. Empty filters are/can be blocked in PBS containing 1% BSA for 1 hour or overnight (o/n) before assay and then calibrated for at least 1 hour in EBM2 before the assay.

Figure 1B:
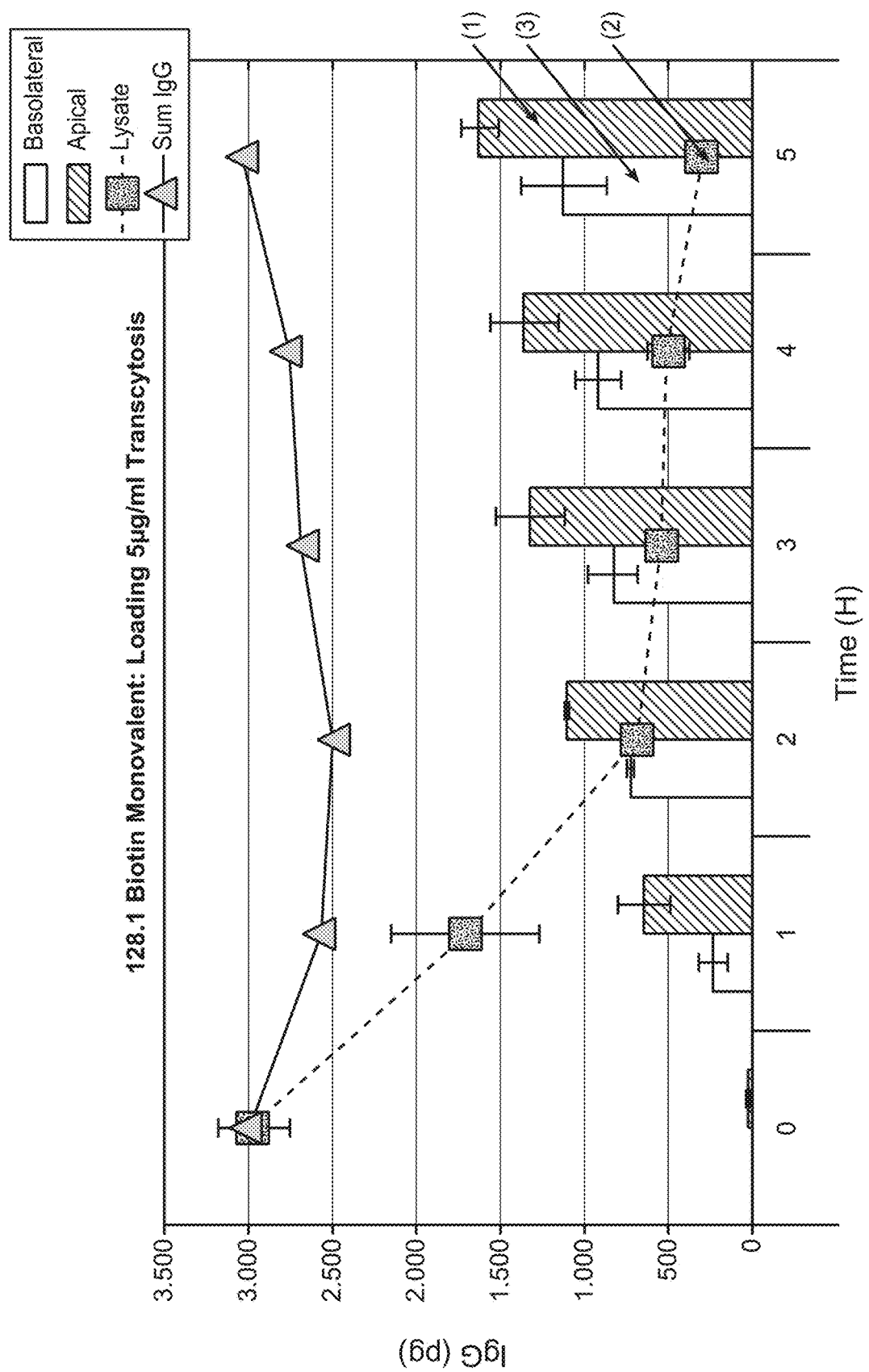
Figure 2:
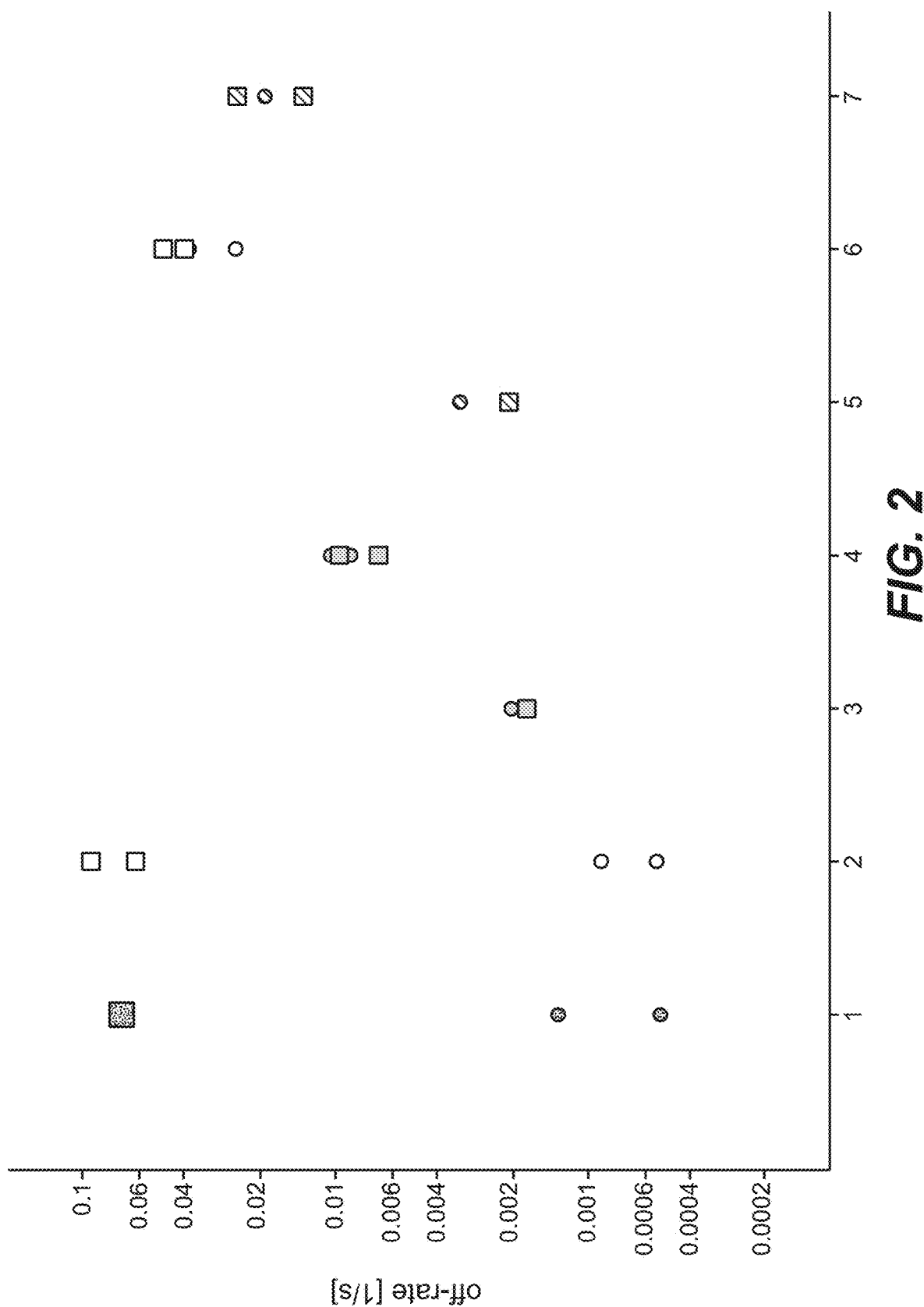
FIG. 2 shows off-rates of different anti-transferrin receptor antibodies determined at 25° C. using BIAcore; 1: 128.1; 2: 128.1 fused to anti-pTau antibody mAb86; 3: 567; 4: 932; 5: 567 fused to anti-pTau antibody mAb86; 6: 1026; 7: 1027; squares: binding to cynomolgus transferrin receptor; circle: binding to human transferrin receptor; y-axis: off-rate [l/s].
Figure 3:
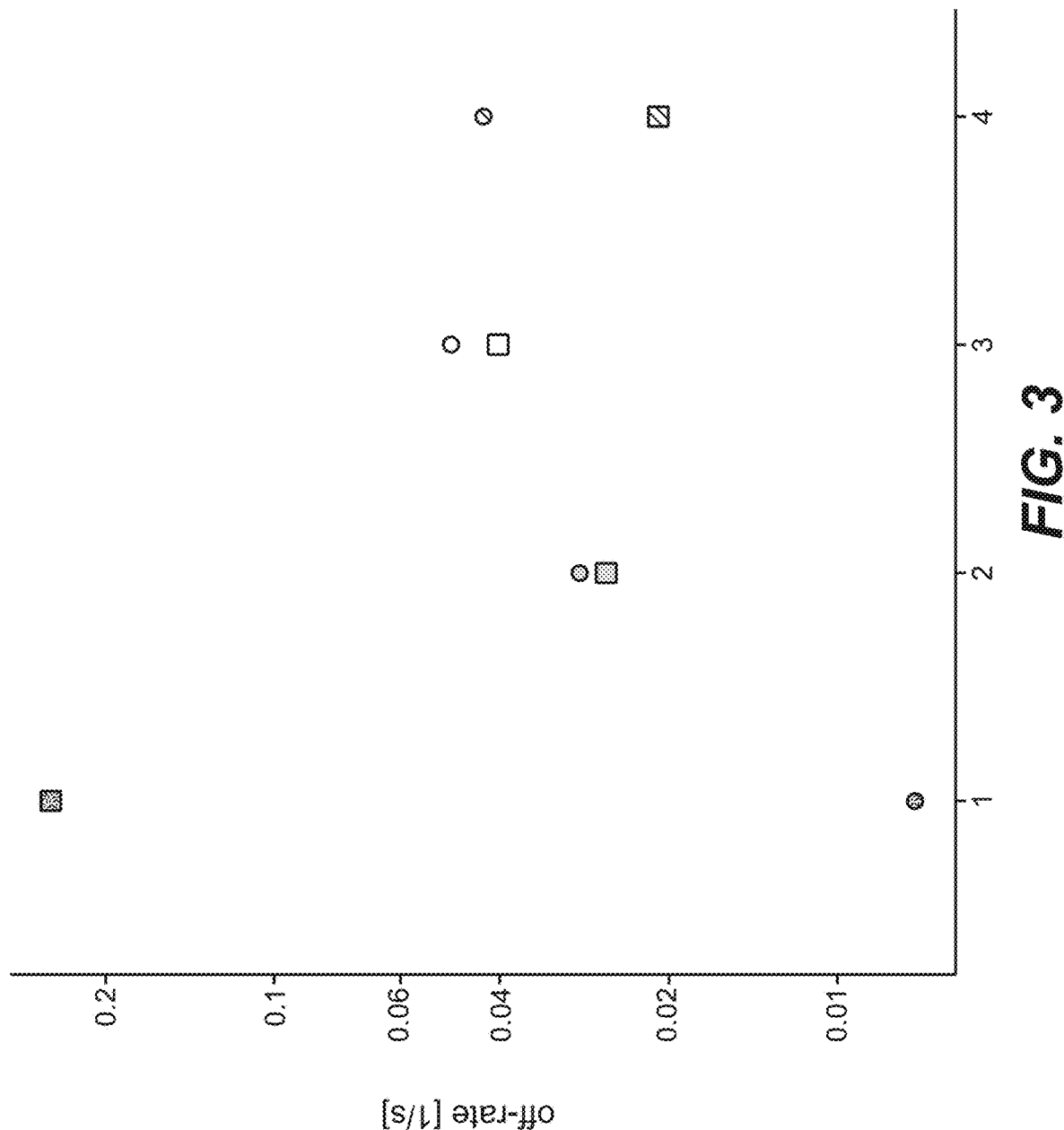
FIG. 3 shows off-rates of different anti-transferrin receptor antibodies determined at 37° C. using BIAcore; 1: 128.1; 2: 932; 3: 1026; 4: 1027; squares: binding to cynomolgus transferrin receptor; circle: binding to human transferrin receptor; y-axis: off-rate [l/s]

The assay (for assay scheme see FIG. 1) was performed in serum-free EBM2 medium which was otherwise reconstituted as described herein. On day of the assay, cells are serum-starved for 60 min. to deplete the natural ligand of the blood-brain-barrier-receptor in question. Filter inserts with or without (but blocked overnight in complete medium) cells were incubated apically with monoclonal antibodies in question (monovalent binding entity) for 1 hour at 37° C. The monolayers were washed at room temperature (RT) in serum-free medium apically (400 μL) and basolaterally (1600 μL) three times for 3-5 min. each. Pre-warmed medium was added to the apical chamber and the filters transferred to a fresh 12 well plate (blocked overnight with PBS containing 1% BSA) containing 1600 μL pre-warmed medium. At this point, filters with or without cells were lysed in 500 μL RIPA buffer in order to determine specific antibody (monovalent binding entity) uptake. The remaining filters were incubated at 37° C. or at 4° C. and samples were collected at various time points to determine apical and/or basolateral release of the antibody (monovalent binding entity). The content of antibody in the samples can be quantified using a highly sensitive IgG ELISA (see Example 9). For each time point, data should be generated from two empty filters and three filter cell cultures.

C. Recombinant Methods and Compositions

Antibodies may be produced using recombinant methods and compositions, e.g., as described in U.S. Pat. No. 4,816,567. In one embodiment, isolated nucleic acid encoding an anti-transferrin receptor antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-transferrin receptor antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-transferrin receptor antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES' technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36

(1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

D. Assays

Anti-transferrin receptor antibodies provided herein may be identified, screened for, or characterized for their physical/chemical properties and/or biological activities by various assays known in the art.

1. Binding Assay

In one aspect, an antibody of the invention is tested for its antigen binding activity, e.g., by known methods such as ELISA, alphaLISA, Western blot, antibody or reverse phase array, etc.

In an exemplary ELISA or alphaLISA assay, transferrin receptor in solution (cell supernatant, cell or tissue lysates, body fluids etc.) is bound by a capture antibody, which specifically binds to a first epitope on the transferrin receptor, or transferrin receptor in a certain conformation and a detection antibody coupled to a detection entity, which specifically binds to a second epitope or conformation of the transferrin receptor. The readout is based on the detection entity (chemiluminescence, fluorescence, energy transfer induced luminescence etc.).

In the case of antibody array, antibodies are spotted onto glass or nitrocellulose chips. The slides are blocked and incubated with transferrin receptor containing solution, washed to remove unbound antibodies and bound antibodies are detected with a fluorescently labeled corresponding secondary antibody. The fluorescence signal is measured by a fluorescence slide scanner. Similarly for a reverse phase array, recombinant transferrin receptor, cell supernatant, cell or tissue lysates, body fluids etc. are spotted onto glass or nitrocellulose chips. The slides are blocked and individual arrays are incubated with an antibody against a specific epitope on the transferrin receptor. Unbound antibodies are washed off and bound antibodies are detected with a fluorescently labeled corresponding secondary antibody. The fluorescence signal is measured by a fluorescence slide scanner (Dernick, G., et al., J. Lipid Res. 52 (2011) 2323-2331).

E. Methods and Compositions for Diagnostics and Detection

In certain embodiments, any of the anti-transferrin receptor antibodies provided herein is useful for detecting the presence of human transferrin receptor in a biological sample. The term "detecting" as used herein encompasses quantitative or qualitative detection. In certain embodiments, a biological sample comprises a cell or tissue, such as brain tissue.

In one embodiment, an anti-transferrin receptor antibody for use in a method of diagnosis or detection is provided. In a further aspect, a method of detecting the presence of the transferrin receptor in a biological sample is provided. In certain embodiments, the method comprises contacting the biological sample with an anti-transferrin receptor antibody as described herein under conditions permissive for binding of the anti-transferrin receptor antibody to the transferrin receptor, and detecting whether a complex is formed between the anti-transferrin receptor antibody and the transferrin receptor. Such method may be an in vitro or in vivo method. In one embodiment, an anti-transferrin receptor antibody is used to select subjects eligible for therapy with an anti-transferrin receptor antibody, e.g. where the transferrin receptor is a biomarker for selection of patients.

Exemplary disorders that may be diagnosed using an antibody of the invention include neurodegeneration with brain iron accumulation type 1 (NBIA1), pure autonomic failure, Down's syndrome, complex of Guam, and several Lewy body disorders, such as diffuse Lewy body disease (DLBD), the Lewy body variant of Alzheimer's disease (LBVAD), certain forms of Gaucher's disease, and Parkinson's Disease dementia (PDD).

In certain embodiments, labeled anti-transferrin receptor antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-transferrin receptor antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-TfR antibodies provided herein may be used in therapeutic methods. In one aspect, an anti-TfR antibody for use as a medicament is provided. For example, the invention provides a method of transporting a therapeutic compound across the blood-brain-barrier comprising exposing the anti-TfR antibody coupled to a therapeutic compound (e.g. a multispecific antibody which binds both the TfR and a brain antigen) to the BBB such that the antibody transports the therapeutic compound coupled thereto across the BBB. In another example, the invention provides a method of transporting a neurological disorder drug across the blood-brain-barrier comprising exposing an anti-TfR antibody of the invention coupled to a brain disorder drug (e.g. a multispecific antibody which binds both the TfR and a brain antigen) to the BBB such that the antibody transports the neurological disorder drug coupled thereto across the BBB. In one embodiment, the BBB is in a mammal (e.g. a human), e.g. one which has a neurological disorder, including, without limitation: Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, traumatic brain injury, etc. In one embodiment, the neurological disorder is selected from: a neuropathy, an amyloidosis, cancer (e.g. involving the CNS or brain), an ocular disease or disorder, a viral or microbial infection, inflammation (e.g. of the CNS or brain), ischemia, neurodegenerative disease, seizure, behavioral disorder, lysosomal storage disease, etc. The antibodies of the invention are particularly suited to treatment of such neurological disorders due to their ability to transport one or more associated active ingredients/coupled therapeutic compounds across the BBB and into the CNS/brain where such disorders find their molecular, cellular, or viral/microbial basis. Neuropathy disorders are diseases or abnormalities of the nervous system characterized by inappropriate or uncontrolled nerve signaling or lack thereof, and include, but are not limited to, chronic pain (including nociceptive pain), pain caused by an injury to body tissues, including cancer-related pain, neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea.

For a neuropathy disorder, a neurological drug may be selected that is an analgesic including, but not limited to, a narcotic/opioid analgesic (i.e., morphine, fentanyl, hydrocodone, meperidine, methadone, oxymorphone, pentazocine, propoxyphene, tramadol, codeine and oxycodone), a non-steroidal anti-inflammatory drug (NSAID) (i.e., ibuprofen, naproxen, diclofenac, diflunisal, etodolac, fenoprofen, flurbiprofen, indomethacin, ketorolac, mefenamic acid, meloxicam, nabumetone, oxaprozin, piroxicam, sulindac, and tolmetin), a corticosteroid (i.e., cortisone, prednisone, prednisolone, dexamethasone, methylprednisolone and triamcinolone), an anti-migraine agent (i.e., sumatriptin, almotriptan, frovatriptan, sumatriptan, rizatriptan, eletriptan, zolmitriptan, dihydroergotamine, eletriptan and ergotamine), acetaminophen, a salicylate (i.e., aspirin, choline salicylate, magnesium salicylate, diflunisal, and salsalate), an anti-convulsant (i.e., carbamazepine, clonazepam, gabapentin, lamotrigine, pregabalin, tiagabine, and topiramate), an anaesthetic (i.e., isoflurane, trichloroethylene, halothane, sevoflurane, benzocaine, chloroprocaine, cocaine, cyclomethycaine, dimethocaine, propoxycaine, procaine, novocaine, proparacaine, tetracaine, articaine, bupivacaine, carticaine, cinchocaine, etidocaine, levobupivacaine, lidocaine, mepivacaine, piperocaine, prilocaine, ropivacaine, trimecaine, saxitoxin and tetrodotoxin), and a cox-2-inhibitor (i.e., celecoxib, rofecoxib, and valdecoxib). For a neuropathy disorder with vertigo involvement, a neurological drug may be selected that is an anti-vertigo agent including, but not limited to, meclizine, diphenhydramine, promethazine and diazepam. For a neuropathy disorder with nausea involvement, a neurological drug may be selected that is an anti-nausea agent including, but not limited to, promethazine, chlorpromazine, prochlorperazine, trimethobenzamide, and metoclopramide.

Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeldt Jacob disease, Parkinson's disease, transmissible spongiform encephalopathy, HIV-related dementia, amyotrophic lateral sclerosis (ALS), inclusion-body myositis (IBM), and ocular diseases relating to beta-amyloid deposition (i.e., macular degeneration, drusen-related optic neuropathy, and cataract).

For amyloidosis, a neurological drug may be selected that includes, but is not limited to, an antibody or other binding molecule (including, but not limited to a small molecule, a peptide, an aptamer, or other protein binder) that specifically binds to a target selected from: beta secretase, tau, presenilin, amyloid precursor protein or portions thereof, amyloid beta peptide or oligomers or fibrils thereof, death receptor 6 (DR6), receptor for advanced glycation end products (RAGE), parkin, and huntingtin; a cholinesterase inhibitor (i.e., galantamine, donepezil, rivastigmine and tacrine); an NMDA receptor antagonist (i.e., memantine), a monoamine depletor (i.e., tetrabenazine); an ergoloid mesylate; an anticholinergic anti-parkinsonism agent (i.e., procyclidine, diphenhydramine, trihexylphenidyl, benztropine, biperiden and trihexyphenidyl); a dopaminergic anti-parkinsonism agent (i.e., entacapone, selegiline, pramipexole, bromocriptine, rotigotine, selegiline, ropinirole, rasagiline, apomorphine, carbidopa, levodopa, pergolide, tolcapone and amantadine); a tetrabenazine; an anti-inflammatory (including, but not limited to, a nonsteroidal anti-inflammatory drug (i.e., indomethicin and other compounds listed above); a hormone (i.e., estrogen, progesterone and leuprolide); a vitamin (i.e., folate and nicotinamide); a dimebolin; a homotaurine (i.e., 3-aminopropanesulfonic acid; 3APS); a serotonin receptor activity modulator (i.e., xaliproden); an, an interferon, and a glucocorticoid.

Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary, intradural tumors or CNS metastases of peripheral tumors such as CD20 or HER2 positive cancers.

For cancer, a neurological drug may be selected that is a chemotherapeutic agent.

Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Angew. Chem. Intl. Ed. Engl., 33 (1994) 183-186); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-25 azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; 5 pipobroman; gacytosine; arabinoside ("Ara-C"); thiotepa; taxoids, e.g., TAXOL® paclitaxel (Bristol-Myers-Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition of chemotherapeutic agents are anti-hormonal agents that act to regulate, reduce, block, or inhibit the effects of hormones that can promote the growth of cancer, and are often in the form of systemic or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor downregulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, 5 SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Another group of compounds that may be selected as neurological drugs for cancer treatment or prevention are anti-cancer immunoglobulins (including, but not limited to, trastuzumab, pertuzumab, bevacizumab, alemtuzumab, cetuximab, gemtuzumab ozogamicin, ibritumomab tiuxetan, panitumumab and rituximab). In some instances, antibodies in conjunction with a toxic label or conjugate may be used to target and kill desired cells (i.e., cancer cells), including, but not limited to, tositumomab with a 131I radiolabel, or trastuzumab emtansine.

Ocular diseases or disorders are diseases or disorders of the eye, which for the purposes herein is considered a CNS organ segregated by the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and opthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia.

For an ocular disease or disorder, a neurological drug may be selected that is an antiangiogenic ophthalmic agent (i.e., bevacizumab, ranibizumab and pegaptanib), an ophthalmic glaucoma agent (i.e., carbachol, epinephrine, demecarium bromide, apraclonidine, brimonidine, brinzolamide, levobunolol, timolol, betaxolol, dorzolamide, bimatoprost, carteolol, metipranolol, dipivefrin, travoprost and latanoprost), a carbonic anhydrase inhibitor (i.e., methazolamide and acetazolamide), an ophthalmic antihistamine (i.e., naphazoline, phenylephrine and tetrahydrozoline), an ocular lubricant, an ophthalmic steroid (i.e., fluorometholone, prednisolone, loteprednol, dexamethasone, difluprednate, rimexolone, fluocinolone, medrysone and triamcinolone), an ophthalmic anesthetic (i.e., lidocaine, proparacaine and tetracaine), an ophthalmic anti-infective (i.e., levofloxacin, gatifloxacin, ciprofloxacin, moxifloxacin, chloramphenicol, bacitracin/polymyxin B, sulfacetamide, tobramycin, azithromycin, besifloxacin, norfloxacin, sulfisoxazole, gentamicin, idoxuridine, erythromycin, natamycin, gramicidin, neomycin, ofloxacin, trifluridine, ganciclovir, vidarabine), an ophthalmic anti-inflammatory agent (i.e., nepafenac, ketorolac, flurbiprofen, suprofen, cyclosporine, triamcinolone, diclofenac and bromfenac), and an ophthalmic antihistamine or decongestant (i.e., ketotifen, olopatadine, epinastine, naphazoline, cromolyn, tetrahydrozoline, pemirolast, bepotastine, naphazoline, phenylephrine, nedocromil, lodoxamide, phenylephrine, emedastine and azelastine).

Viral or microbial infections of the CNS include, but are not limited to, infections by viruses (i.e., influenza, HIV, poliovirus, rubella,), bacteria (i.e., *Neisseria* sp., *Streptococcus* sp., *Pseudomonas* sp., *Proteus* sp., *E. coli, S. aureus, Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., *Toxoplasma gondii*) or amoebas resulting in CNS pathophysiologies including, but not limited to, meningitis, encephalitis, myelitis, vasculitis and abscess, which can be acute or chronic.

For a viral or microbial disease, a neurological drug may be selected that includes, but is not limited to, an antiviral compound (including, but not limited to, an adamantane antiviral (i.e., rimantadine and amantadine), an antiviral interferon (i.e., peg-interferon alfa-2b), a chemokine receptor antagonist (i.e., maraviroc), an integrase strand transfer inhibitor (i.e., raltegravir), a neuraminidase inhibitor (i.e., oseltamivir and zanamivir), a non-nucleoside reverse transcriptase inhibitor (i.e., efavirenz, etravirine, delavirdine and nevirapine), a nucleoside reverse transcriptase inhibitors (tenofovir, abacavir, lamivudine, zidovudine, stavudine, entecavir, emtricitabine, adefovir, zalcitabine, telbivudine and didanosine), a protease inhibitor (i.e., darunavir, atazanavir, fosamprenavir, tipranavir, ritonavir, nelfinavir, amprenavir, indinavir and saquinavir), a purine nucleoside (i.e., valacyclovir, famciclovir, acyclovir, ribavirin, ganciclovir, valganciclovir and cidofovir), and a miscellaneous antiviral (i.e., enfuvirtide, foscarnet, palivizumab and fomivirsen)), an antibiotic (including, but not limited to, an aminopenicillin (i.e., amoxicillin, ampicillin, oxacillin, nafcillin, cloxacillin, dicloxacillin, flucoxacillin, temocillin, azlocillin, carbenicillin, ticarcillin, mezlocillin, piperacillin and bacampicillin), a cephalosporin (i.e., cefazolin, cephalexin, cephalothin, cefamandole, ceftriaxone, cefotaxime, cefpodoxime, ceftazidime, cefadroxil, cephradine, loracarbef, cefotetan, cefuroxime, cefprozil, cefaclor, and cefoxitin), a carbapenem/penem (i.e., imipenem, meropenem, ertapenem, faropenem and doripenem), a monobactam (i.e., aztreonam, tigemonam, norcardicin A and tabtoxinine-betalactam, a betalactamase inhibitor (i.e., clavulanic acid, tazobactam and sulbactam) in conjunction with another beta-lactam antibiotic, an aminoglycoside (i.e., amikacin, gentamicin, kanamycin, neomycin, netilmicin, streptomycin, tobramycin, and paromomycin), an ansamycin (i.e., geldanamycin and herbimycin), a carbacephem (i.e., loracarbef), a glycopeptides (i.e., teicoplanin and vancomycin), a macrolide (i.e., azithromycin, clarithromycin, dirithromycin, erythromycin, roxithromycin, troleandomycin, telithromycin and spectinomycin), a monobactam (i.e., aztreonam), a quinolone (i.e., ciprofloxacin, enoxacin, gatifloxacin, levofloxacin, lomefloxacin, moxifloxacin, norfloxacin, ofloxacin, trovafloxacin, grepafloxacin, sparfloxacin and temafloxacin), a sulfonamide (i.e., mafenide, sulfonamidochrysoidine, sulfacetamide, sulfadiazine, sulfamethizole, sulfanilamide, sulfasalazine, sulfisoxazole, trimethoprim, trimethoprim and sulfamethoxazole), a tetracycline (i.e., tetracycline, demeclocycline, doxycycline, minocycline and oxytetracycline), an antineoplastic or cytotoxic antibiotic (i.e., doxorubicin, mitoxantrone, bleomycin, daunorubicin, dactinomycin, epirubicin, idarubicin, plicamycin, mitomycin, pentostatin and valrubicin) and a miscellaneous antibacterial compound (i.e., bacitracin, colistin and polymyxin B)), an antifungal (i.e., metronidazole, nitazoxanide, tinidazole, chloroquine, iodoquinol and paromomycin), and an antiparasitic (including, but not limited to, quinine, chloroquine, amodiaquine, pyrimethamine, sulphadoxine, proguanil, mefloquine, atovaquone, primaquine, artemesinin, halofantrine, doxycycline, clindamycin, mebendazole, pyrantel pamoate, thiabendazole, diethylcarbamazine, ivermectin, rifampin, amphotericin B, melarsoprol, eformithine and albendazole).

Inflammation of the CNS includes, but is not limited to, inflammation that is caused by an injury to the CNS, which can be a physical injury (i.e., due to accident, surgery, brain trauma, spinal cord injury, concussion) and an injury due to or related to one or more other diseases or disorders of the CNS (i.e., abscess, cancer, viral or microbial infection).

For CNS inflammation, a neurological drug may be selected that addresses the inflammation itself (i.e., a nonsteroidal anti-inflammatory agent such as ibuprofen or naproxen), or one which treats the underlying cause of the inflammation (i.e., an anti-viral or anti-cancer agent).

Ischemia of the CNS, as used herein, refers to a group of disorders relating to aberrant blood flow or vascular behavior in the brain or the causes therefor, and includes, but is not limited to: focal brain ischemia, global brain ischemia, stroke (i.e., subarachnoid hemorrhage and intracerebral hemorrhage), and aneurysm.

For ischemia, a neurological drug may be selected that includes, but is not limited to, a thrombolytic (i.e., urokinase, alteplase, reteplase and tenecteplase), a platelet aggregation inhibitor (i.e., aspirin, cilostazol, clopidogrel, prasugrel and dipyridamole), a statin (i.e., lovastatin, pravastatin, fluvastatin, rosuvastatin, atorvastatin, simvastatin, cerivastatin and pitavastatin), and a compound to improve blood flow or vascular flexibility, including, e.g., blood pressure medications.

Neurodegenerative diseases are a group of diseases and disorders associated with neural cell loss of function or death in the CNS, and include, but are not limited to: adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia.

For a neurodegenerative disease, a neurological drug may be selected that is a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF).

Seizure diseases and disorders of the CNS involve inappropriate and/or abnormal electrical conduction in the CNS, and include, but are not limited to epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures). For a seizure disorder, a neurological drug may be selected that is an anticonvulsant or antiepileptic including, but not limited to, barbiturate anticonvulsants (i.e., primidone, metharbital, mephobarbital, allobarbital, amobarbital, aprobarbital, alphenal, barbital, brallobarbital and phenobarbital), benzodiazepine anticonvulsants (i.e., diazepam, clonazepam, and lorazepam), carbamate anticonvulsants (i.e. felbamate), carbonic anhydrase inhibitor anticonvulsants (i.e., acetazolamide, topiramate and zonisamide), dibenzazepine anticonvulsants (i.e., rufinamide, carbamazepine, and oxcarbazepine), fatty acid derivative anticonvulsants (i.e., divalproex and valproic acid), gamma-aminobutyric acid analogs (i.e., pregabalin, gabapentin and vigabatrin), gamma-aminobutyric acid reuptake inhibitors (i.e., tiagabine), gamma-aminobutyric acid transaminase inhibitors (i.e., vigabatrin), hydantoin anticonvulsants (i.e. phenytoin, ethotoin, fosphenytoin and mephenytoin), miscellaneous anticonvulsants (i.e., lacosamide and magnesium sulfate), progestins (i.e., progesterone), oxazolidinedione anticonvulsants (i.e., paramethadione and trimethadione), pyrrolidine anticonvulsants (i.e., levetiracetam), succinimide anticonvulsants (i.e., ethosuximide and methsuximide), triazine anticonvulsants (i.e., lamotrigine), and urea anticonvulsants (i.e., phenacemide and pheneturide).

Behavioral disorders are disorders of the CNS characterized by aberrant behavior on the part of the afflicted subject and include, but are not limited to: sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like).

For a behavioral disorder, a neurological drug may be selected from a behavior-modifying compound including, but not limited to, an atypical antipsychotic (i.e., risperidone, olanzapine, apripiprazole, quetiapine, paliperidone, asenapine, clozapine, iloperidone and ziprasidone), a phenothiazine antipsychotic (i.e., prochlorperazine, chlorpromazine, fluphenazine, perphenazine, trifluoperazine, thioridazine and mesoridazine), a thioxanthene (i.e., thiothixene), a miscellaneous antipsychotic (i.e., pimozide, lithium, molindone, haloperidol and loxapine), a selective serotonin reuptake inhibitor (i.e., citalopram, escitalopram, paroxetine, fluoxetine and sertraline), a serotonin-norepinephrine reuptake inhibitor (i.e., duloxetine, venlafaxine, desvenlafaxine, a tricyclic antidepressant (i.e., doxepin, clomipramine, amoxapine, nortriptyline, amitriptyline, trimipramine, imipramine, protriptyline and desipramine), a tetracyclic antidepressant (i.e., mirtazapine and maprotiline), a phenylpiperazine antidepressant (i.e., trazodone and nefazodone), a monoamine oxidase inhibitor (i.e., isocarboxazid, phenelzine, selegiline and tranylcypromine), a benzodiazepine (i.e., alprazolam, estazolam, flurazeptam, clonazepam, lorazepam and diazepam), a norepinephrine-dopamine reuptake inhibitor (i.e., bupropion), a CNS stimulant (i.e., phentermine, diethylpropion, methamphetamine, dextroamphetamine, amphetamine, methylphenidate, dexmethylphenidate, lisdexamfetamine, modafinil, pemoline, phendimetrazine, benzphetamine, phendimetrazine, armodafinil, diethylpropion, caffeine, atomoxetine, doxapram, and mazindol), an anxiolytic/sedative/hypnotic (including, but not limited to, a barbiturate (i.e., secobarbital, phenobarbital and mephobarbital), a benzodiazepine (as described above), and a miscellaneous anxiolytic/sedative/hypnotic (i.e. diphenhydramine, sodium oxybate, zaleplon, hydroxyzine, chloral hydrate, aolpidem, buspirone, doxepin, eszopiclone, ramelteon, meprobamate and ethclorvynol)), a secretin (see, e.g., Ratliff-Schaub et al. Autism 9 (2005) 256-265), an opioid peptide (see, e.g., Cowen et al., J. Neurochem. 89 (2004) 273-285), and a neuropeptide (see, e.g., Hethwa et al. Am. J. Physiol. 289 (2005) E301-305).

Lysosomal storage disorders are metabolic disorders which are in some cases associated with the CNS or have CNS-specific symptoms; such disorders include, but are not limited to: Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

For a lysosomal storage disease, a neurological drug may be selected that is itself or otherwise mimics the activity of the enzyme that is impaired in the disease. Exemplary recombinant enzymes for the treatment of lysosomal storage disorders include, but are not limited to those set forth in e.g., U.S. Patent Application publication no. 2005/0142141 (i.e., alpha-L20 iduronidase, iduronate-2-sulphatase, N-sulfatase, alpha-N-acetylglucosaminidase, N-acetylgalactosamine-6-sulfatase, beta-galactosidase, arylsulphatase B, beta-glucuronidase, acid alpha glucosidase, glucocerebrosidase, alpha-galactosidase A, hexosaminidase A, acid sphingomyelinase, beta-galactocerebrosidase, beta-galactosidase, arylsulfatase A, acid ceramidase, aspartoacylase, palmitoyl-protein thioesterase 1 and tripeptidyl amino peptidase 1).

In one aspect, an antibody of the invention is used to detect a neurological disorder before the onset of symptoms and/or to assess the severity or duration of the disease or disorder. In one aspect, the antibody permits detection and/or imaging of the neurological disorder, including imaging by radiography, tomography, or magnetic resonance imaging (MRI).

In one aspect, a low affinity anti-TfR antibody of the invention for use as a medicament is provided. In further aspects, a low affinity anti-TfR antibody for use in treating a neurological disease or disorder (e.g., Alzheimer's disease) without depleting red blood cells (i.e., reticulocytes) is provided. In certain embodiments, a modified low affinity anti-TfR antibody for use in a method of treatment as described herein is provided. In certain embodiments, the invention provides a low affinity anti-TfR antibody modified to improve its safety for use in a method of treating an individual having a neurological disease or disorder comprising administering to the individual an effective amount of the anti-TfR antibody (optionally coupled to a neurological disorder drug). In one such embodiment, the method further comprises administering to the individual an effective amount of at least one additional therapeutic agent. In further embodiments, the invention provides an anti-TfR antibody modified to improve its safety for use in reducing or inhibiting amyloid plaque formation in a patient at risk or suffering from a neurological disease or disorder (e.g., Alzheimer's disease). An "individual" according to any of the above embodiments is optionally a human. In certain aspects, the anti-TfR antibody of the invention for use in the methods of the invention improves uptake of the neurological disorder drug with which it is coupled.

In a further aspect, the invention provides for the use of a low affinity anti-TfR antibody of the invention in the manufacture or preparation of a medicament. In one embodiment, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent.

In a further aspect, the invention provides a method for treating Alzheimer's disease. In one embodiment, the method comprises administering to an individual having Alzheimer's disease an effective amount of a multispecific antibody of the invention which binds both BACE1 and TfR or both Abeta and TfR. In one such embodiment, the method further comprises administering to the individual an effective amount of at least one additional therapeutic agent. An "individual" according to any of the above embodiments may be a human.

The anti-TfR antibodies of the invention can be used either alone or in combination with other agents in a therapy. For instance, the anti-TfR antibody of the invention may be co-administered with at least one additional therapeutic agent. In certain embodiments, an additional therapeutic agent is a therapeutic agent effective to treat the same or a different neurological disorder as the anti-TfR antibody is being employed to treat. Exemplary additional therapeutic agents include, but are not limited to: the various neurological drugs described above, cholinesterase inhibitors (such as donepezil, galantamine, rovastigmine, and tacrine), NMDA receptor antagonists (such as memantine), amyloid beta peptide aggregation inhibitors, antioxidants, γ-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide immunization, phosphodiesterase inhibitors, serotonin receptor antagonists and anti-amyloid beta peptide antibodies. In certain embodiments, the at least one additional therapeutic agent is selected for its ability to mitigate one or more side effects of the neurological drug.

In certain other such embodiments, the at least one further therapeutic agent is selected for its ability to inhibit or prevent the activation of the complement pathway upon administration of the anti-TfR antibody. Examples of such therapeutic agents include, but are not limited to, agents that interfere with the ability of the anti-TfR antibody to bind to or activate the complement pathway and agents that inhibit one or more molecular interactions within the complement pathway, and are described generally in Mollnes and Kirschfink (Molec. Immunol. 43 (2006) 107-121), the contents of which are expressly incorporated herein by reference.

Such combination therapies noted above and herein encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. In one embodiment, administration of the anti-TfR antibody and administration of an additional therapeutic agent occur within about one month, or within about one, two or three weeks, or within about one, two, three, four, five or six days, of each other. Antibodies of the invention can also be used in combination with other interventional therapies such as, but not limited to, radiation therapy, behavioral therapy, or other therapies known in the art and appropriate for the neurological disorder to be treated or prevented.

An anti-TfR antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The antibody need not be, but is optionally formulated with one or more agents currently used to prevent or treat the disorder in question or to prevent, mitigate or ameliorate one or more side effects of antibody administration. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 40 mg/kg. Thus, one or more doses of about 0.5 mg/kg, 2.0 mg/kg, 4.0 mg/kg, 5.0 mg/kg, 7.5 mg/kg, 10 mg/kg, 15 mg/kg, 20 mg/kg, 25 mg/kg, 30 mg/kg, 35 mg/kg or 40 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. It will be appreciated that one method to reduce impact on reticulocyte populations by administration of anti-TfR antibodies is to modify the amount or timing of the doses such that overall lower quantities of circulating antibody are present in the bloodstream to interact with reticulocytes. In one non-limiting example, a lower dose of the anti-TfR antibodies may be administered with greater frequency than a higher dose would be. The dosage used may be balanced between the amount of antibody necessary to be delivered to the CNS (itself related to the affinity of the CNS antigen-specific portion of the antibody), the affinity of that antibody for TfR, and whether or not red blood cell (i.e., reticulocyte)-protecting, growth and development stimulating, or complement pathway-inhibiting compound(s) are being co- or serially administered with the antibody. The progress of this therapy is easily monitored by conventional techniques and assays as described herein and as known in the art.

It is understood that any of the above formulations or therapeutic methods may be carried out using an immunoconjugate of the invention in place of or in addition to an anti-TfR antibody.

III. ARTICLES OF MANUFACTURE

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-transferrin receptor antibody.

IV. EXAMPLES

The following are examples of methods and compositions of the invention. It is understood that various other embodiments may be practiced, given the general description provided above.

Materials and Methods
Recombinant DNA Techniques
Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.
Gene and Oligonucleotide Synthesis
Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).
Reagents
All commercial chemicals, antibodies and kits were used as provided according to the manufacturer's protocol if not stated otherwise.

Example 1

Immunization of Rabbits and Mice
Immunization of Mice
NMRI mice were immunized genetically, using a plasmid expression vector coding for full-length human or cynomolgus TfR by intradermal application of 100 µg vector DNA, followed by electroporation (2 square pulses of 1000 V/cm, duration 0.1 ms, interval 0.125 s; followed by 4 square pulses of 287.5 V/cm, duration 10 ms, interval 0.125 s. Mice received either 6 or 7 consecutive immunizations at days 0, 14, 28, 42, 56, 70, and 84. The fourth and sixth immunizations were performed with vector coding for cynomolgus TfR; vector coding for human TfR was used for all other immunizations. Blood was taken at days 36, 78 and 92 and serum prepared, which was used for titer determination by ELISA (see below). Animals with highest titers were selected for boosting at day 96, by intravenous injection of either $10^6$ human TF-1 cells or 50 µg of recombinant human soluble TfR lacking the helical domain (extracellular domain of the human TfR beginning at Leu122, ending at Asn608, expressed in HEK293F cells as an N-terminal fusion to human Fc-region and purified by protein A affinity chromatography and size exclusion chromatography, and monoclonal antibodies were isolated by hybridoma technology, based on their ability to bind human and cynomolgus transferrin receptor expressed on the surface of stably transfected CHO-K1 cells (see Example 3).
Immunization of Rabbits
New Zealand White rabbits or transgenic rabbits expressing a humanized antibody repertoire were immunized genetically, using a plasmid expression vector coding for full-length human or cynomolgus TfR, by intradermal application of 400 µg vector DNA, followed by electroporation (5 square pulses of 750 V/cm, duration 10 ms, interval 1 s.). Rabbits received 6 consecutive immunizations at days 0, 14, 28, 56, 84 and 112. The fourth and sixth immunizations were performed with vector coding for cynomolgus TfR; vector coding for human TfR was used for all other immunizations. Blood (10% of estimated total blood volume) was taken at days 35, 63, 91 and 119. Serum was prepared, which was used for titer determination by ELISA (see below), and peripheral mononuclear cells were isolated, which were used as a source of antigen-specific B cells in the B cell cloning process (see Example 2).
Determination of Serum Titers (ELISA)
Human recombinant soluble TfR (R&D Systems Cat. No. 2474-TR) was immobilized on a 96-well NUNC Maxisorb plate at 3 µg/mL, 100 µL/well, in PBS, followed by: blocking of the plate with 2% CroteinC in PBS, 200 µL/well; application of serial dilutions of antisera, in duplicates, in 0.5% CroteinC in PBS, 100 µL/well; detection with (1) HRP-conjugated goat anti-mouse antibody (Jackson Immunoresearch/Dianova 115-036-071; 1/16000) for all mouse sera, (2) HRP-conjugated donkey anti-rabbit IgG antibody (Jackson Immunoresearch/Dianova 711-036-152; 1/16000) for all rabbit sera, (3) rabbit anti-human IgG antibody (Pierce/Thermo Scientific 31423; 1/5000) for sera from transgenic rabbits only, (4) biotinylated goat anti-human kappa antibody (Southern Biotech/Biozol 2063-08, 1/5000) and streptavidin-HRP for sera from transgenic rabbits only; diluted in 0.5% CroteinC in PBS, 100 µL/well. For all steps, plates were incubated for 1 h at 37° C. Between all steps, plates were washed 3 times with 0.05 Tween 20 in PBS. Signal was developed by addition of BM Blue POD Substrate soluble (Roche), 100 µL/well; and stopped by addition of 1 M HCl, 100 µL/well. Absorbance was read out at 450 nm, against 690 nm as reference. Titer was defined as dilution of antisera resulting in half-maximal signal.

Example 2

B-Cell Cloning from Rabbits
Isolation of Rabbit Peripheral Blood Mononuclear Cells (PBMC)

Blood samples were taken of in summary 6 animals (2 wild-type (wt) rabbits and 4 transgenic (tg) rabbits). These rabbits derived from 2 different immunization campaigns: first campaign with 2 wt and 2 tg rabbits and second campaign with 2 tg rabbits (see also the example "Immunization of rabbits"). EDTA containing whole blood was diluted twofold with 1×PBS (PAA, Pasching, Austria) before density centrifugation using lympholyte mammal (Cedarlane Laboratories, Burlington, Ontario, Canada) according to the specifications of the manufacturer. The PBMCs were washed twice with 1×PBS.

EL-4 B5 Medium

RPMI 1640 (Pan Biotech, Aidenbach, Germany) supplemented with 10% FCS (Hyclone, Logan, Utah, USA), 2 mM glutamine, 1% penicillin/streptomycin solution (PAA, Pasching, Austria), 2 mM sodium pyruvate, 10 mM HEPES (PAN Biotech, Aidenbach, Germany) and 0.05 mM β-mercaptoethanol (Gibco, Paisley, Scotland)

Depletion of Cells

First immunization campaign: Sterile 6-well plates (cell culture grade) covered with a confluent monolayer of CHO cells were used to deplete macrophages/monocytes through unspecific adhesion as well as non-specifically binding lymphocytes.

Second immunization campaign: The depletion step using wells covered with CHO cells was omitted since we could not exclude those B-cells producing antibodies that are cross-reactive to hamster transferrin receptor antibodies would be depleted. Therefore, blank sterile 6-well plates (cell culture grade) were used to deplete macrophages and monocytes through unspecific adhesion enabling potential B-lymphocytes producing hamster cross-reactive (and possibly mouse cross-reactive) surface antibodies to reach the next step in the workflow.

For each immunization campaign: each well was filled at maximum with 4 mL medium and up to 6×10$^6$ PBMCs from the immunized rabbit and allowed to bind for 1 h at 37° C. in the incubator. The cells in the supernatant (peripheral blood lymphocytes (PBLs)) were used for the antigen panning step.

Enrichment of B-Cells on the Human Transferrin Receptor 6-well tissue culture plates covered with a monolayer of human transferrin receptor-positive CHO cells were seeded with up to 6×10$^6$ PBLs per 4 mL medium and allowed to bind for 1 h at 37° C. in the incubator. Non-adherent cells were removed by carefully washing the wells 1-2 times with 1×PBS. The remaining sticky cells were detached by trypsin for 10 min. at 37° C. in the incubator. Trypsination was stopped with EL-4 B5 medium. The cells were kept on ice until the immune fluorescence staining.

Immune Fluorescence Staining and Flow Cytometry

The anti-IgG FITC (AbD Serotec, Dusseldorf, Germany) was used for single cell sorting. For surface staining, cells from the depletion and enrichment step were incubated with the anti-IgG FITC antibody in PBS and incubated for 45 min. in the dark at 4° C. After staining the PBMCs were washed two fold with ice cold PBS. Finally the PBMCs were resuspended in ice cold PBS and immediately subjected to the FACS analyses. Propidium iodide in a concentration of 5 µg/mL (BD Pharmingen, San Diego, Calif., USA) was added prior to the FACS analyses to discriminate between dead and live cells.

A Becton Dickinson FACSAria equipped with a computer and the FACSDiva software (BD Biosciences, USA) were used for single cell sort.

B-Cell Cultivation

The cultivation of the rabbit B-cells was prepared by a method similar to that described by Zubler et al. (1985). Briefly, single sorted rabbit B-cells were incubated in 96-well plates with 200 µL/well EL-4 B5 medium containing Pansorbin Cells (1:100000) (Calbiochem (Merck), Darmstadt, Deutschland), 5% rabbit thymocyte supernatant (charge TSN-M13 (10242), MicroCoat, Bernried, Germany) and gamma-irradiated murine EL-4-B5 thymoma cells (2.5× 10$^4$/well) for 7 days at 37° C. in an atmosphere of 5% CO$_2$ in the incubator. The supernatants of the B-cell cultivation were removed for screening and the remaining cells were harvested immediately and were frozen at −80° C. in 100 µL RLT buffer (Qiagen, Hilden, Germany).

Example 3

Identification of Human and Cynomolgus TfR-Binding Antibodies by Cell ELISA

To screen rabbit B-cell or mouse hybridoma supernatants for antibodies recognizing human and cynomolgus TfR, a cell ELISA using stably transfected CHO-K1 cells way employed. Stable transfectants were obtained by transfecting CHO-K1 cells with expression plasmids containing expression cassettes for the human or cynomolgus TfR as well as for neomycin-phosphotransferase. After transfection, cells were diluted in growth medium containing 500 µg/mL G418 (Life Technologies). After appearance of growing clones, cells were detached, stained with MEM-75 (Abcam) or 13E4 (Life Technologies) and PE-labeled secondary antibodies for human or cynomolgus TfR, and highly fluorescent cells sorted as single cells into 96-well-plate wells (FACS Aria). After 7 days of growth, clones were again checked for TfR expression and best expressing clones selected for cell ELISA experiments.

Briefly, 15,000 cells were seeded per well of a 384-well plate and incubated for 18 h at 37° C., 5% CO$_2$. Supernatant was removed using an automated washer (BIOTEK), and 304 of antibody-containing supernatant added to each well, followed by 24 µL of growth medium. After 2 hours of incubation, wells were emptied and 304 of 0.05% glutaraldehyde in PBS added for 45 min. at RT. After 3 washes with PBS/0.025% Tween20 (PBST), 30 µL of anti-rabbit-HRP or anti-mouse-HRP (Southern Biotech) diluted 1:5000 in Blocking buffer was added and plates incubated for 1 hour

Example 4

Cloning and Expression of Anti-TfR Antibodies
Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

PCR Amplification of V-Domains

Total RNA was prepared from B-cells lysate (resuspended in RLT buffer—Qiagen—Cat. No 79216) using the NucleoSpin 8/96 RNA kit (Macherey&Nagel; 740709.4, 740698) according to manufacturer's protocol. RNA was eluted with 60 µL RNAse free water. 6 µL of RNA was used to generate cDNA by reverse transcriptase reaction using the Superscript III First-Strand Synthesis SuperMix (Invitrogen 18080-400) and an oligo-dT-primer according to the manufacturer's instructions. All steps were performed on a Hamilton ML Star System. 4 µL of cDNA were used to amplify the immunoglobulin heavy and light chain variable regions (VH and VL) with the AccuPrime SuperMix (Invitrogen 12344-040) in a final volume of 50 µL using the primers rbHC.up and rbHC.do for the heavy chain, rbLC.up and rbLC.do for the light chain of Wild Type Rabbit B cells and BcPCR_FHLC_leader.fw and BcPCR_huCkappa.rev for the light chain of transgenic rabbit B-cells (see Table below). All forward primers were specific for the signal peptide (of respectively VH and VL) whereas the reverse primers were specific for the constant regions (of respectively VH and VL). The PCR conditions for the RbVH+RbVL were as follows: Hot start at 94° C. for 5 min.; 35 cycles of 20 sec. at 94° C., 20 sec. at 70° C., 45 sec. at 68° C., and a final extension at 68° C. for 7 min. The PCR conditions for the HuVL were as follows: Hot start at 94° C. for 5 min.; 40 cycles of 20 sec. at 94° C., 20 sec. at 52° C., 45 sec. at 68° C., and a final extension at 68° C. for 7 min.

| | |
|---|---|
| rbHC.up (SEQ ID NO: 103) | AAGCTTGCCACCATGGAGACTGGGCTGCGCTGGCTTC |
| rbHCf.do (SEQ ID NO: 104) | CCATTGGTGAGGGTGCCCGAG |
| rbLC.up (SEQ ID NO: 105) | AAGCTTGCCACCATGGACAYGAGGGCCCCCACTC |
| rbLC.do (SEQ ID NO: 106) | CAGAGTRCTGCTGAGGTTGTAGGTAC |
| BcPCR_FHLC_leader.fw (SEQ ID NO: 107) | ATGGACATGAGGGTCCCCGC |
| BcPCR_huCkappa.rev (SEQ ID NO: 108) | GATTTCAACTGCTCATCAGATGGC |

8 µL of 50 µL PCR solution were loaded on a 48 E-Gel 2% (Invitrogen G8008-02). Positive PCR reactions were cleaned using the NucleoSpin Extract II kit (Macherey&Nagel; 740609250) according to manufacturer's protocol and eluted in 50 µL elution buffer. All cleaning steps were performed on a Hamilton ML Starlet System.

Recombinant Expression of Rabbit Monoclonal Bivalent Antibodies

For recombinant expression of rabbit monoclonal bivalent antibodies, PCR-products coding for VH or VL were cloned as cDNA into expression vectors by the overhang cloning method (R S Haun et al., BioTechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Three variants of the basic plasmid were used: one plasmid containing the rabbit IgG constant region designed to accept the VH regions while two additional plasmids containing rabbit or human kappa LC constant region to accept the VL regions.

Linearized expression plasmids coding for the kappa or gamma constant region and VL/VH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

For antibody expression, the isolated HC and LC plasmids were transiently co-transfected into HEK293 cells and the supernatants were harvested after 1 week.

Generation of Vectors for the Expression of Rabbit Monoclonal Monovalent Antibodies For recombinant expression of selected candidates as monoclonal monovalent antibodies rabbit constant regions of all VH chains were converted into human constant regions enclosing the knob-mutation in the CH3 segment. For VL chains derived from rabbit wild-type B-cells, rabbit C kappa constant regions were converted into human. 4 µL of cDNA of the selected candidates were used to amplify the immunoglobulin heavy and light chain variable regions with the AccuPrime SuperMix (Invitrogen 12344-040) in a final volume of 50 µL with forward primers specific for the signal peptide and reverse primers specific for the CDR3-J region with (at the 3' end) overlap sequence (20 bp) homologous to the human constant regions (respectively of VH and VL). The PCR conditions for the VH and VL chain amplification were as follows: Hot start at 94° C. for 5 min.; 35 cycles of 20 sec. at 94° C., 20 sec. at 68° C., 45 sec. at 68° C., and a final extension at 68° C. for 7 min.

PCR-products coding for VH or VL were cloned as cDNA into expression vectors by the overhang cloning method (R S Haun et al., BioTechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Two variants of the basic plasmid were used: one plasmid containing the human IgG constant region designed to accept the new amplified VH chain and a second plasmid containing the human kappa LC constant region to accept the VL chain.

Linearized expression plasmids coding for the kappa or gamma constant region and VL/VH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

Example 5

Transient Expression of the Monovalent Anti-TfR Antibodies

The antibodies were generated in vivo in transiently transfected HEK293 cells (human embryonic kidney cell line 293-derived) cultivated in F17 Medium (Invitrogen Corp.). For transfection "293-Free" Transfection Reagent (Novagen) was used. Antibodies and antibody-based modified molecules as described above were expressed from individual expression plasmids. Transfections were performed as specified in the manufacturer's instructions. Recombinant protein-containing cell culture supernatants were harvested three to seven days after transfection. Supernatants were stored at reduced temperature (e.g. −80° C.) until purification.

General information regarding the recombinant expression of human immunoglobulins in e.g. HEK293 cells is given in: Meissner, P. et al., Biotechnol. Bioeng. 75 (2001) 197-203.

Example 6

Purification of One-Armed Transferrin Receptor Antibodies in High Throughput

The 50 mL clarified supernatants containing one armed antibodies in 96 deep-well plates were loaded on 200 µL MabSelectSuRe columns. After washing steps with PBS at pH 7.4, proteins were eluted with 2.5 mM HCl using Tecan/Atoll-system resulting in 0.5 mL eluate. Eluate was neutralized by 2 M Tris pH 8. Purified proteins were quantified using a Nanodrop spectrophotometer and analyzed by CE-SDS under denaturing and reducing conditions and analytical SEC. To obtain protein with high purity (>95%) a large proportion of the antibodies have to be purified further on size exclusion chromatography to separate from half antibody, knob-knob antibodies and higher aggregates. In the following 500 µL of the samples were injected on Superdex200 10/300GL in 20 mM histidine containing 140 mM NaCl pH 6.0 using Dionex UltiMate 3000. This method allows fractionating 25-30 samples/day and therefore allows polishing a large number of screening hits in one-armed format. Fractions were pooled and analyzed again as described above.

Example 7 hCMEC/D3 Cell Culture for Transcytosis Assays

Medium and supplements for hCMEC/D3 (Weksler, B. B. et al., FASEB J. 19 (2005), 1872-1874) were obtained from Lonza. hCMEC/D3 cells (passages 26-29) were cultured to confluence on collagen-coated coverslips (microscopy) or flasks in EBM2 medium containing 2.5% FBS, a quarter of the supplied growth factors and fully complemented with supplied hydrocortisone, gentamycin and ascorbic acid.

For all transcytosis assays, high density pore ($1 \times 10^8$ pores/cm$^2$) PET membrane filter inserts (0.4 µm, 12 mm diameter) were used in 12-well cell culture plates. Optimum media volumes were calculated to be 400 µL and 1600 µL for apical and basolateral chambers, respectively. Apical chambers of filter inserts were coated with rat tail collagen I (7.5 µg/cm$^2$) followed by fibronectin (5 µg/mL), each incubation lasting for 1 hour at RT. hCMEC/D3 cells were grown to confluent monolayers (approx. $2 \times 10^5$ cells/cm$^2$) for 10-12 days in EMB2 medium.

Example 8

Transcytosis Assay of Monovalent Antibodies

The entire assay was performed in serum-free EBM2 medium which was otherwise reconstituted as described in Example 1. Filter inserts with cells were incubated apically with monovalent antibodies (concentration: 2.67 µg/mL) for 1 hour at 37° C. following which the entire apical and basolateral media were collected. From these values, paracellular flux was calculated. The monolayers were washed at RT in serum-free medium apically (400 µL) and basolaterally (1600 µL) 3×3-5 min. each. All the washes were collected to monitor efficiency of removal of the unbound antibody. Pre-warmed medium was added to the apical chamber and the filters transferred to a fresh 12 well plate (blocked overnight with PBS containing 1% BSA) containing 1600 µL pre-warmed medium. At this point, cells on filters were lysed in 500 µL RIPA buffer in order to determine specific antibody uptake. The remaining filters were incubated at 37° C. and samples collected at various time points to determine apical and/or basolateral release of antibody. The content of antibody in the samples was quantified using a highly sensitive IgG ELISA (see Example 3). For each time point, data were generated from three filter cell cultures.

Example 9

Sensitive IgG ELISA after Transcytosis Assay

The entire procedure was performed at RT using an automated washer for the wash steps. A 384-well plate was coated with 30 µL/well of 1 µg/mL anti-human/mouse-IgG, Fcγ-specific in PBS for 2 hours followed by 1 hour incubation in blocking buffer PBS containing 1% BSA or 1 CroteinC for human and mouse IgG assays, respectively). Serially diluted samples from the transcytosis assay and standard concentrations of the antibody used in the transcytosis assay were added to the plate and incubated for 2 hours. After four washes, 30 µL/well of 50 ng/mL anti-human/mouse-F(ab)2-Biotin in blocking buffer was added and incubated for a further 2 hours. Following 6 washes, 30

µL/well of 50 ng/mL (huIgG assay) or 100 ng/mL (mIgG assay) Poly-HRP40-Streptavidin (Fitzgerald; in PBS containing 1% BSA and 0.05% Tween-20) was added and incubated for 30 min. After 4 washes, immune complexes were detected by addition of 30 µL/well of BM Chemiluminescence Substrate (Roche). The luminescence signal was measured using a luminescence plate reader and concentration calculated using the fitted standard curve. The sensitivity of the assay ranged from 10 pg/mL to 10 ng/mL.

Example 10

Epitope Mapping by Cell ELISA of CHO Cells Transfected with hTfR Mutants

In order to be able determine the epitope regions on human transferrin receptor (hTfR), mutations were introduced into the hTfR sequence at positions, where a cluster of surface-exposed amino acids had different amino acids in the aligned mouse TfR sequence (see Table below), following the rationale that in spite of the significant homology between human and mouse TfR (77% identity), no antibodies directed to the extracellular part are known which show good cross-reactivity between both orthologous. Cloning of plasmids with the corresponding mutations is described above. To map binding of human TfR binders to those epitopes, CHO-K1 cells were transiently transfected with the described plasmids and antibody binding measured in a cell ELISA. Briefly, $10^4$ cells were plated per well of a 96-well plate the day before experiment in normal growth medium (RPMI/10% FCS). The other day, medium was changed to OPTI-MEM Serum-Reduced Medium (Gibco), and 10 µL of a mixture of 1200 µL OPTI-MEM, 12 µg plasmid DNA and 12 µL XtremeGENE transfection reagent (Roche) were added to the wells after 30 minutes of pre-incubation. Cells were incubated for 2 days at 37° C./7.5% $CO_2$, then medium was removed and TfR antibodies added at concentrations between 1 nM and 100 nM in growth medium, followed by 2 h incubation at 4° C. Afterwards, antibody solutions were replaced by 0.05% glutaraldehyde in PBS and cells fixed for 15 min. at RT, then washed twice with PBS and incubated with HRP-conjugated anti-human-Fc secondary antibody (BioRad; 1:2000 in ELISA Blocking Reagent (Roche)) for 1.5 hours at RT. Signal was generated after 3 washes with PBS using 50 µL of TMB per well and absorbance measured at 450 nm.

| Plasmid # | mutations in hTfR |
|---|---|
| 10188 | — |
| 18909 | Thr518Asp/Gln520Lys/Phe521Ser/Gln524Arg |
| 18910 | Arg325Gln |
| 18911 | Ser355Ala/Asp356Arg/Lys358Asn/Thr359Ile |
| 18912 | Asp204Gln/Lys205Ser/Arg208Asn |
| 18913 | Lys574Gly/Glu575Ala/Ile577Thr/Glu578Gln |
| 18914 | Ala196Ile/Gln197Gly/Asn198Gln/Ser199Asn/Val200Met/Ile201Val/Ile202Thr/Val203Ile/Asp204Val/Lys205Gln/Asn206Ser/Gly207Asn/Arg208Gly/Leu209Asn/Val210Leu/Tyr211Asp/Leu212Pro |
| 18974 | Asp245Glu/Tyr247Ser/Thr248Tyr/Pro249Ser |

Example 11

Surface Plasmon Resonance-Based Binding Assay for Human TfR-Antibody Interaction The binding experiment were carried out on a BIAcore B 4000 (GE Healthcare) equipped with C1 sensor chip (GE Healthcare, cat.no. BR1005-35) pre-treated with anti-human Fab antibody (GE Healthcare, cat.no 28-9583-25) using a standard amine coupling chemistry procedure accordingly to the vendor's manual.

For kinetic measurements the sample antibody was immobilized applying a contact time of 60 seconds and a flow rate of 10 µL/min in phosphate buffer saline pH 7.4, 0.05% Tween 20 at 25° C. Recombinant His6-tagged human transferrin receptor (R&D systems, cat.no 2474-TR-050) was applied in increasing concentrations and the signal monitored over the time. An average time span of 150 seconds of association time and 600 seconds of dissociation time at 304/min flow rate was recorded. Data were fit using a 1:1 binding model (Langmuir isotherm).

Example 12

Humanization of the VH and VL Domains of Murine and Rabbit Anti-Transferrin Receptor Antibody The non-human anti-transferrin receptor antibodies were humanized as follows: Based on the characterization of encoding sequences and amino acid sequences that comprise the VH and VL domains of a the non-human anti-transferrin receptor antibodies of the IgG1 class with kappa light chain, a corresponding humanized anti-transferrin receptor antibody was generated by CDR grafting an backward/forward mutations based on the human germline framework VH4_3 and VK1_10 combination for clone 299.

Example 13

Method to Determine Human/Cynomolgus TfR Receptor Affinity

In this example the method for the determination of the human transferrin receptor affinities for the comparison of the dissociation behavior is outlined.

For all analysis the Biotin CAPture Kit from GE Healthcare (Instruction 28-9242-34 AB) was used. First the chip was rehydrated by docking it in the BIAcore T200 instrument. After that, the chip was left on standby with running buffer overnight. For surface preparation the Biotin CAPture Reagent was diluted 1:100 in running buffer (1×PBS, supplemented with 0.25 M NaCl). This solution was injected on Flow Cells 1 to 4 for 360 sec with a flow rate of 2 µL/min. Next the sensor surface was conditioned with three one-minute injections of regeneration solution provided in the Biotin CAPture Kit. This has to be done for the docking procedure or for the first time or after storage. A 100 nM human or cynomolgus, respectively, mono-biotinylated transferrin receptor solution should be injected on Flow Cell 2 for 30 sec at a flow rate of 10 µL/min. For affinity determination injections with six concentrations (500, 250, 125, 62.5, 31.25, 15.625 and 0 nM) were applied. They were injected on the "hu-TfR-flow cell" (e.g. Flow Cell 2 as prepared as outlined above) with an injection time of 180 sec (association) and a flow rate of 10 µL/min. After dissociation phase of 600 sec the surface was regenerated according to the manufacturer's instructions with the regeneration solution provided in the Biotin CAPture Kit and the next cycle was carried out.

The kinetic data was evaluated using the BIAcore T200 evaluation software. Especially the dissociation rate constants of the different human transferrin receptor binders were taken into account after the application of the 1:1 Langmuir binding model.

Example 14

B4000 Relative Ranking of Human/Cynomolgus Transferrin Receptor Dissociation

A CAP sensor chip (provided in the Biotin CAPture Kit, series S #28-9202-34 GE) was mounted into a BIAcore B4000 system, normalized and addressed in a hydrodynamic manner, according to the manufacturer's instructions. In the first cycle the CAP reagent (as provided in the Kit) was addressed to spot 1, 2, 4 and 5 with a flow rate of 10 µL/min for 300 sec. The human transferrin receptor capture took place in spot 1 (human transferrin receptor-biotinylated) and spot 5 (cynomolgus transferrin receptor-biotinylated) with a flow rate of 10 µL/min and a contact time of 30 sec. The receptors were diluted to a concentration of 50 nM with running buffer (1×PBS #28995084, GE Healthcare, supplemented with 0.25 M NaCl). The antibodies were injected into all flow cells in a concentration series of 100 nM, 50 nM, 25 nM and 0 nM for 180 sec at a flow speed of 30 µL/min. Dissociation time was set to 300 sec. Regeneration of the whole complex from the CAP chip has been performed utilizing the regeneration solution provided in the Biotin CAPture Kit (120 sec with a flow rate of 10 µL/min). To control the active protein concentration a second cycle was performed in spot 5 utilizing biotinylated protein A (# P2165-2MG, Sigma) with a flow rate of 10 µL/min and a contact time of 30 sec. Spot 1 was kept empty in this control cycle. The antibodies and the regeneration were handled like in cycle 1. Relevant kinetic data was calculated using the BIAcore B4000 evaluation software. The dissociation from the human transferrin receptor has been determined applying the 1:1 dissociation fit.

The invention claimed is:

1. A method for transporting an antibody across a blood-brain barrier in a subject, comprising administering to the subject an effective amount of a humanized antibody comprising an antigen binding domain that binds to human transferrin receptor and comprises a heavy chain variable domain comprising the hypervariable regions (HVRs) of SEQ ID NO: 66, 68, and 72, and a light chain variable domain comprising the HVRs of SEQ ID NO: 75, 76, and 78.

2. The method according to claim 1, wherein the first antigen binding domain comprises a heavy chain variable domain of SEQ ID NO: 24 and a light chain variable domain of SEQ ID NO: 37.

3. The method according to claim 1, wherein the antibody comprises a second antigen binding domain that binds a brain antigen.

4. The method according to claim 3, wherein the second antigen binding domain binds to Abeta, alpha-synuclein, or CD20.

5. The method according to claim 3, wherein the second antigen binding domain binds to alpha-synuclein and comprises:
   a) a heavy chain variable domain of SEQ ID NO: 93 and a light chain variable domain of SEQ ID NO: 94, or
   b) a heavy chain variable domain of SEQ ID NO: 83 and a light chain variable domain of SEQ ID NO: 84, or
   c) a heavy chain variable domain of SEQ ID NO: 85 and a light chain variable domain of SEQ ID NO: 86, or
   d) a heavy chain variable domain of SEQ ID NO: 87 and a light chain variable domain of SEQ ID NO: 88, or
   e) a heavy chain variable domain of SEQ ID NO: 91 and a light chain variable domain of SEQ ID NO: 92, or
   f) a heavy chain variable domain of SEQ ID NO: 89 and a light chain variable domain of SEQ ID NO: 90.

6. The method according to claim 3, wherein the second antigen binding domain binds to CD20 and comprises a heavy chain variable domain of SEQ ID NO: 79 and a light chain variable domain of SEQ ID NO: 80.

7. The method according to claim 3, wherein the second antigen binding domain binds to Abeta and comprises a heavy chain variable domain of SEQ ID NO: 81 and a light chain variable domain of SEQ ID NO: 82.

8. The method according to claim 3, wherein the humanized antibody is
   a) a full length antibody of the human subclass IgG1, or
   b) a full length antibody of the human subclass IgG4, or
   c) a full length antibody of the human subclass IgG1 with the mutations L234A, L235A and P329G,
   d) a full length antibody of the human subclass IgG4 with the mutations S228P, L235E and optionally P329G,
   e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or f) a full length antibody of the human subclass IgG4 with the mutations S228P, L235E and optionally P329G in both heavy chains and the mutations T366W and S354C in one heavy chain and the mutations T366S, L368A, Y407V and Y349C in the respective other heavy chain.

9. The method according to claim 1, wherein the humanized antibody comprises a homodimeric Fc-region of the human IgG1 subclass optionally with the mutations P329G, L234A and L235A.

10. The method according to claim 1, wherein the humanized antibody comprises a homodimeric Fc-region of the human IgG4 subclass optionally with the mutations P329G, S228P and L235E.

11. The method according to claim 3, wherein the humanized antibody comprises a heterodimeric Fc-region in which
   a) one Fc-region polypeptide comprises the mutation T366W, and the other Fc-region polypeptide comprises the mutations T366S, L368A and Y407V, or
   b) one Fc-region polypeptide comprises the mutations T366W and Y349C, and the other Fc-region polypeptide comprises the mutations T366S, L368A, Y407V, and S354C, or
   c) one Fc-region polypeptide comprises the mutations T366W and S354C, and the other Fc-region polypeptide comprises the mutations T366S, L368A, Y407V and Y349C.

12. The method according to claim 3, wherein the humanized antibody comprises a heterodimeric Fc-region of the human IgG4 subclass in which both Fc-region polypeptides comprise the mutations P329G, L234A and L235A and
   a) one Fc-region polypeptide comprises the mutation T366W, and the other Fc-region polypeptide comprises the mutations T366S, L368A and Y407V, or
   b) one Fc-region polypeptide comprises the mutations T366W and Y349C, and the other Fc-region polypeptide comprises the mutations T366S, L368A, Y407V, and S354C, or
   c) one Fc-region polypeptide comprises the mutations T366W and S354C, and the other Fc-region polypeptide comprises the mutations T366S, L368A, Y407V and Y349C.

13. The method according to claim 1, wherein the humanized antibody comprises a heterodimeric Fc-region of the human IgG4 subclass whereof both Fc-region polypeptides comprise the mutations P329G, S228P and L235E and
   a) one Fc-region polypeptide comprises the mutation T366W, and the other Fc-region polypeptide comprises the mutations T366S, L368A and Y407V, or
   b) one Fc-region polypeptide comprises the mutations T366W and Y349C, and the other Fc-region polypeptide comprises the mutations T366S, L368A, Y407V, and S354C, or
   c) one Fc-region polypeptide comprises the mutations T366W and S354C, and the other Fc-region polypeptide comprises the mutations T366S, L368A, Y407V and Y349C.

14. The method according to claim 3, wherein the subject has neurological disorder.

15. The method according to claim 14, wherein the neurological disorder is a neuropathy disorder, a neurodegenerative disease, cancer, an ocular disease disorder, a seizure disorder, a lysosomal storage disease, amyloidosis, a viral or microbial disease, ischemia, a behavioral disorder, CNS inflammation, Alzheimer's Disease, Parkinson's Disease, multiple sclerosis, CD20 positive cancer with brain metastases, or Her2 positive cancer with brain metastases.

16. The method according to claim 1, wherein the antibody is coupled to a compound.

17. The method according to claim 16, wherein the compound is a therapeutic compound.

18. The method according to claim 16, wherein the compound is an imaging agent or a label.

19. The method according to claim 16, wherein the subject has neurological disorder.

20. The method according to claim 19, wherein the neurological disorder is a neuropathy disorder, a neurodegenerative disease, cancer, an ocular disease disorder, a seizure disorder, a lysosomal storage disease, amyloidosis, a viral or microbial disease, ischemia, a behavioral disorder, CNS inflammation, Alzheimer's Disease, Parkinson's Disease, multiple sclerosis, CD20 positive cancer with brain metastases, or Her2 positive cancer with brain metastases.

* * * * *